(12) United States Patent
Mehta et al.

(10) Patent No.: US 10,245,299 B2
(45) Date of Patent: Apr. 2, 2019

(54) AUTOASSEMBLING PEPTIDES FOR THE TREATMENT OF PULMONARY BULLA

(71) Applicant: 3-D MATRIX, LTD., Tokyo (JP)

(72) Inventors: Manav Mehta, Brighton, MA (US); Hisashi Tsukada, Brookline, MA (US); Eun Seok Gil, Acton, MA (US); Karl Gilbert, Danvers, MA (US); Satoru Kobayashi, Kanagawa (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 15/124,636

(22) PCT Filed: Mar. 10, 2015

(86) PCT No.: PCT/US2015/019743
§ 371 (c)(1),
(2) Date: Sep. 8, 2016

(87) PCT Pub. No.: WO2015/138478
PCT Pub. Date: Sep. 17, 2015

(65) Prior Publication Data
US 2017/0072008 A1 Mar. 16, 2017

Related U.S. Application Data

(60) Provisional application No. 61/953,049, filed on Mar. 14, 2014, provisional application No. 61/950,529, filed on Mar. 10, 2014.

(51) Int. Cl.
| | |
|---|---|
| A61K 38/16 | (2006.01) |
| A61K 38/10 | (2006.01) |
| A61K 38/08 | (2019.01) |
| A61B 17/34 | (2006.01) |
| A61M 16/04 | (2006.01) |

(52) U.S. Cl.
CPC .............. *A61K 38/16* (2013.01); *A61B 17/34* (2013.01); *A61K 38/08* (2013.01); *A61K 38/10* (2013.01); *A61M 16/0463* (2013.01)

(58) Field of Classification Search
CPC ........... A61K 9/007; A61K 38/00; A61K 9/14
See application file for complete search history.

(56) References Cited

U.S. PATENT DOCUMENTS

| | | | |
|---|---|---|---|
| 4,466,641 A | 8/1984 | Heilman et al. | |
| 4,582,640 A | 4/1986 | Smestad et al. | |
| 4,642,117 A | 2/1987 | Nguyen et al. | |
| 4,947,840 A | 8/1990 | Yannas et al. | |
| 5,110,604 A | 5/1992 | Chu et al. | |
| 5,126,141 A | 6/1992 | Henry | |
| 5,236,903 A | 8/1993 | Saiki et al. | |
| 5,292,514 A | 3/1994 | Capecchi et al. | |
| 5,510,102 A | 4/1996 | Cochrum | |
| 5,527,610 A | 6/1996 | Urry | |
| 5,550,187 A | 8/1996 | Rhee et al. | |
| 5,670,483 A | 9/1997 | Zhang et al. | |
| 5,747,452 A | 5/1998 | Ruoslahti et al. | |
| 5,773,577 A | 6/1998 | Cappello | |
| 5,955,343 A | 9/1999 | Holmes et al. | |
| 6,046,160 A | 4/2000 | Obi-Tabot | |
| 6,224,893 B1 | 5/2001 | Langer et al. | |
| 6,280,474 B1 | 8/2001 | Cassidy et al. | |
| 6,548,630 B1 | 4/2003 | Zhang et al. | |
| 6,730,298 B2 | 5/2004 | Griffith-Cima et al. | |
| 6,800,481 B1 | 10/2004 | Holmes et al. | |
| 7,098,028 B2 | 8/2006 | Holmes et al. | |
| 7,449,180 B2 | 11/2008 | Kisiday et al. | |
| 7,713,923 B2 | 5/2010 | Genove et al. | |
| 7,846,891 B2 | 12/2010 | Ellis-Behnke et al. | |
| 8,022,178 B2 | 9/2011 | Horii et al. | |
| 9,012,404 B2 | 4/2015 | Spirio et al. | |
| 9,084,837 B2 | 7/2015 | Ellis-Behnke et al. | |
| 9,162,005 B2 | 10/2015 | Ellis-Behnke et al. | |
| 9,327,010 B2 | 5/2016 | Ellis-Behnke et al. | |
| 9,339,476 B2 | 5/2016 | Norchi et al. | |
| 9,364,513 B2 | 6/2016 | Ellis-Behnke et al. | |
| 9,415,084 B2 | 8/2016 | Ellis-Behnke et al. | |
| 9,439,941 B2 | 9/2016 | Ellis-Behnke et al. | |
| 9,724,448 B2 | 8/2017 | Kobayashi et al. | |
| 2002/0160471 A1 | 10/2002 | Kisiday et al. | |
| 2003/0069177 A1 | 4/2003 | Dubaquie et al. | |
| 2003/0166846 A1 | 9/2003 | Rothstein et al. | |
| 2004/0204561 A1 | 10/2004 | Ellison | |
| 2004/0242469 A1 | 12/2004 | Lee et al. | |
| 2005/0181973 A1 | 8/2005 | Genove et al. | |
| 2006/0084607 A1* | 4/2006 | Spirio .................. | A61K 9/0019 514/21.4 |
| 2006/0148703 A1 | 7/2006 | Lee et al. | |
| 2007/0190603 A1 | 8/2007 | Holmes et al. | |
| 2008/0032934 A1 | 2/2008 | Ellis-Behnke et al. | |
| 2008/0091233 A1 | 4/2008 | Ellis-Behnke et al. | |
| 2009/0162437 A1 | 6/2009 | Horii et al. | |
| 2009/0169598 A1 | 7/2009 | Crutcher | |
| 2010/0143504 A1 | 6/2010 | Spirio et al. | |
| 2010/0311640 A1 | 12/2010 | Genove et al. | |
| 2011/0002880 A1 | 1/2011 | Takamura et al. | |
| 2011/0201541 A1 | 8/2011 | Takamura et al. | |

(Continued)

FOREIGN PATENT DOCUMENTS

| | | |
|---|---|---|
| CA | 2618184 A1 | 12/2006 |
| CN | 101514225 A | 8/2009 |

(Continued)

OTHER PUBLICATIONS

Boyle, Peptide Applications in Biomedicine, Biotechnology and Bioengineering, 2017, 51-86. (Year: 2017).*

(Continued)

*Primary Examiner* — James H Alstrum-Acevedo
*Assistant Examiner* — Kaipeen E Yang
(74) *Attorney, Agent, or Firm* — Choate, Hall & Stewart LLP

(57) ABSTRACT

Materials and methods for treatment of pulmonary bulla are provided. A peptide comprising between about 7 amino acids and about 32 amino acids in a solution may be introduced to a target site. A hydrogel barrier may be provided at the target site in order to treat the pulmonary bulla.

8 Claims, 23 Drawing Sheets

Specification includes a Sequence Listing.

(56) References Cited

U.S. PATENT DOCUMENTS

| | | |
|---|---|---|
| 2012/0010140 A1 | 1/2012 | Ellis-Behnke et al. |
| 2013/0281547 A1 | 10/2013 | Spirio et al. |
| 2013/0296239 A1 | 11/2013 | Takamura et al. |
| 2014/0038909 A1 | 2/2014 | Takamura et al. |
| 2014/0329914 A1 | 11/2014 | Kobayashi et al. |
| 2015/0105336 A1 | 4/2015 | Takamura et al. |
| 2015/0197359 A1 | 7/2015 | Nohara et al. |
| 2015/0258166 A1 | 9/2015 | Spirio et al. |
| 2015/0328279 A1 | 11/2015 | Ellis-Behnke et al. |
| 2016/0000966 A1 | 1/2016 | Kobayashi et al. |
| 2016/0015855 A1 | 1/2016 | Nohara et al. |
| 2016/0213906 A1 | 7/2016 | Horita et al. |
| 2016/0287744 A1 | 10/2016 | Kobayashi et al. |
| 2016/0362451 A1 | 12/2016 | Gil et al. |
| 2017/0072008 A1 | 3/2017 | Mehta et al. |
| 2017/0128622 A1 | 5/2017 | Spirio et al. |
| 2017/0173105 A1 | 6/2017 | Mehta et al. |
| 2017/0173221 A1 | 6/2017 | Mehta et al. |
| 2017/0202986 A1 | 7/2017 | Gil et al. |

FOREIGN PATENT DOCUMENTS

| | | |
|---|---|---|
| EP | 2345433 A1 | 7/2011 |
| EP | 2823830 A1 | 1/2015 |
| JP | 2005-515796 A | 6/2005 |
| JP | 2007-105186 A | 4/2007 |
| JP | 2007-526232 A | 9/2007 |
| JP | 2008-505919 A | 2/2008 |
| JP | 5922749 B2 | 5/2016 |
| WO | WO-94/17811 A1 | 8/1994 |
| WO | WO-1996/040033 A1 | 12/1996 |
| WO | WO-1997/037694 A1 | 10/1997 |
| WO | WO-99/53019 A1 | 10/1999 |
| WO | WO-00/01238 A1 | 1/2000 |
| WO | WO-2002/058749 A2 | 8/2002 |
| WO | WO-2002/062961 A2 | 8/2002 |
| WO | WO-2002/062969 A2 | 8/2002 |
| WO | WO-03/084980 A2 | 10/2003 |
| WO | 03096972 A2 | 11/2003 |
| WO | WO-2004/007532 A2 | 1/2004 |
| WO | WO-2005/014615 A2 | 2/2005 |
| WO | WO-2006/014570 A2 | 2/2006 |
| WO | WO-2006/116524 A1 | 11/2006 |
| WO | WO-2006/138023 A1 | 12/2006 |
| WO | 2007142757 A2 | 12/2007 |
| WO | WO-2008/039483 A2 | 4/2008 |
| WO | WO-2008/073392 A2 | 6/2008 |
| WO | WO-2008/73395 A2 | 6/2008 |
| WO | WO-2008/113030 A2 | 9/2008 |
| WO | WO-2008/134544 A1 | 11/2008 |
| WO | WO-2009/072556 A1 | 6/2009 |
| WO | WO-2010/041636 A1 | 4/2010 |
| WO | 2013030673 A2 | 3/2013 |
| WO | WO-2013/133413 A1 | 9/2013 |
| WO | WO-2014/008400 A2 | 1/2014 |
| WO | WO-2014/076660 A1 | 5/2014 |
| WO | WO-2014/136081 A1 | 9/2014 |
| WO | WO-2014/141143 A1 | 9/2014 |
| WO | WO-2014/141160 A1 | 9/2014 |
| WO | WO-2015/027203 A1 | 2/2015 |
| WO | WO-2015/136370 A2 | 9/2015 |
| WO | WO-2015/138473 A1 | 9/2015 |
| WO | WO-2015/138475 A1 | 9/2015 |
| WO | WO-2015/138478 A1 | 9/2015 |
| WO | WO-2015/138514 A1 | 9/2015 |
| WO | WO-2017/120092 A1 | 7/2017 |

OTHER PUBLICATIONS

C Moser et al.: "Autologous fibrin sealant reduces the incidence of prolonged air leak and duration of the chest tube drainage after lung volume reduction surgery: a prospective randomized blinded study", Journal of Thoracic and Cardiovascular Surgery, vol. 136, No. 4, 2008, p. 843-849, XP025571241, Mosby-Year Book, Inc., St. Louis, MO., ISSN: 0022-5223.

Chemical Abstracts Service, Columbus, Ohio, US; Jin, Ming-Zhe et al.: "Impacts of ligustrazine combined with ICS\LABA on inflammation of lung tissues in rats with chronic obstructive pulmonary disease", XP002740499, retrieved from STN Database accession No. 161:239385 abstract & Jin, Ming-Zhe et al.: "Impacts of ligustrazine combined with ICS/LABA on inflammation of lung tissues in rats with chronic obstructive pulmonary disease", Shiyong Yixue Zazhi, 29(16), 2621-2623 CODEN: SYAFM, ISSN:1006-5725.

Week 201413 Thomson Scientific, London, GB; AN 2013-U98585, XP002740500, "Use of nigella glandulifera freyn seed grass volatile oil for preparing medicine for treating chronic obstructive pulmonary disease", & CN 103 251 690 A (People's Liberation Army Xinjiang Milita) Aug. 21, 2013 (Aug. 21, 2013) abstract.

C. Cunha et al., "3D culture of adult mouse meural stem cells within functionalized self-assembling peptide scaffolds", International Journal of Nanomedicine, pp. 943-955 (2011).

Zhou et al., "Self-assembly of PH and calcium dual-respondive peptide-amphiphillic hydrogel", Journal of Peptide Science, v 19, pp. 737-744 (2013).

3-D Matrix Japan, Ltd. Company Profile Power Point, 16 pages, May 2005 [Japanese].

3-D Matrix Japan, Ltd. Company Profile Power Point, 32 pages, May 2005 (with English translation).

3-D Matrix Japan, Ltd., Products and FAQs, with English Translation, 14 pages. URL: http:/web.archive.org [Retrieved Oct. 21, 2016].

3D Matrix Japan, Company, Technology, Products, Technology, FAQs, Publication, Company, News, Contact, no English translation, 17 pages. URL: http://www.3d-matrix.co.jp/cm02.html [Retrieved Feb. 25, 2005].

3D Matrix Japan, Product Features, with English translation, 2 pages. URL: http://web.archive.org/web/20050416044014/http://www.3d-matrix.eo.jp/pr03.html [Retrieved Feb. 20, 2013].

3D Matrix Japan, Product List, with English translation, 2 pages. URL: http://web.archive.org/web/20050416043834/http://www.3d-matrix.co.jp/pr02.html [Retrieved Aug. 1, 2013].

3D Matrix Japan, Products, with English translation, 2 pages. URL: http://web.archive.org/web/20050415004502/http://www.3d-matrix.eo.jp/pr01.html [Retreived Feb. 20, 2013].

3D-Matrix Japan, Products, FAQs, 8 pages, dispatched Sep. 20, 2011 [English translation].

Abukawa, H. et al, Reconstructing Mandibular Defects Using Autologous Tissue-Engineered Tooth and Bone Constructs, J. Oral Maxillofac. Surg., 67(2):335-347 (2009).

Allen, P. et al, Type I collagen, fibrin and PuraMatrix matrices provide permissive environments for human endothelial and mesenchymal progenitor cells to form neovascular networks, J. Tissue Eng. Regen Med., 5(4):e74-86 (2011).

Altman, M. et al., Conformational behavior of ionic self-complementary peptides, Protein Sci., 9(6):1095-105 (2000).

Anderson, I. The properties of hyaluronan and its role in wound healing, Prof. Nurse., 17(4):232-5 (2001).

Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].

BD PuraMatrix Peptide Hydrogel, Catalog No. 354250, BD Biosciences, 1-16 (2004).

BD PuraMatrix Peptide Hydrogel, Product Specification Sheet, 1 page.

Bouten, C.V. et al, Substrates for cardiovascular tissue engineering, Adv. Drug Deliv. Rev., 63(4-5):221-41 (2011).

Branco, M.C. and Schneider, J.P., Self-assembling materials for therapeutic delivery, Acta. Biomaterialia, 5(3): 817-831 (2009).

(56) References Cited

OTHER PUBLICATIONS

Caplan, M.R. et al., Control of self-assembling oligopeptide matrix formation through systematic variation of amino acid sequence, Biomaterials, 23(1):219-27 (2002).

Caplan, M.R. et al., Effects of systematic variation of amino acid sequence on the mechanical properties of a self-assembling, oligopeptide biomaterial, J. Biomater. Sci. Polymer Edn., 13(3):225-236 (2002).

Caplan, M.R. et al., Self-assembly of a beta-sheet protein governed by relief of electrostatic repulsion relative to van der Waals attraction, Biomacromolecules, 1(4):627-31 (2000).

Censi, R. et al, Hydrogels for protein delivery in tissue engineering, J. Control Release, 161(2):680-692 (2012).

Chambers, J. et al, Memorandum regarding Nucleic Acid and Peptide Claim Interpretation: "A" and "The," USPTO, 2 pages, Dec. 29, 2005.

Chen, K. et al, A Hybrid Silk/RADA-Based Fibrous Scaffold with Triple Hierarchy for Ligament Regeneration, Tissue Eng. Part A., 18(13-14):1399-409 (2012).

Chen, P., Self-assembly of ionic-complementary peptides: a physicochemical viewpoint, Colloids and Surfaces A: Physicochemical and Engineering Aspects, 261(1-3): 3-24 (2005).

Cigognini, D. et al, Evaluation of early and late effects into the acute spinal cord injury of an injectable functionalized self-assembling scaffold, PLoS One., 6(5): e19782 (2011).

Concaro, S. et al, Effect of different materials on the proliferation and migration of articular chondrocytes, Osteoarthritis and Cartilage, 15:Supplement B, pp. B119 (2007).

Cooper et al., "Testing the "critical-size" in calvarial bone defects: revisiting the concept of a critical-sized defect (CSD)," Plast Reconstr Surg. 125(6): 1685-1692, 2010.

Cunha, C. et al, Emerging nanotechnology approaches in tissue engineering for peripheral nerve regeneration, Nanomedicine, 7(1):50-59 (2011).

Curley, J.L. et al, Fabrication of micropatterned hydrogels for neural culture systems using dynamic mask projection photolithography, J. Vis. Exp., 48: 2636 (2011).

Davis, M.E. et al, Custom design of the cardiac microenvironment with biomaterials, Circ Res., 97(1):8-15 (2005).

Davis, M.E. et al, Local myocardial insulin-like growth factor 1 (IGF-1) delivery with biotinylated peptide nanofibers improves cell therapy for myocardial infarction, Proc. Natl. Acad. Sci. USA. ,103(21):8155-8160 (2006).

Davis, M.E. et al., Injectable self-assembling peptide nanofibers create intramyocardial microenvironments for endothelial cells, Circulation, 111(4):442-50 (2005).

Declaration of Dr. Terence Norchi, MD, for use in proceedings against EP 1879606, 4 pages (Mar. 31, 2016).

Declaration of Rutledge Ellis-Behnke for WO 2006/116524, 6 pages, Aug. 10, 2015.

Dojindo catalog,—SulfoBiotics—Sodium sulfide (Na2S), retrieved from http://www.dojindo.eu.com/store/p/885-SulfoBiotics-Sodium-sulfide-Na2S.aspx, 2 pages, downloaded on Apr. 25, 2018.

Dutta, R.C. and Dutta, A.K., Comprehension of ECM-Cell dynamics: A prerequisite for tissue regeneration, Biotechnol. Adv., 28(6):764-769 (2010).

Dégano, I.R. et al, The effect of self-assembling peptide nanofiber scaffolds on mouse embryonic fibroblast implantation and proliferation, Biomaterials, 30(6):1156-65 (2009).

Eisenbud, D. et al, Hydrogel Wound Dressings: Where Do We Stand in 2003?, Ostomy Wound Manage, 49(10): 52-57 (2003).

Ellis-Behnke, R. et al, Crystal clear surgery with self-assembling molecules that act as a barrier in the brain and intestine, Abstracts / Nanomedicine: Nanotechnology, Biology, and Medicine, 1:269-270 (2005).

Ellis-Behnke, R., At the nanoscale: nanohemostat, a new class of hemostatic agent, WIREs Nanomedicine and Nanobiotechnology, 3: 70-78 (2011).

Ellis-Behnke, R.G. et al, Nano neuro knitting: peptide nanofiber scaffold for brain repair and axon regeneration with functional return of vision, Proc. Natl. Acad. Sci. USA, 103(13):5054-5059 (2006).

Ellis-Behnke, R.G. et al., Nano hemostat solution: immediate hemostasis at the nanoscale, Nanomedicine, 2(4):207-15 (2006).

English Translation of Office Action for JP2007-520521 (dated Aug. 24, 2011).

European Search Report for EP 15195734.7, 4 pages (dated Mar. 4, 2016).

Experimental Report conducted at Arch Therapeutics, $(EAKA)_4$ Acetate, 6 pages, (Jul. 2014).

Experimental Report conducted by Ellis-Behnke, 1. Kidneys (rats).

Extended European Search Report for EP 09819170.3, 6 pages (dated Nov. 27, 2013).

Extended European Search Report for EP05770153.4, 7 pages (dated Apr. 7, 2011).

Garreta, E. et al, Osteogenic differentiation of mouse embryonic stem cells and mouse embryonic fibroblasts in a three-dimensional self-assembling peptide scaffold, Tissue Eng., 12(8):2215-27 (2006).

Gelain, F. et al, Slow and sustained release of active cytokines from self-assembling peptide scaffolds, J. Control Release, 145(3):231-239 (2010).

Gelain, F. et al., Designer self-assembling peptide scaffolds for 3-d tissue cell cultures and regenerative medicine, Macromol. Biosci. 7(5):544-551 (2007).

Gervaso, F. et al, The biomaterialist's task: scaffold biomaterials and fabrication technologies, Joints 1(3): 130-137 (2013).

Gherli, T. et al., Comparing warfarin with aspirin after biological aortic valve replacement: a prospective study, Circulation, 110(5):496-500 (2004).

Girt, S. and Bader, A., Improved preclinical safety assessment using micro-BAL devices: the potential impact on human discovery and drug attrition, Drug Discov. Today, 16(9-10):382-397 (2011).

Gonzales, A.L. et al., Integrin interactions with immobilized peptides in polyethylene glycol diacrylate hydrogels, Tissue Eng., 10(11-12):1775-86 (2004).

Guo, H.D. et al, Sustained delivery of VEGF from designer self-assembling peptides improves cardiac function after myocardial infarction, Biochem. Biophys. Res. Commun., 424(1):105-111 (2012).

Guo, H.D. et al, Transplantation of marrow-derived cardiac stem cells carried in designer self-assembling peptide nanofibers improves cardiac function after myocardial infarction, Biochem. Biophys. Res. Commun., 399(1):42-48 (2010).

Guo, J. et al, Reknitting the injured spinal cord by self-assembling peptide nanofiber scaffold, Nanomedicine, 3(4):311-321 (2007).

Gurski, L.A. et al, 3D Matrices for Anti-Cancer Drug Testing and Development, Oncology, Issues Jan./Feb. 2010: 20-25.

Hartgerink, J.D. et al., Peptide-amphiphile nanofibers: a versatile scaffold for the preparation of self-assembling materials, Proc. Natl. Acad. Sci. U S A., 99(8):5133-8 (2002).

Hemmrich, K. et al., Implantation of preadipocyte-loaded hyaluronic acid-based scaffolds into nude mice to evaluate potential for soft tissue engineering, Biomaterials, 26(34):7025-37 (2005).

Henriksson, H. et al, Investigation of different cell types and gel carriers for cell-based intervertebral disc therapy, in vitro and in vivo studies, J. Tissue Eng. Regen. Med., doi: 10.1002/term.480 (2011).

Henriksson, H.B. et al, Transplantation of human mesenchymal stems cells into intervertebral discs in a senogeneic porcine model, Spine (Phila Pa 1976), 34(2):141-148 (2009).

Hilton, J. R. et al, Wound Dressings in Diabetic Foot Disease, Clinical Infectious Diseases, 39: S100-3 (2004).

Hollinger, J.O. and Kleinschmidt, J.C., "The critical size defect as an experimental model to test bone repair materials," J. Craniofac Surg 1990(1): 60-68.

Holmes, T.C. et al., Extensive neurite outgrowth and active synapse formation on self-assembling peptide scaffolds, Proc. Natl. Acad. Sci. U S A., 97(12):6728-33 (2000).

Horii, A. et al, Biological designer self-assembling peptide nanofiber scaffolds significantly enhance osteoblast proliferation, differentiation and 3-D migration, PLoS One, 2(2):e190 (2007).

(56) References Cited

OTHER PUBLICATIONS

Hsieh, P.C. et al, Controlled delivery of PDGF-BB for myocardial protection using injectable self-assembling peptide nanofibers, J. Clin. Invest.,116(1):237-248 (2006).

Hsieh, P.C.H. et al, Local controlled intramyocardial delivery of platelet-derived growth factor improves postinfarction ventricular function without pulmonary toxicity, Circulation, 114(7):637-644 (2006).

Huang, A.H. et al, Mechanics and mechanobiology of mesenchymal stem cell-based engineered cartilage, J. Biomech., 43(1):128-136 (2010).

Hwang, W. et al., Supramolecular structure of helical ribbons self-assembled from a beta-sheet peptide, The Journal of Chemical Physics, 118(1): 389-397 (2003).

International Preliminary Report on Patentability, PCT/IB2015/00868, 10 pages, dated Sep. 13, 2016.

International Search Report for PCT/IB2015/000868, 7 pages (dated Dec. 8, 2015).

International Search Report for PCT/JP2009/067367, 2 pages (dated Dec. 15, 2009).

International Search Report for PCT/US2005/024198, 3 pages (dated Feb. 23, 2006).

International Search Report for PCT/US2007/025271, 6 pages (dated Sep. 4, 2008).

International Search Report for PCT/US2015/019738, 4 pages (dated Jun. 19, 2015).

International Search Report for PCT/US2015/019740, 5 pages (dated May 26, 2015).

International Search Report for PCT/US2015/019743, 5 pages (dated Jun. 12, 2015).

International Search Report on Patentability for PCT/US2015/019796, 6 pages, dated Sep. 13, 2016.

Kates, Declaration of Steven Kates, Ph.D., Re: Japanese Patent Application No. 2008-509090 ("Third Party Declaration") (2012).

Kim, J.H. et al, The enhancement of mature vessel formation and cardiac function in infarcted hearts using dual growth factor delivery with self-assembling peptides, Biomaterials, 32(26):6080-6088 (2011).

Kisiday, J. et al, Self-assembling peptide hydrogel fosters chondrocyte extracellular matrix production and cell division: implications for cartilage tissue repair, Proc. Natl. Acad. Sci. USA, 99(15):9996-10001 (2002).

Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).

Komatsu, S. et al, The Neutral Self-Assembling Peptide Hydrogel SPG-178 as a Topical Hemostatic Agent, PLoS ONE, 9(7): e102778 (2014).

Kopecek, J. and Yang, J., Peptide-directed self-assembly of hydrogels, Acta Biomaterialia, 5(3): 805-816 (2009).

Kumada, Y. and Zhang, S., Significant type I and type III collagen production from human periodontal ligament fibroblasts in 3D peptide scaffolds without extra growth factors, PLoS One, 5(4):e10305 (2010).

Kumada, Y. et al., Functionalized scaffolds of shorter self-assembling peptides containing MMP-2 cleavable motif promote fibroblast proliferation and significantly accelerate 3-D cell migration independent of scaffold stiffness, Soft Matter, The Royal Society of Chemistry, 7 pages (2010).

Kyle, S. et al, Recombinant self-assembling peptides as biomaterials for tissue engineering, Biomaterials, 31: 9395-9405 (2010).

Kyle, S. et al., Production of self-assembling biomaterials for tissue engineering, Trends Biotechnol., 27(7):423-33 (2009).

Lampe, K.J. and Heilshorn, S.C., Building stem cell niches from the molecule up through engineered peptide materials, Neurosci. Lett., 519(2):138-46 (2012).

Lee, J. et al., Three-dimensional cell culture matrices: state of the art, Tissue Eng. Part B Rev., 14(1):61-86 (2008).

Leon, E.J. et al., Mechanical properties of a self-assembling oligopeptide matrix, J. Biomater. Sci. Polymer Edn., 9(3):297-312 (1998).

Leung, G.K. et al, Peptide nanofiber scaffold for brain tissue reconstruction, Methods Enzymol., 508:177-190 (2012).

Li, X. et al, Engineering neural stem cell fates with hydrogel design for central nervous system regeneration, Progress in Polymer Science, 37(8):1105-1129 (2012).

Liedmann, A. et al, Cultivation of human neural progenitor cells in a 3-dimensional self-assembling peptide hydrogel, J. Vis. Exp., (59):e3830 (2012).

Liu, J. et al, Controlled release of paclitaxel from a self-assembling peptide hydrogel formed in situ and antitumor study in vitro, Int. J. Nanomedicine, 6:2143-53 (2011).

Liu, W-M. et al., Diversification of Microfluidic Chip for Applications in Cell-Based Bioanalysis, Chinese Journal of Analytical Chemistry, 40(1): 24-31 (2012).

Loo, Y. et al., From short peptides to nanofibers to macromolecular assemblies in biomedicine, Biotechnol. Adv., 30(3):593-603 (2012).

Luo, Z. and Zhang, S., Designer nanomaterials using chiral self-assembling peptide systems and their emerging benefit for society, Chem. Soc. Rev., 41(13):4736-54 (2012).

Luo, Z. et al, Fabrication of self-assembling d-form peptide nanofiber scaffold d-EAK16 for rapid hemostasis, Biomaterials, 32(8):2013-20 (2011).

Maher, S.A. et al, A nano-fibrous cell-seeded hydrogel promotes integration in a cartilage gap model, J. Tissue Eng. Regen. Med., 4(1):25-29 (2010).

Marini, D.M. et al., Left-Handed Helical Ribbon Intermediates in the Self-Assembly of a beta-Sheet Peptide, Nano Letters, 2(4):295-299 (2002).

Marston, W.A. et al., Initial report of the use of an injectable porcine collagen-derived matrix to stimulate healing of diabetic foot wounds in humans, Wound Repair Regen., 13(3):243-7 (2005).

Masuhara, H. et al, Novel infectious agent-free hemostatic material (TDM-621) in cardiovascular surgery, Ann. Thorac. Cardiovasc. Surg. Methods Enzymol., 18(5):444-451 (2012).

McGrath, A.M. et al, BD © PuraMatrix® peptide hydrogel seeded with Schwann cells for peripheral nerve regeneration, Brain Res. Bull., 83(5):207-213 (2010).

Meng, H. et al, Peripferal Nerve Regeneration in Response to Synthesized Nanofiber Scaffold Hydrogel, Life Science Journal, 9(1): 42-46 (2012).

Misawa, H. et al, PuraMatrix facilitates bone regeneration in bone defects of calvaria in mice, Cell Transplant, 15(10):903-910 (2006).

Mooney, M.P. and Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C.,editors. Bone Tissue Engineering. Boca Raton, FL: C.R.C. Press, pp. 217-244 (2005).

Nakahara, H. et al, Bone repair using a hybrid scaffold of self-assembling peptide PuraMatrix and polyetheretherketone cage in rats, Cell Transplant, 19(6):791-797 (2010).

Narmoneva, D.A. et al, Endothelial cells promote cardiac myocyte survival and spatial reorganization: implications for cardiac regeneration, Circulation, 110(8):962-968 (2004).

Narmoneva, D.A. et al., Self-assembling short oligopeptides and the promotion of angiogenesis, Biomaterials, 26(23):4837-46 (2005).

Nichol, J.W. et al, Co-culture induces alignment in engineered cardiac constructs via MMP-2 expression, Biochem. Biophys. Res. Commun., 373(3):360-365 (2008).

Nishimura, A. et al, Controlled release of insulin from self-assembling nanofiber hydrogel, PuraMatrix®: application for the subcutaneous injection in rats, Eur. J. Pharm. Sci., 45(1-2):1-7 (2012).

Ortinau, S. et al, Effect of 3D-scaffold formation on differentiation and survival in human neural progenitor cells, Biomed. Eng. Online, 9(1):70 (2010).

Osterman, D.G. and Kaiser, E.T., Design and characterization of peptides with amphiphilic beta-strand structures, J. Cell Biochem., 29(2):57-72 (1985).

Patterson, J. et al., Biomimetic materials in tissue engineering, Materialstoday, 13(1-2): 14-22 (2010).

(56) References Cited

OTHER PUBLICATIONS

Saiga, K. et al, Combined use of bFGF and GDF-5 enhances the healing of medial collateral ligament injury, Biochem. Biophys. Res. Commun., 402(2):329-334 (2010).
Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.
Scalfani, A.P. And Romo III., T., Injectable fillers for facial soft tissue enhancement, Facial Plast. Surg., 16(1):29-34 (2000).
Segers, V.F. and Lee, R.T., Local delivery of proteins and the use of self-assembling peptides, Drug Discov. Today, 12(13-14):561-8 (2007).
Segers, V.F.M. and Lee, R.T., Stem-cell therapy for cardiac disease, Nature 451, 937-942 (2008).
Segers, V.F.M. et al, Local delivery of protease-resistant stromal cell derived factor-1 for stem cell recruitment after myocardial infarction, Circulation, 116(15):1683-1692 (2007).
Semino, C.E. et al., Entrapment of migrating hippocampal neural cells in three-dimensional peptide nanofiber scaffold, Tissue Eng., 10(3-4):643-55 (2004).
Semino, C.E., Self-assembling peptides: from bio-inspired materials to bone regeneration, J. Dent Res., 87(7):606-616 (2008).
Serban, M.A. et al, Effects of extracellular matrix analogues on primary human fibroblast behavior, Acta Biomater., 4(1):67-75 (2008).
Shirai, K. et al, Multipotency of clonal cells derived from swine periodontal ligament and differential regulation by fibroblast growth factor and bone morphogenetic protein, J. Periodontal Res., 44(2):238-247 (2009).
Shivachar, A.C., Isolation and Culturing of Glial, Neuronal and Neural Stem Cell Types Encapsulated in Biodegradable Peptide Hydrogel, Topics in Tissue Engineering, vol. 4. Eds. N Ashammakhi, R Reis, & F Chiellini © 2008.
Sigma-Aldrich catalog, Sodium Bicarbonate, retrieved from https://www.sigmaaldrich.com/catalog/product/sigma/s5761 ?lang=en&region=US, 4 pages, downloaded on Apr. 25, 2018.
Song, H. et al, Hemostatic efficacy of biological self-assembling peptide nanofibers in a rat kidney model, Macromol Biosci., 10(1):33-39 (2010).
Spencer, N.J. et al, Peptide- and collagen-based hydrogel substrates for in vitro culture of chick cochleae, Biomaterials, 29(8):1028-1042 (2008).
Sur, S. et al, A hybrid nanofiber matrix to control the survival and maturation of brain neurons, Biomaterials, 33(2):545-55 (2012).
Takei, J., 3-Dimensional Cell Culture Scaffold for Everyone: Drug Screening, Tissue Engineering and Cancer Biology, AATEX, 11(3): 170-176 (2006).
The University of Waterloo, Buffer Solutions, retrieved from https://web.archive.org/web/20001213162000/http://www.science.uwaterloo.ca/-cchieh/cact/c123/buffer.htm, 6 pages, downloaded on Apr. 24, 2018.
Third Part Observation for EP 05770153.4, with exhibits, 71 pages (Aug. 25, 2014).
Third Party Observation for JP 2008-509090, 43 pages, references in English (Aug. 10, 2011).
Thonhoff, J.R. et al, Compatibility of human fetal neural stem cells with hydrogel biomaterials in vitro, Brain Res., 1187:42-51 (2008).
Tokunaga, M. et al, Implantation of cardiac progenitor cells using self-assembling peptide improves cardiac function after myocardial infarction, J. Mol. Cell. Cardiol., 49(6):972-983 (2010).
Tokunou, T. et al, Engineering insulin-like growth factor-1 for local delivery, FASEB J., 22(6):1886-1893 (2008).
Tortora, G. J., Principles of Human Anatomy, Fifth Edition, Chapter 4: The Integumentary System, 98-100 (1989).
Uemura, M. et al, Matrigel supports survival and neuronal differentiation of grafted embryonic stem cell-derived neural precursor cells, J. Neurosci. Res., 88(3):542-551 (2010).

Van Putten, S.M. et al, The downmodulation of the foreign body reaction by cytomegalovirus encoded interleukin-10, Biomaterials, 30(5):730-735 (2008).
Wang, Q.G. et al, The composition of hydrogels for cartilage tissue engineering can influence glycosaminoglycan profile, Eur. Cell Mater, 19:86-95 (2010).
Wang. T. et al, Molecular Mechanisms of RAD16-1 Peptide on Fast Stop Bleeding in Rat Models, Int. J. Mol. Sci., 13: 15279-15290 (2012).
Written Opinion for PCT/IB2015/000868, 9 pages (dated Dec. 8, 2015).
Written Opinion for PCT/JP2009/067367, 5 pages (dated Dec. 15, 2009).
Written Opinion for PCT/US2005/024198, 4 pages (dated Feb. 23, 2006).
Written Opinion for PCT/US2015/019738, 5 pages (dated Jun. 19, 2015).
Written Opinion for PCT/US2015/019740, 5 pages (dated May 26, 2015).
Written Opinion for PCT/US2015/019743 (Material for Treating Pulmonary Bulla, filed Mar. 10, 2015), issued by ISA/EPO, 5 pages (dated Jun. 12, 2015).
Yamaoka, H. et al, Cartilage tissue engineering using human auricular chondrocytes embedded in different hydrogel materials, J. Biomed. Mater Res. A., 78(1):1-11 (2006).
Ye, Z. et al, Temperature and pH effects on biophysical and morphological properties of self-assembling peptide RADA16-I., J. Pept. Sci., 14(2):152-162 (2008).
Yla-Outinen, L. et al, Three-dimensional growth matrix for human embryonic stem cell-derived neuronal cells, J. Tissue Eng. Regen. Med., doi: 10.1002/term.1512 (2012).
Yokoi, H. et al., Dynamic reassembly of peptide RADA16 nanofiber scaffold, Proc. Natl. Acad. Sci. U S A, 102(24):8414-9 (2005).
Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).
Yu, Y.C. et al., Construction of biologically active protein molecular architecture using self-assembling peptide-amphiphiles, Methods Enzymol., 289:571-87 (1997).
Zarzhitsky, S. and Rapaport, H., The interactions between doxorubicin and amphiphilic and acidic β-sheet peptides towards drug delivery hydrogels, J. Colloid Interface Sci. 360(2):525-531 (2011).
Zhang, S. et al, PuraMatrix: Self-Assembling Peptide Nanofiber Scaffolds, Scaffolding in Tissue Engineering, Chapter 15, 217-238 (1992).
Zhang, S. et al, Self-assembling peptides in biology, materials science and engineering, Peptide Science—Present and Future, 737-744 (1999).
Zhang, S. et al, Self-complementary oligopeptide matrices support mammalian cell attachment, Biomaterials, 16(18): 1385-1393 (1995).
Zhang, S. et al., Building from the bottom up, Materials Today, 20-27 (2003).
Zhang, S. Self-assembling peptide materials, Amino Acids, Pept. Proteins, 37:40-65 (2012).
Zhang, S., Beyond the Petri dish, Nat. Biotechnol., 22(2):151-2 (2004).
Zhang, S., Designer SelfLAssembling Peptide Nanofiber Scaffolds for Study of 3LD Cell Biology and Beyond, Cancer Research, 335-362 (2008).
Zhang, S., Emerging biological materials through molecular self-assembly, Biotechnol. Adv., 20(5-6):321-39 (2002).
Zhang, S., Fabrication of novel biomaterials through molecular self-assembly, Nat. Biotechnol., 21(10):1171-8 (2003).
Zhang, S., Hydrogels: Wet or let die, Nat. Mater., 3(1):7-8 (2004).
Zhao, X. et al., Recent development of peptide self-assembly, Progress in Natural Science 18, 6(10):653-660 (2008).
Zhaoyang, Y. et al., Temperature and pH effects on biophysical and morphological properties of self-assembling peptide RADA16-T, Journal of Peptide Science, 14(2):152-162 (2008).

* cited by examiner

AUTOASSEMBLING PEPTIDES FOR THE TREATMENT OF PULMONARY BULLA

CROSS-REFERENCE TO RELATED APPLICATIONS

This application is a U.S. national phase application under 35 U.S.C. § 371 of International PCT Application Serial No. PCT/US2015/019743 filed on Mar. 10, 2015, titled "AUTOASSEMBLING PEPTIDES FOR THE TREATMENT OF PULMONARY BULLA," which claims priority under 35 U.S.C. § 119(e) to U.S. Provisional Patent Application Ser. No. 61/953,049, filed on Mar. 14, 2014, titled "MATERIAL FOR TREATING PULMONARY BULLA," and to U.S. Provisional Patent Application Ser. No. 61/950,529, filed on Mar. 10, 2014, titled "SELF-ASSEMBLING PEPTIDE HYDROGELS."

SEQUENCE LISTING

The instant application contains a Sequence Listing which has been submitted electronically in ASCII format and is hereby incorporated by reference in its entirety. Said ASCII copy, created on Mar. 10, 2015, is named T2071-7004WO_SL.txt and is 1,760 bytes in size.

FIELD OF THE DISCLOSURE

This disclosure generally relates to materials and methods that may be used in medical, research, and industrial applications. More particularly, this disclosure relates to materials and methods that may be used for treatment of pulmonary bulla.

SUMMARY

In embodiments, a method of treating a pulmonary bulla in a subject is provided. The method comprises introducing a delivery device to a target area of the pulmonary bulla of the subject. The method also comprises positioning an end of the delivery device in the target area in which treatment of a pulmonary bulla is desired. The method also comprises administering through the delivery device a solution comprising a self-assembling peptide comprising between about 7 amino acids and 32 amino acids in an effective amount and in an effective concentration to the target area to form a hydrogel barrier under physiological conditions of the target area to treat the pulmonary bulla. The method also comprises removing the delivery device from the target area.

A kit for treating a pulmonary bulla in a subject is provided. The kit comprises a self-assembling peptide comprising between about 7 amino acids and about 32 amino acids in an effective amount to form a hydrogel barrier under physiological conditions to treat the pulmonary bulla. The kit also comprises instructions for administering the self-assembling peptide to a target area of the pulmonary bulla of the subject.

A composition comprising a self-assembling peptide comprising between about 7 amino acids and 32 amino acids in an effective amount and in an effective concentration for use in forming a hydrogel barrier under physiological conditions to treat a pulmonary bulla is provided. In embodiments, a method of facilitating treating a pulmonary bulla in a subject is provided. The method comprises providing a solution comprising a self-assembling peptide comprising between about 7 amino acids to about 32 amino acids in an effective amount and in an effective concentration to form a hydrogel barrier under physiological conditions to allow treatment of the pulmonary bulla. The method also comprises providing instructions for administering the solution to a target area of the pulmonary bulla through introduction of the solution through a delivery device positioned in the pulmonary bulla.

A method of facilitating treating a pulmonary bulla in a subject is provided. The method comprises providing a solution comprising a self-assembling peptide comprising between about 7 amino acids to about 32 amino acids in an effective amount and in an effective concentration to form a hydrogel barrier in a target area of the lung under physiological conditions to treat the pulmonary bulla. The method further comprises providing instructions for administering the solution to the target area of the lung through introduction of the solution through a delivery device positioned in the target area.

A macroscopic scaffold consisting essentially of a plurality of self-assembling peptides is provided. Each of the self-assembling peptides comprises between about 7 amino acids and about 32 amino acids in an effective amount that is capable of being positioned within a target area of a pulmonary bulla.

DETAILED DESCRIPTION

Figure 1A:
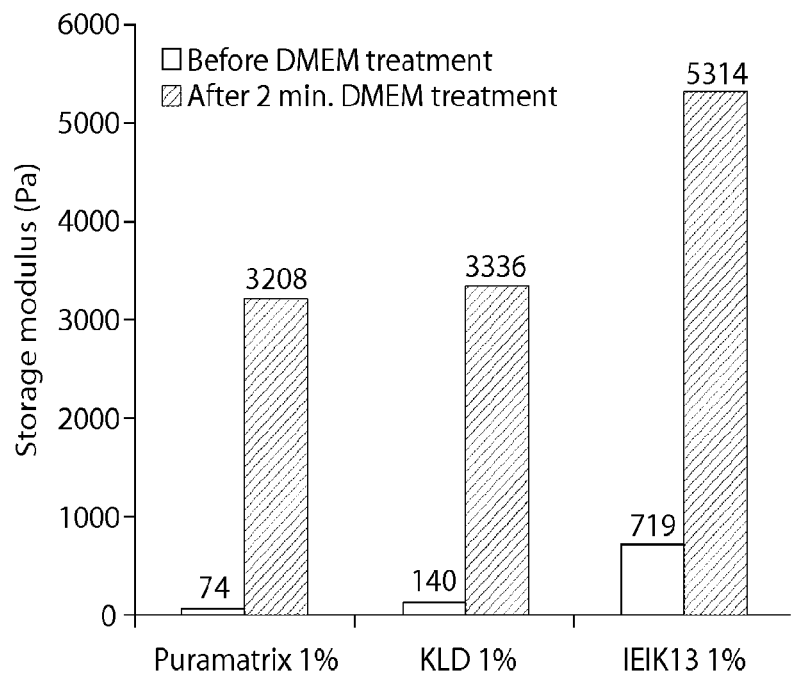
FIGS. 1A-1B present data discussed in Example 1.

The systems and methods of the present disclosure may facilitate treatment of pulmonary bulla.

The materials and methods of the present disclosure may provide treatments for blebs. The lung comprises lung tissue, comprising alveoli, bronchi, and bronchioles, and a thin, membranous covering referred to as the pleura. This covering may prevent inhaled air from travelling from the lung to the area inside the thoracic cavity. "Blebs' are blister-like air pockets that form on the surface of the lung. Bulla (bullae, plural) refers to air-filled cavities within the lung tissue. Blebs and bullae may be related to an underlying disease such as emphysema, or chronic obstructive pulmonary disease. Blebs and bullae may also be found in healthy subjects with no other medical issues or conditions.

If blebs or bullae rupture, the air may travel from the airways to the thoracic cavity, which create a pneumothorax, which may be referred to as a lung collapse. Current treatments for pulmonary bullae or blebs may involve resection or removal, as necessary, in the form of a bullectomy. Stapling may also be employed. Pulmonary bullae and blebs often recur so that the subject may require frequent, multiple procedures. These procedures may prove to be taxing for the subject. Additionally, there are post-operative complications, including risk of air leakage from the reception location.

It may be possible to introduce fibrin glue to the ruptured bulla or bleb, which can be an effective treatment to a pneumothorax condition. However, in certain instances there may be issues regarding allergic reactions to biological materials such as fibrin glue.

It may be possible to utilize a self-assembling peptide solution as a filler to collapse a pulmonary bulla or bleb or to apply subsequent to collapsing the bulla. This treatment may be used instead of a bullectomy. The peptide may be applied one or more times, safely to a target site of a subject.

This disclosure provides for treatment methods including identification of a bulla, collapse of the bulla, and application of the self-assembly peptide solutions or gels in the bulla to provide an air sealant that provides a burst pressure of over 35 cmH2O.

The bulla that may be treated by the methods and materials of the present disclosure may be of a wide range of sizes. Generally, bulla that may be identified for treatment may be considered dangerous to a subject's health based on an evaluation or imaging of the area of the bulla. In some embodiments, the bulla may be detectable using non-invasive imaging. In some embodiments that may have a volume of about 0.1 mL to about 5 mL. The bulla that may be treated may be in a range of about 0.2 mL to about 1 mL.

A primary goal may be to prevent air leakage (pneumothorax). A secondary goal may be regeneration of the parenchamae and prevention of re-occurrence of bullae.

The bullae collapse may be accomplished with a needle. This will create a bullae with an air leak. The peptide solution or gel may be injected into the bulla cavity and/or pleura to seal the air leak.

In certain embodiments, the treatment may provide for a burst pressure of at least 20 cmH$_2$O, at least 25 cmH$_2$O, at least 30 cmH$_2$O and in certain instances, at least 35 cmH$_2$O.

In accordance with one or more embodiments, a self-assembling peptide may treat a pulmonary bulla or a bleb. Throughout this disclosure, references to bulla may also apply to blebs. The leakage may be created postoperatively. The materials, systems and methods disclosed herein may facilitate mucosal epithelium formation in some non-limiting embodiments.

The self-assembling peptides of the present disclosure may include application, for example, administration of the self-assembling peptides to a predetermined or desired target area. The self-assembling peptide may be administered to a target area in the form of a peptide solution, hydrogel, membrane or other form. A target area may be a predetermined area of a subject that requires a particular treatment. In some embodiments, the target area may relate to a surgical site.

During self-assembly, the peptide may form nanofibers. The self-assembly may cause gelling of the peptide in solution. The gelling may provide or form a hydrogel. The peptide may form a beta-sheet spontaneously in the solution under neutral pH level. The peptide may form a beta-sheet spontaneously in the solution under physiological conditions and/or in the presence of a cation and/or anion.

The methods and materials of the present disclosure may be used after a surgical procedure. For example, the solution comprising the self-assembling peptide may be administered after a surgical procedure.

The methods of the present disclosure may comprise introducing a delivery device to a target area of the pulmonary bulla of a subject. The method may provide positioning an end of the delivery device in the target area in which treatment of the pulmonary bulla is desired. Positioning an end of the delivery device in the target area may comprise positioning an endotracheal tube in the target area.

In some embodiments, the method may further comprise identifying the pulmonary bulla or a portion of the pulmonary bulla as the target site.

The method of the present disclosure may also comprise administering the self-assembling peptides to a predetermined or desired target. The self-assembling peptide may be administered to a target area in the form of a peptide solution, hydrogel, membrane or other form. A target area may be a predetermined area of a subject that requires a particular treatment. In some embodiments, the target area may relate to a surgical site or the site of a pulmonary bulla. For example, a surgical site may be a site where surgery was performed, such as a pulmonary-related surgery. The systems and methods of the present disclosure may not involve resection and/or stapling of the pulmonary bullae.

In embodiments, the method may comprise collapsing the pulmonary bulla. The bulla may be collapsed prior to administration of the solution comprising the self-assembling peptide. The pulmonary bulla may be collapsed after administration of the solution comprising the self-assembling peptide. A cavity of the pulmonary bulla may be filled with the solution comprising the self-assembling peptide through connecting bronchioles An endotracheal tube may be used by insertion through the primary bronchus and into the lung. The administration may occur through the delivery device to the target area to form a hydrogel barrier. This may occur under physiological conditions of the target area to treat the pulmonary bulla.

The materials and methods may comprise treatment, prevention, or occlusion of a pulmonary bulla.

As used herein, the term "treatment" is intended in include partial or complete treatment of a bulla by way of collapsing and/or providing an occlusion or blockage of an area in which leakage, for example, air leakage, is occurring. Generally, the bulla and/or leakage is unwanted and, thus, the treatment remedies the bulla and/or leakage, and provides for healing of the target area of treatment. Treatment of a subject may include one or more of curing, alleviating, relieving or improving a subject with a disorder, for example, a bulla and/or leakage, beyond that expected in the absence of such treatment. The treatment may be a minimally invasive treatment, including minimally invasive application or administration of the solution comprising the self-assembling peptide.

As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

The treatment, prevention or occlusion may be partial or complete. The materials and methods may include addressing a pulmonary bulla. The materials and methods may include administration, application, or injection of a self-assembling peptide, or a solution comprising a self-assembling peptide, or a composition comprising a self-assembling peptide, to a predetermined or desired target area.

The method of treating a pulmonary bulla may further comprise removing the delivery device from the target area. The method may further comprise visualizing a region comprising the target area prior to introducing the delivery device. Visualization of the region comprising the target area may occur subsequent to removing the delivery device from the target area. Monitoring of the target area may also occur during the procedure and subsequent to the procedure, for example, subsequent to removing the delivery device.

The method of treatment may further comprise preparing the solution comprising the self-assembling peptide. In some embodiments, the method of treatment may further comprise evaluating the subject to determine a need for treating a pulmonary bulla and preparing the solution based on the step of evaluating.

The method of treatment may comprises administering self-assembling peptide solutions to the bulla until the bulla is filled to attempt to provide no air leakage.

The term "self-assembling peptide" may refer to a peptide that may exhibit a beta-sheet structure in aqueous solution in the presence of specific conditions to induce the beta-sheet structure. These specific conditions may include adjusting the pH of a self-assembling peptide solution. The adjustment may be an increase or a decrease in the pH of the self-assembling peptide solution. The increase in pH may be an increase in pH to a physiological pH. The specific conditions may also include adding a cation, such as a monovalent cation or a divalent cation, to a self-assembling peptide solution. The specific conditions may also include adding an anion, such as a monovalent anion or a divalent anion, to a self-assembling peptide solution. The specific conditions may include conditions related to the site of a surgery or a target site of pulmonary bulla. The self-assembling peptides may be referred to as or be a part of a composition, peptide solution, peptide powder, hydrogel, or scaffold.

The term "self-assembling peptide" may refer to a peptide comprising a self-assembling motif. Self-assembling peptides are peptides that are capable of self-assembly into structures including but not limited to, macroscopic membranes or nanostructures.

The term "hydrogel" may refer to a material that is comprised of a polymer and a high percentage of water, for example, at least 90% water.

The self-assembling peptide may be an amphiphilic self-assembling peptide. By "amphiphilic" it is meant that the peptide comprises hydrophobic portions and hydrophilic portions. In some embodiments, an amphiphilic peptide may comprise, consist essentially of, or consist of alternating hydrophobic amino acids and hydrophilic amino acids. By alternating, it is meant to include a series of three or more amino acids that alternate between a hydrophobic amino acid and a hydrophilic amino acid, and it need not include each and every amino acid in the peptide sequence alternating between a hydrophobic and a hydrophilic amino acid. The self-assembling peptide, also referred to herein as "peptide," may be administered to the pre-determined or desired target area in the form of a self-assembling peptide solution, composition, hydrogel, membrane, scaffold or other form. The hydrogel may also be referred to as a membrane or scaffold throughout this disclosure. The pre-determined or desired target area may be at or near the location of a pulmonary bulla. The pre-determined or desired target area may be established based on the site of or other area that may have undergone a surgical procedure, or an unintentional or intentional trauma.

The solution comprising a self-assembling peptide, also referred to as a self-assembling peptide solution, may be an aqueous self-assembling peptide solution. The self-assembling peptide may be administered, applied, or injected in a solution that is substantially cell-free, or free of cells. In certain embodiments, the self-assembling peptide may be administered, applied, or injected in a solution that is cell-free or free of cells.

The self-assembling peptide may also be administered, applied, or injected in a solution that is substantially drug-free or free of drugs. In certain embodiments, the self-assembling peptide may be administered, applied, or injected in a solution that is drug-free or free of drugs. In certain other embodiments, the self-assembling peptide may be administered, applied, or injected in a solution that is substantially cell-free and substantially drug-free. In still further certain other embodiments, the self-assembling peptide may be administered, applied, or injected in a solution that is cell-free and drug free.

The self-assembling peptide solution may comprise, consist of, or consist essentially of the self-assembling peptide. The self-assembling peptide may be in a modified or unmodified form. By modified, it is meant that the self-assembling peptide may have one or more domains that comprise one or more amino acids that, when provided in solution by itself, would not self-assemble. By unmodified, it is meant that the self-assembling peptide may not have any other domains other than those that provide for self-assembly of the peptide. That is, an unmodified peptide consists of alternating hydrophobic and hydrophilic amino acids that may self-assemble into a beta-sheet, and a macroscopic structure, such as a hydrogel.

Through administration of the solution comprising the self-assembling peptide, a hydrogel barrier may be formed. The hydrogel barrier may be formed in the target area to treat the pulmonary bulla. The treatment may be provided by collapsing, occluding and/or sealing the pulmonary bulla, at least partially. This is accomplished through formation of the hydrogel barrier. Throughout this disclosure, reference to a hydrogel, may also refer to or be applicable to the hydrogel barrier.

In certain embodiments, it is desired to have the hydrogel bather that may provide an adequate or desired blockage or seal at the target area. The hydrogel barrier may have specific properties to achieve the adequate or desired blockage or seal. For example, the hydrogel barrier may have one or more predetermined properties, for example, mechanical strength (storage modulus), rigidity, viscosity, gelation kinetics, ionic strength, pH, or burst pressure (burst pressure tolerance). The properties may be adjusted or tailored based on the addition, to the self-assembling peptide or solution comprising the self-assembling peptide, of components disclosed herein in specific amounts and/or concentrations.

For example, related to treating a pulmonary bulla, it may be desired to provide a hydrogel barrier having a high mechanical strength, rigidity, and high burst pressure. It may also be desired to provide a hydrogel barrier that is quick to gel, i.e., the gelation kinetics are such that, upon administration, the hydrogel barrier is formed within a short amount of time to treat the pulmonary bulla and/or leakage. The short amount of time may be instantaneous or, for example, less than 5 minutes, less than 3 minutes, less than 2 minutes, less than 1 minute, or less than 30 seconds, or other times disclosed herein.

Administration of a solution may comprise, consist of, or consist essentially of administration of a solution comprising, consisting of, or consisting essentially of a self-assembling peptide comprising, consisting of, or consisting essentially of at least about 7 amino acids. Administration of a solution may comprise, consist of, or consist essentially of administration of a solution comprising, consisting of, or consisting essentially of a self-assembling peptide comprising, consisting of, or consisting essentially of between about 7 amino acids and 32 amino acids. Other peptides that do not comprise, consist of, or consist essentially of at least about 7 amino acids may be contemplated by this disclosure.

The self-assembling peptide may comprise, consist of, or consist essentially of between about 7 to about 32 amino acids. In some embodiments, the self-assembling peptide may comprise, consist of, or consist essentially between about 12 and about 16 amino acids.

By alternating, it is meant to include a series of three or more amino acids that alternate between a hydrophobic amino acid and a hydrophilic amino acid, and it need not include each and every amino acid in the peptide sequence alternating between a hydrophobic and a hydrophilic amino acid.

The methods of treating a pulmonary bulla may comprise administering a self-assembling peptide to a target area. The peptide may be administered as a hydrogel or form a hydrogel upon administration. The methods of treating a pulmonary bulla may comprise administering a solution comprising a self-assembling peptide to a target area. The The term "administering," is intended to include, but is not limited to, applying, introducing or injecting the self-assembling peptide, in one or more of various forms including, but not limited to, by itself, by way of solution, such as an aqueous solution, or by way of a composition, hydrogel, or scaffold, with or without additional components.

The method may comprise introducing a delivery device to a target area of the pulmonary bulla of the subject. The method may comprise introducing a delivery device comprising at least one of a syringe, tube, pipette, catheter, catheter syringe, or other needle-based device to the target area of a subject. The self-assembling peptide may be administered by way of a syringe, tube, pipette, catheter, catheter syringe, or other needle-based device to the target area of a subject. The gauge of the syringe needle may be selected to provide an adequate flow of a composition, a solution, a hydrogel, or a liquid from the syringe to the target area. The gauge of the syringe needle or other delivery device may also be based on the use of the delivery device to provide for a collapse of the bulla. Providing an adequate flow of a composition, a solution, a hydrogel, or a liquid from the syringe to the target area may be based in some embodiments on at least one of the amount of self-assembling peptide in a composition, peptide solution, or a hydrogel being administered, the concentration of the peptide solution, in the composition, or the hydrogel, the viscosity of the peptide solution, composition, or hydrogel, and other components included with the self-assembling peptide. The delivery device may be a conventional device or designed to accomplish at least one of to reach a specific target area, achieve a specific dosing regime, deliver a specific target volume, amount, or concentration, and deliver accurately to a target area.

The method of treating a pulmonary leakage may comprise positioning an end of the delivery device in the target area in which treatment of a pulmonary bulla is desired. The target area may be an area as described herein, such as a portion of a surgical site, or a site of a pulmonary bulla. The self-assembling peptide may be administered by way of a delivery device to the target area in which treatment of a bulla is desired. The self-assembling peptide may be administered in a solution by way of the delivery device to the target area. In some embodiments, the administration may occur topically, in that the delivery device is positioned in close proximity to the target area, bulla, and/or leakage to provide the solution comprising the self-assembling peptide to a surface of the target area or location of the bulla and/or leakage. In other embodiments, the administration may occur directly at the bulla and/or leakage, in that the delivery device is positioned at the target area, bulla, and/or leakage to provide the solution comprising the self-assembling peptide to, for example, directly to, the target area or location of the bulla and/or leakage. In other embodiments, the administration may occur into or through the bulla and/or leakage, to the target area, bulla, or leakage, to fill a predetermined volume of the target area with the solution comprising the self-assembling peptide. Administering the solution may comprise applying the solution topically to the target area. Administering the solution may comprise injecting the solution into the target area, with overflow to, for example, cover the target area topically.

The use of a delivery device may provide a more selective administration of the peptide to provide for a more accurate delivery to the target area. Selective administration of the peptide may allow for enhanced and more targeted delivery of the peptide solution, composition, or hydrogel such that is successfully and positioned in the desired location in an accurate manner. The selective administration may provide enhanced, targeted delivery that markedly improves the positioning and effectiveness of the treatment over use of another delivery device. Delivery devices that may be used in the systems, methods, and kits of the disclosure may include a syringe, tube, needle, pipette, syringe catheter, other needle-based device, or catheter.

Use of a delivery device, such as a catheter, may include use of accompanying devices, such as a guidewire used to guide the catheter into position, or an endoscope that may allow proper placement of a catheter or other device and visualization of the target area, and/or the path to the target area. The endoscope may be a tube that may comprise at least one of a light and a camera or other visualization device to allow images of the subject's body to be viewed. The guidewire or endoscope may be introduced into the subject, for example, by way of an incision in the skin. The endoscope may be introduced to the target area prior to introducing the delivery device to the target area.

The use of the delivery device, such as a syringe, tube, needle, pipette, syringe catheter, other needle-based device, catheter, or endoscope may require determining the diameter or size of the opening in which there is a target area, such that at least a portion of the syringe, tube, needle, pipette, syringe catheter, other needle-type device, catheter, or endoscope may enter the opening to administer the peptide, peptide solution, composition, or hydrogel to the target area.

In certain embodiments, the hydrogel may be formed in vitro and administered to the desired location in vivo. In certain examples, this location may be the target area. In other examples, this location may be upstream, downstream of the area, or substantially near the area. It may be desired to allow a migration of the hydrogel to the area in which it is desired to. Alternatively, another procedure may position the hydrogel in the area in which it is desired. The desired location or target area may be at least a portion of an area in which it is desired to treat a pulmonary bulla in a subject.

In certain aspects of the disclosure, the hydrogel may be formed in vivo. A solution comprising the self-assembling peptide, such as an aqueous solution, may be inserted to an in vivo location or area of a subject to treat the pulmonary bulla in a subject. In certain examples, the hydrogel may be formed in vivo at one location, and allowed to migrate to the area in which it is desired to promote or provide a treatment to the pulmonary bulla, for example, a blockage or an occlusion at or near the pulmonary bulla, in a subject. Alternatively, another procedure may place the hydrogel in the area in which it is desired to promote or provide treatment of the pulmonary bulla. The peptides of the present disclosure may be in the form of a powder, a solution, a gel, or the like. Since the self-assembling peptide gels in response to changes in solution pH and salt concentration, it can be distributed as a liquid that gels upon contact with a subject during application or administration.

In certain environments, the peptide solution may be a weak hydrogel and, as a result, it may be administered by way of a delivery device as described herein.

In accordance with some embodiments, the self-assembling peptides may be amphiphilic, alternating between hydrophobic amino acids and hydrophilic amino acids.

In accordance with one or more embodiments, a subject may be evaluated to determine a need to treat a pulmonary bulla in a subject. Once the evaluation has been completed, a peptide solution to administer to the subject may be prepared based on the evaluating step. In other embodiments, a peptide solution may be prepared without the step of evaluating.

In some embodiments, a biologically active agent may be used with the materials and methods of the present disclosure. A biologically active agent may comprise a compound, including a peptide, DNA sequence, chemical compound, or inorganic or organic compound that may impart some activity, regulation, modulation, or adjustment of a condition or other activity in a subject or in a laboratory setting. The biologically active agent may interact with another component to provide such activity. The biologically active agent may be referred to as a drug in accordance with some embodiments herein. In certain embodiments, one or more biologically active agents may be gradually released to the outside of the peptide system. For example, the one or more biologically active agents may be gradually released from the hydrogel. Both in vitro and in vivo testing has demonstrated this gradual release of a biologically active agent. The biologically active agent may be added to the self-assembling peptide solution or composition prior to administering to a subject, or may be administered in conjunction with the self-assembling peptide or separately from the self-assembling peptide to the subject. The one or more biologically active agents may be encapsulated within the system, for example, they may be encapsulated in the hydrogel, solution, composition, or nanofibers.

This disclosure relates to aqueous solutions, hydrogels, scaffolds, compositions and membranes comprising self-assembling peptides, sometimes referred to as self-assembling oligopeptides. The self-assembling peptides may exhibit a beta-sheet structure in aqueous solution in the presence of physiological pH and/or cation and/or anions, such as a monovalent cation and/or monovalent anion, or other conditions applicable to a surgical site or at or near the site of a pulmonary bulla. The peptides may be amphiphilic and alternate between a hydrophobic amino acid and a hydrophilic amino acid. In certain embodiments, the peptide may comprise a first portion that may be amphiphilic, alternating between a hydrophobic amino acid and a hydrophilic amino acid, and another portion or region that is not amphiphilic.

The peptides may be generally stable in aqueous solutions and self-assemble into large, macroscopic structures, scaffolds, or matrices when exposed to selected conditions. The conditions may be physiological conditions, neutral pH, selected concentrations of salts, buffer solutions, or physiological levels of salt. Once the hydrogel is formed it may not decompose, or may decompose or biodegrade after a period of time. The rate of decomposition may be based at least in part on at least one of the amino acid sequence and conditions of its surroundings. The rate of decomposition may be related to the rate of healing or growth at the target site, so as to provide suitable treatment of the pulmonary bulla.

By "macroscopic" it is meant as having dimensions large enough to be visible under magnification of 10-fold or less. In preferred embodiments, a macroscopic structure is visible to the naked eye. A macroscopic structure may be transparent and may be two-dimensional, or three-dimensional. Typically each dimension is at least 10 µm, in size. In certain embodiments, at least two dimensions are at least 100 µm, or at least 1000 µm in size. Frequently at least two dimensions are at least 1-10 mm in size, 10-100 mm in size, or more.

In certain embodiments, the size of the filaments may be about 10 nanometers (nm) to about 20 nm. The interfilament distance may be about 50 nm to about 80 nm.

The macroscopic structure may be a macroscopic scaffold. The macroscopic scaffold may consist essentially of a plurality of self-assembling peptides. Each of the self-assembling peptides may comprise, consist essentially of, or consist of between about 7 amino acids and about 32 amino acids in an effective amount that is capable of being positioned within a target area of a pulmonary system to prevent a pulmonary bulla. The self-assembling peptides of the scaffold may comprise between about 12 to about 16 amino acids. The self-assembling peptides of the scaffold may comprise between about 12 to about 16 amino acids that alternate between a hydrophobic amino acid and a hydrophilic amino acid. The self-assembling peptide may comprise, consist essentially of, or consist of (RADA)$_4$ (SEQ ID NO: 1), (IEIK)$_3$I (SEQ ID NO: 2), (KLDL)$_3$ (SEQ ID NO: 3).

"Physiological conditions" may occur in nature for a particular organism, cell system, or subject which may be in contrast to artificial laboratory conditions. The conditions may comprise one or more properties such as one or more particular properties or one or more ranges of properties. For example, the physiological conditions may include a temperature or range of temperatures, a pH or range of pH's, a pressure or range of pressures, and one or more concentrations of particular compounds, salts, and other components. The salts may comprise one or more of monovalent anions, monovalent cations, divalent anions, or monovalent cations.

In some examples, the physiological conditions may include a temperature in a range of about 20 to about 40 degrees Celsius. In some examples, the atmospheric pressure may be about 1 atm. The pH may be in the range of a neutral pH. For example, the pH may be in a range of about 6 to about 8. The physiological conditions may include cations and/or anions such as monovalent metal cations and/or monovalent anions that may induce membrane or hydrogel formation. These may include sodium chloride (NaCl). The physiological conditions may also include a glucose concentration, sucrose concentration, or other sugar concentration, of between about 1 mM and about 20 mM. The self-assembling peptide solution may comprise glucose, sucrose, or other sugar, or a sugar or sugar solution may be added to the self-assembling peptide solution.

In certain embodiments, the self-assembling peptides may be peptides of at least about 7 amino acids. In certain further embodiments, the self-assembling peptides may be peptides of at least about 7 amino acids to about 32 amino acids. In certain further embodiments, the self-assembling peptides may be peptides of between about 7 to about 17 amino acids. In certain other examples, the self-assembling peptides may be peptides of at least 8 amino acids, at least about 12 amino acids, or at least about 16 amino acids.

Both homogeneous and heterogeneous mixtures of peptides characterized by the above-mentioned properties may form stable macroscopic membranes, filaments, and hydrogels. Peptides which are self-complementary and self-compatible may form membranes, filaments, and hydrogels in a homogeneous mixture. Heterogeneous peptides, including those which cannot form membranes, filaments, and hydrogels in homogeneous solutions, which are complementary and/or structurally compatible with each other may also self-assemble into macroscopic membranes, filaments, and hydrogels.

The membranes, filaments, and hydrogels may be non-cytotoxic. The hydrogels of the present disclosure may be digested and metabolized in a subject. The hydrogels may be biodegraded in 30 days or less. They have a simple composition, are permeable, and are easy and relatively inexpensive to produce in large quantities. The membranes and filaments, hydrogels or scaffolds may also be produced and stored in a sterile condition. The optimal lengths for membrane formation may vary with at least one of the amino acid composition, solution conditions, and conditions at the target area.

The amino acids of the self-assembling or amphiphilic peptides may be selected from d-amino acids, l-amino acids, or combinations thereof. The hydrophobic amino acids may include Ala, Val, Ile, Met, Phe, Tyr, Trp, Ser, Thr and Gly. The hydrophilic amino acids may be basic amino acids, for example, Lys, Arg, His, Orn; acidic amino acids, for example, Glu, Asp; or amino acids which form hydrogen bonds, for example, Asn, Gln. Acidic and basic amino acids may be clustered on a peptide. The carboxyl and amino groups of the terminal residues may be protected or not protected. Membranes or hydrogels may be formed in a homogeneous mixture of self-complementary and self-compatible peptides or in a heterogeneous mixture of peptides which are complementary and structurally compatible to each other. Peptides fitting the above criteria may self-assemble into macroscopic membranes under suitable conditions, described herein.

In certain embodiments, about 8 to about 32 residues may be used in the self-assembling peptides, while in other embodiments self-assembling peptides may have about 7 to about 17 residues. The peptides may have a length of about 5 nm.

The peptides of the present disclosure may comprise, consist essentially of, or consist of peptides having the repeating sequence of arginine, alanine, aspartic acid and alanine (Arg-Ala-Asp-Ala (SEQ ID NO: 4) (RADA (SEQ ID NO: 4))).

Other peptide sequences may be represented by self-assembling peptides comprising, consisting essentially of, or consisting of the repeating sequence of isoleucine, glutamic acid, isoleucine and lysine (Ile-Glu-Ile-Lys (SEQ ID NO: 5) (IEIK (SEQ ID NO: 5)) Other peptide sequences may be represented by self-assembling peptides comprising, consisting essentially of, or consisting of the repeating sequence of lysine, leucine, aspartic acid, and leucine (Lys-Leu-Asp-Leu (SEQ ID NO: 6) (KLDL (SEQ ID NO: 6))). As specific examples of self-assembling peptides according to the invention there may be a self-assembling peptide referred to as "RADA16" having the sequence Arg-Ala-Asp-Ala-Arg-Ala-Asp-Ala-Arg-Ala-Asp-Ala-Arg-Ala-Asp-Ala (SEQ ID NO: 1) ((RADA)$_4$ (SEQ ID NO: 1)) (also referred to as "Puramatrix" throughout the disclosure), a self-assembling peptide referred to as "IEIK13" having the sequence Ile-Glu-Ile-Lys-Ile-Glu-Ile-Lys-Ile-Glu-Ile-Lys-Ile (SEQ ID NO: 2) ((IEIK)$_3$I (SEQ ID NO: 2)), or a self-assembling peptide referred to as "KLDL12" (which may also be referred to as "KLD12" throughout this disclosure) having the sequence Lys-Leu-Asp-Leu-Lys-Leu-Asp-Leu-Lys-Leu-Asp-Leu (SEQ ID NO: 3) ((KLDL)$_3$ (SEQ ID NO: 3)).

Each of the peptide sequences disclosed herein may provide for peptides comprising, consisting essentially of, and consisting of the amino acid sequences recited.

The present disclosure provides materials, methods, and kits for solutions, hydrogels, compositions, and scaffolds comprising, consisting essentially of, or consisting of the peptides recited herein.

A 1 weight per volume (w/v) percent aqueous (water) solution and a 2.5 w/v percent of (RADA)$_4$ (SEQ ID NO: 1) is available as the product PuraMatrix™ peptide hydrogel by 3-D Matrix Co., Ltd.

The self-assembly of the peptides may be attributable to hydrogen bonding and hydrophobic bonding between the peptide molecules by the amino acids composing the peptides.

The self-assembling peptides of the present disclosure may have a nanofiber diameter in a range of about 10 nm to about 20 nm and an average pore size is in a range of about 5 nm to about 200 nm. In certain embodiments, the nanofiber diameter, the pore size, and the nanofiber density may be controlled by at least one of the concentration of peptide solution used and the amount of peptide solution used, such as the volume of peptide solution.

As such, at least one of a specific concentration of peptide in solution and a specific amount of peptide solution to provide at least one of a desired nanofiber diameter, pore size, and density to adequately provide for treatment of a pulmonary bulla, for example, providing an occlusion or a collapse, may be selected. The specific concentration and specific amount of peptide solution may be referred to as an "effective concentration" and an "effective amount."

As used herein, an amount of a peptide, peptide solution or hydrogel effective to treat a pulmonary bulla in a subject, an "effective amount" or a "therapeutically effective amount" refers to an amount of the peptide, peptide solution, composition, or hydrogel, which is effective, upon single or multiple administration (application or injection) to a subject, in treating, or in curing, alleviating, relieving or improving a subject with a disorder beyond that expected in the absence of such treatment. This may include a particular concentration or range of concentrations of peptide in the peptide solution, composition, or hydrogel and additionally, or in the alternative, a particular volume or range of volumes of the peptide solution, composition, or hydrogel. The method of facilitating may comprise providing instructions to prepare at least one of the effective amount and the effective concentration.

The dosage, for example, volume or concentration, administered (for example, applied or injected) may vary depending upon the form of the peptide (for example, in a peptide solution, hydrogel, or in a dried form, such as a lyophilized form) and the route of administration utilized. The exact formulation, route of administration, volume, and concentration can be chosen in view of the subject's condition and in view of the particular target area or location that the peptide solution, hydrogel, or other form of peptide will be administered. Lower or higher doses than those recited herein may be used or required. Specific dosage and treatment regimens for any particular subject may depend upon a variety of factors, which may include the specific peptide or peptides employed, the dimension of the area that is being treated, the desired thickness of the resulting hydrogel that may be positioned in the desired target area, and the length of time of treatment. Other factors that may affect the specific dosage and treatment regimens include age, body weight, general health status, sex, time of administration, rate of degradation, the severity and course of the disease, condition or symptoms, and the judgment of the treating physician. In certain embodiments, the peptide solution may be administered in a single dose. In other embodiments, the peptide solution may be administered in more than one dose, or multiple doses. The peptide solution may be administered in at least two doses. The administration of the solution may be repeated until a volume of the target area is filled.

An effective amount and an effective concentration of the peptide solution may be selected to at least partially treat a pulmonary bulla, for example to promote or provide an occlusion or collapse of the bulla at or near a pulmonary bulla in a subject. In some embodiments, at least one of the effective amount and the effective concentration may be based in part on a dimension or diameter of the target area. In other embodiments, at least one of the effective amount and the effective concentration is based in part on the flow rate of one or more fluids at or near the target area. In still other embodiments, at least one of the effective amount and the effective concentration may be based in part on a dimension or diameter of the target area of the pulmonary bulla or the site of a surgery.

In yet other embodiments, at least one of the effective amount and the effective concentration may be based in part on at least one of a dimension or diameter of the target area, and the flow rate of one or more fluids at or near the target area, and a dimension or diameter of a target area of the pulmonary bulla or the site of a surgery.

The effective amount may include volumes of from about 0.1 milliliters (mL) to about 100 mL of a peptide solution. The effective amount may include volumes of from about 0.1 mL to about 10 mL of a peptide solution. The effective amount may include volumes of from about 0.1 to about 5 mL. In certain embodiments, the effective amount may be about 0.4 mL. In certain embodiments, the effective amount may be about 0.5 mL. In other embodiments, the effective amount may be about 1.0 mL. In yet other embodiments, the effective amount may be about 1.5 mL. In still yet other embodiments, the effective amount may be about 2.0 mL. In some other embodiments, the effective amount may be about 3.0 mL.

In certain embodiments, the effective amount may be approximately 0.1 mL per 1 $cm^2$ to approximately 5 mL per 1 $cm^2$ of target area. The effective amount may be about 0.1 mL per 1 $cm^2$ to about 3 ml per 1 $cm^2$. In certain embodiments, the effective amount may be approximately 1 mL per 1 $cm^2$ of target area. This effective amount may be used related to a concentration, such as a 1.5 weight per volume percent or a 2.5 weight per volume percent of a peptide solution of the present disclosure.

The effective concentration may be, as described herein, an amount that may treat the pulmonary bulla. Various properties at or near the target site may contribute to the selection or determination of the effective concentration including at least one of a dimension or diameter of the target area, and the flow rate of one or more fluids at or near the target area.

The effective concentration may include peptide concentrations in the solution in a range of about 0.1 weight per volume (w/v) percent to about 10 w/v percent. The effective concentration may include peptide concentrations in the solution in a range of about 0.1 w/v percent to about 3.5 w/v percent. In certain embodiments, the effective concentration may be about 1 w/v percent. In certain other embodiments, the effective concentration may be about 1.5 w/v percent. In other embodiments, the effective concentration may be about 2.5 w/v percent. In yet other embodiments, the effective concentration may be about 3.0 w/v percent.

In certain embodiments, a peptide solution having a higher concentration of peptide may provide for a more effective hydrogel that has the ability to stay in place and provide effective treatment. For purposes of delivering the peptide solution, higher concentrations of peptide solutions may become too viscous to allow for effective and selective administration of the solution. It is possible that if a high enough concentration is not selected, the hydrogel may not be effective in the target area for the desired period of time.

The effective concentration may be selected to provide for a solution that may be administered by injection or other means using a particular diameter or gauge catheter or needle.

Methods of the disclosure contemplate single as well as multiple administrations of a therapeutically effective amount of the peptides, compositions, peptide solutions, membranes, filaments, and hydrogels as described herein. Peptides as described herein may be administered at regular intervals, depending on the nature, severity and extent of the subject's condition. In some embodiments, a peptide, composition, peptide solution, membrane, filament, or hydrogel may be administered in a single administration. In some embodiments, a peptide, composition, peptide solution, or hydrogel described herein is administered in multiple administrations. In some embodiments, a therapeutically effective amount of a peptide, composition, peptide solution, membrane, filament, or hydrogel may be administered periodically at regular intervals. The regular intervals selected may be based on any one or more of the initial peptide concentration of the solution administered, the amount administered, and the degradation rate of the hydrogel formed. For example, after an initial administration, a follow-on administration may occur after, for example, 30 seconds, 1 minute, two minutes, 5 minutes, 10 minutes, 1 day, 2 days, 5 days, one week, two weeks, four weeks, six weeks, or eight weeks. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject. The predetermined intervals may be the same for each follow-on administration, or they may be different. In some embodiments, a peptide, peptide solution, or hydrogel may be administered chronically at pre-determined intervals to maintain at least a partial treatment of a pulmonary bulla or bullae in a subject over the life of the subject. The pre-determined intervals may be the same for each follow-on administration, or they may be different. This may be dependent on whether the hydrogel formed from the previous administration is partially or totally disrupted or degraded. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging or visualizing the target area and the area surrounding the target area and ascertaining the needs based on the condition of the subject.

Administration of the self-assembling peptide may comprise applying a solution comprising the self-assembling peptide to the surface of the target area. In other embodiments, the solution may be applied through or into the target area. For example, a delivery device may be positioned within the bulla area so as to administer, for example, inject the solution into the bulla area, rather than applying the solution to the surface of the target area.

These administration procedures may be accomplished through appropriate positioning of the delivery device. As discussed above, the delivery device may be a syringe The syringe may have a particular gauge in order to allow proper flow of the solution onto or into the target area in order to achieve treatment of the pulmonary bulla.

Further procedures regarding treatment may comprise administering a salt solution to the target area subsequent to applying the solution comprising the self-assembling peptide. This may provide superior treatment of the pulmonary bulla due to increase in the mechanical strength of the resulting hydrogel barrier, for example, increased storage modulus of the resulting hydrogel barrier as compared to a hydrogel barrier that does not include further treatment with a salt solution.

The self-assembling peptides of the present disclosure, such as RADA16, may be peptide sequences that lack a distinct physiologically or biologically active motif or sequence, and therefore may not impair intrinsic cell function. Physiologically active motifs may control numerous intracellular phenomena such as transcription, and the presence of physiologically active motifs may lead to phosphorylation of intracytoplasmic or cell surface proteins by enzymes that recognize the motifs. When a physiologically active motif is present in a peptide, transcription of proteins with various functions may be activated or suppressed. The self-assembling peptides, of the present disclosure may lack such physiologically active motifs and therefore do not carry this risk.

A sugar may be added to the self-assembling peptide solution to improve the osmotic pressure of the solution from hypotonicity to isotonicity without reducing the treatment of the pulmonary bulla, thereby allowing the biological safety to be increased. In certain examples, the sugar may be sucrose or glucose.

The optimal lengths for membrane formation may vary with the amino acid composition. A stabilization factor contemplated by the peptides of the present disclosure is that complementary peptides maintain a constant distance between the peptide backbones. Peptides which can maintain a constant distance upon pairing are referred to herein as structurally compatible. The interpeptide distance can be calculated for each ionized or hydrogen bonding pair by taking the sum of the number of unbranched atoms on the side-chains of each amino acid in the pair. For example, lysine has 5 and glutamic acid has 4 unbranched atoms on its side-chains, respectively. The peptides can be chemically synthesized or they can be purified from natural and recombinant sources. Using chemically synthesized peptides may allow the peptide solutions to be deficient in unidentified components such as unidentified components derived from the extracellular matrix of another animal or microorganism. This property therefore may eliminate concerns of infection, including risk of viral infection compared to conventional tissue-derived biomaterials. This may eliminate concerns of infection including infections such as bovine spongiform encephalopathy (BSE), making the peptide highly safe for treatment of pulmonary bulla.

The initial concentration of the peptide may be a factor in the size and thickness of the membrane, hydrogel, or scaffold formed. In general, the higher the peptide concentration, the higher the extent of membrane or hydrogel formation. Hydrogels, or scaffolds formed at higher initial peptide concentrations (about 10 mg/ml) (about 1.0 w/v percent) may be thicker and thus, likely to be stronger.

Formation of the, membranes, hydrogels, compositions, or scaffolds may be very fast, on the order of a few seconds or a few minutes. The formation of the membranes or hydrogels may be irreversible. In certain embodiments, the formation may be reversible. The hydrogel may form instantaneously upon administration to a target area. The formation of the hydrogel may occur within about one to two minutes of administration. In other examples, the formation of the hydrogel may occur within about three to four minutes of administration. In certain embodiments the time it takes to form the hydrogel may be based at least in part on one or more of the concentration of the peptide solution, the volume of peptide solution applied, and the conditions at the area of application or injection (for example, the concentration of monovalent metal cations and/or anions at the area of application, the pH of the area, and the presence of one or more fluids at or near the area, additional components added to the solution prior to or subsequent to administration to the target area). The process may be unaffected by pH of less than or equal to 12, and by temperature. The membranes or hydrogels may form at temperatures in the range of 1 to 99 degrees Celsius.

The hydrogels may remain in position at the target area for a period of time sufficient to provide a desired effect using the methods and kits of the present disclosure. The desired effect using the materials, compositions, methods and kits of the present disclosure may be to treat areas or to assist in healing of areas in which a surgical procedure at or near the site of a surgery was performed or the site of the pulmonary bulla. For example, the desired effect using the materials, compositions, methods and kits of the present disclosure may be to treat areas or to assist in healing of areas in which a pulmonary surgery is performed.

The materials and methods of the present disclosure, including use of a solution, hydrogel, composition, or membrane comprising a self-assembling peptide as described herein to treat a pulmonary bulla, are provided in order to produce a hydrogel bather in a target area of the pulmonary bulla. A property of the hydrogel barrier that may determine the adequacy of success of the treatment is burst pressure, or burst pressure tolerance. Burst pressure may refer to the pressure at which the hydrogel barrier will fail. For example, this may be the pressure at which the hydrogel barrier no longer operates as desired to provide a suitable treatment to the target area. The burst pressure may be the pressure at which the blockage or occlusion provided by the hydrogel barrier allows air to pass through.

In some embodiments, it may be desirable to provide, through use of the materials and methods of the disclosure, a burst pressure that is similar to or higher than that which is achieved with normal tissue (for example, undamaged tissue or tissue without a leakage present). It may be desirable to provide, through use of the materials and methods of the disclosure, a burst pressure that is similar to the pressures exhibited through ordinary or average lung function. For normal, healthy tissue, a burst pressure of about 20 to about 30 cmH$_2$O may be generally observed.

In certain embodiments, a burst pressure of 35 cm H$_2$O or higher is a desirable or acceptable burst pressure for the hydrogel barrier for treating a pulmonary bulla. In certain embodiments, the burst pressure may increase after administration of the solution comprising the self-assembling peptide. For example, there may be an increase in burst pressure from one minute to two minutes, to 10 minutes. In some embodiments, it may be desired to have a burst pressure of at least 35 cm H$_2$O at between about 0 and 1 minute, 1 minutes to 2 minutes, or 2 minutes to five minutes. In certain embodiments, the burst pressure of at least 35 cm H$_2$O may be achieved in a time period suitable to allow treatment of the pulmonary bulla. The time period may also be suitable for appropriate treatment by the clinician. The burst pressure of at least 35 cm H$_2$O may be achieved in less than about 5 minutes, less than about 3 minutes, less than about 2 minutes, less than about 1 minute, or less than about 30 seconds.

There is an effect of gelation time, post-application. The burst pressure increases with increasing time, between 1 minute, 2 minutes, and 10 minutes. Two minutes may be preferable for providing seal. The hydrogel barrier may be suitable to provide an effective burst pressure of at least 35 cm H$_2$O, regardless of the size of the target area. For example, defects created by puncturing a surface with a 14 g, 16 g, 18 g, or 22 g needle does not dramatically effect burst pressure 35 cm H$_2$O.

The period of time that the membranes or hydrogels may remain at the desired area may be for about 10 minutes. In certain examples, it may remain at the desired area for about 35 minutes. In certain further examples, it may remain at the desired area for one or more days, up to one or more weeks. In other examples, it may remain at the desired area for up to 30 days, or more. It may remain at the desired area indefinitely. In other examples, it may remain at the desired area for a longer period of time, until it is naturally degraded or intentionally removed. If the hydrogel naturally degrades over a period of time, subsequent application or injection of the hydrogel to the same or different location may be performed.

In certain embodiments, the self-assembling peptide may be prepared with one or more components that may provide for enhanced effectiveness of the self-assembling peptide or may provide another action, treatment, therapy, or otherwise interact with one or more components of the subject. The one or more other components may provide for higher mechanical strength, as measured by storage modulus, G' and improved gelation kinetics, for example, faster gelation into a hydrogel or hydrogel barrier.

For example, the pH of the self-assembling peptide, for example, in the form of a self-assembling peptide solution or composition, may be adjusted. The pH of the self-assembling peptide, in the form of a self-assembling peptide solution or composition, may be increased or decreased. This may be done by adjusting the pH of the self-assembling peptide solution, by way of addition of a pH adjuster. The pH adjuster may be, for example, salts, a salt solution or buffer solution. The pH adjuster may be selected based on the amino acid sequence of the self-assembling peptide, the type of salt or salts, the concentration of the one or more salts, and the pH of the pH adjuster. In certain embodiments, the pH of the solution comprising the self-assembling peptide is between about 2.5 to about 4.0.

The solutions and compositions comprising a self-assembling peptides that are provide by this disclosure may be prepared with additional components, for example, one or more salts. Preparation of the solution may comprise adding the self-assembling peptide, for example, in the form of a peptide powder or a peptide solution, to a salt solution. In other embodiments, the preparation of the solution may comprise adding a salt or a salt solution to a self-assembling peptide, in the form of a peptide powder or a peptide solution. In other embodiments, the preparation of the solution comprising the self-assembling peptide comprises adding water to a peptide powder of the self-assembling peptide to provide an aqueous peptide solution. The water may be deionized water or any purified water suitable for peptide solution preparation. The water may be medical device acceptable grade or pharmaceutically acceptable grade. The peptide powder and water may be optionally mixed. A salt or salt solution may then be added to the aqueous peptide solution. The salt or salt solution and the aqueous peptide solution may then be mixed.

Salt solutions may be provided to use in the solution comprising the self-assembling peptide, to add to the solution comprising the self-assembling peptide, or to add to the hydrogel or composition comprising the self-assembling peptide. The salt solutions may be provided with specific anions and cations, and at specific concentrations in order to impart a desired property to the solution comprising the self-assembling peptide, or the resulting hydrogel, or hydrogel bather. For example the salt solution may be provided to have a mechanical strength (storage modulus), rigidity, viscosity, gelation kinetics, ionic strength, pH, or burst pressure (burst pressure tolerance).

Salt solutions may comprise monovalent and/or divalent cations and/or anions. The salt solution may comprise at least one cation selected from the group consisting of ammonium, iron, magnesium, potassium, pyrimidium, quaternary ammonium, sodium, potassium, and calcium. The salt solution may comprise at least one anion selected from the group consisting of chloride, sulfate, acetate, carbonate, chloride, citrate, cyanide, fluoride, sulfate, nitrate, nitrite, and phosphate.

In some embodiments, the salt solution comprises at least one of calcium chloride, sodium chloride, and potassium chloride.

In certain embodiments, the solution comprising the self-assembling peptide may comprise (RADA)$_4$ (SEQ ID NO: 1) at a concentration of about 0.5 w/v percent. This solution may further comprise a calcium chloride concentration of about 0.125 M. This solution may further provide for a storage modulus of about 25 Pa.

In certain embodiments, the solution comprising the self-assembling peptide may comprise (RADA)$_4$ (SEQ ID NO: 1) at a concentration of about 0.5 w/v percent. This solution may further comprise a calcium chloride concentration of about 0.250 M. This solution may further provide for a storage modulus of about 44 Pa.

In certain embodiments, the solution comprising the self-assembling peptide may comprise (RADA)$_4$ (SEQ ID NO:

1) at a concentration of about 0.5 w/v percent. This solution may further comprise a calcium chloride concentration of about 0.500 M. This solution may further provide for a storage modulus of about 52 Pa.

In certain embodiments, the solution comprising the self-assembling peptide may comprise (RADA)$_4$ (SEQ ID NO: 1) at a concentration of about 2.5 w/v percent. This solution may further comprise a calcium chloride concentration of about 0.125 M. This solution may further provide for a storage modulus of about 600 Pa.

In embodiments, the solution comprising the self-assembling peptide may have a concentration of salt of between about 0.005 M and about 1 M. In certain embodiments, the solution comprising the self-assembling peptide may have a concentration of salt of between about 0.125 M and about 0.500 M. In certain embodiments, the solution comprising the self-assembling peptide may have a concentration of salt of between of about 0.25 M.

In embodiments, the solution comprising the self-assembling peptide may comprise or may have added to it an isotonic solution. The isotonic solution may be relative to a subject, for example bodily fluids of the subject or the local physiological conditions at the target area. The isotonic solution may comprise at least one of sodium chloride, potassium chloride calcium chloride and water. The solution may contain hydrochloric acid or sodium hydroxide, which may be used for pH adjustment. To prepare this solution 8.6 g NaCl, 0.3 g KCl, 0.33 g CaCl$_2$ may be dissolved in one liter of distilled water. The pH of this solution may be about 5.4. The pH of the solution may be adjusted with an acid or a base, or a pH adjuster. The pH adjuster may be sodium bicarbonate. The solution may be referred to as Ringer's solution.

In embodiments, the solution comprising the self-assembling peptide may comprise or may have added to it a contrast agent. The contrast agent may be utilized for visualization of the solution comprising the self-assembling peptide or the hydrogel or hydrogel barrier. The contrast agent may provide for or assure a practitioner the location of the solution comprising the self-assembling peptide or the hydrogel or hydrogel barrier. The contrast agent may comprise at least one of sulfate ions and sodium ions.

In embodiments, the properties of various self-assembling peptides, including but not limited to (RADA)$_4$ (SEQ ID NO: 1), (IEIK)$_3$I (SEQ ID NO: 2), (KLDL)$_3$ (SEQ ID NO: 3) may be enhanced by maintaining their salt concentration at less than their critical ionic strength level before they begin to precipitate. The critical ionic strength level of salts varies depending on the intrinsic amino acid characteristics and composition in each peptide. The peptides may be dissolved in water with various salts instead of pure water to maintain their salt ionic strength at less than their critical ionic strength level before they begin to precipitate.

This may beneficially impart relatively stiffer properties or higher mechanical strength to the self-assembling peptide solution and hydrogels at various salt concentration rendering them suitable for a broader range of applications in comparison to peptide hydrogels maintained at a zero salt concentration level. This may also beneficially impart a fast gelation kinetics from peptide solution to peptide hydrogels upon environmental salt ionic strength change to over their critical ionic strength before precipitation such as physiological ionic strength, which may occur when the peptide solution is administered to physiological conditions, for example, a target area of the subject.

In accordance with one or more aspects, the properties of various peptide hydrogels, including but not limited to (RADA)$_4$ (SEQ ID NO: 1), (IEIK)$_3$I (SEQ ID NO: 2), (KLDL)$_3$ (SEQ ID NO: 3), may be enhanced by maintaining their pH level at an elevated value of about 3.5 or less and at the same time, their salt concentration at less than their critical ionic strength level before they precipitate.

In some embodiments, the solution comprising (RADA)$_4$ (SEQ ID NO: 1) has a pH of about 3.5. In some embodiments, the solution comprising (KLDL)$_3$ (SEQ ID NO: 3), has a pH of about 3.5. In some embodiments, the solution comprising (IEIK)$_3$I (SEQ ID NO: 2), has a pH of about 3.7.

In some embodiments, a buffer, such as a buffer solution may be added to the self-assembling peptide solution or the self-assembling peptide.

A buffer may be an aqueous solution consisting of a mixture of a weak acid and its conjugate base, or vice versa. The pH of the buffer changes very little when a small or moderate amount of strong acid or base is added to it and thus it is used to prevent changes in the pH of a solution. Buffer solutions are used as a means of keeping pH at a nearly constant value in a wide variety of chemical applications, and is applicable to the self-assembling peptides and self-assembling peptide solutions and compositions disclosed herein.

A buffer may comprise at least two salts. A buffer may have a pH of about 7.4, such as PBS buffer (phosphate buffered saline). A buffer may have a pH of about 7.2, such as DMEM buffer. In some embodiments, the buffer may be an alkali buffer.

In some embodiments, a solution or composition of the self-assembling peptide may be buffered with about 0.15 M of at least one of sodium chloride, potassium chloride, and calcium chloride. When the self-assembling peptide is (RADA)$_4$ (SEQ ID NO: 1), the buffer may comprise between about 0.6 and about 1.2 M of a salt. When the self-assembling peptide is (IEIK)$_3$I (SEQ ID NO: 2), the buffer may comprise between about 0.6 and about 1.2 M of a salt. When the self-assembling peptide is (RADA)$_4$ (SEQ ID NO: 1), the buffer may comprise between about 0.02 and about 0.04 M of a salt. When the self-assembling peptide is (KLDL)$_3$ (SEQ ID NO: 3), the buffer may comprise between about 0.1 and about 0.4 M of a salt.

In certain embodiments, methods of treatment are provided that further comprise selecting a salt to provide a predetermined mechanical strength to the solution. The method may further comprise selecting the concentration of the salt to provide the predetermined mechanical strength to the solution. The method may comprise selecting a salt to provide a predetermined ionic strength to the solution. The method may further comprise selecting the concentration of the salt to provide the predetermined ionic strength to the solution. The method may comprise selecting a salt to provide a predetermined pH to the solution. The method may further comprise selecting the concentration of the salt to provide the predetermined pH to the solution.

Additional peptides comprising one or more biologically or physiologically active amino acid sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately.

The peptide, peptide solution, or hydrogel may comprise small molecular drugs to treat the subject or to prevent hemolysis, inflammation, and infection. The small molecular drugs may be selected from the group consisting of glucose, saccharose, purified saccharose, lactose, maltose, trehalose, dextran, iodine, lysozyme chloride, dimethylisoprpylazulene, tretinoin, tocoferil, povidone iodine, alprostadil alfadex, anise alcohol, isoamyl salicylate, α,α-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate. Other small molecular drugs may be contemplated. Protein-based drugs may be included as a component to be administered, and may include erythropoietin, tissue type plasminogen activator, synthetic hemoglobin and insulin.

A component may be included to protect the self-assembling peptide, the solution comprising the self-assembling peptide, or the composition against rapid or immediate formation into a hydrogel. This may include an encapsulated delivery system that may degrade over time to allow a controlled time release of the peptide solution into the target area to form the hydrogel over a desired, predetermined period of time. Biodegradable, biocompatible polymers may be used, such as ethylene vinyl acetate, polyanhydrides, polyglycolic acid, collagen, polyorthoesters, and polylactic acid.

Any of the components described herein may be included in the self-assembling peptide, the solution comprising the self-assembling peptide, the composition, or kit or may be administered separate from the self-assembling peptide, the solution comprising the self-assembling peptide, the composition, or the kit. Additionally, any of the methods and methods of facilitating provided herein may be performed by one or more parties.

A peptide, peptide solution, composition or hydrogel of the disclosure may be provided in a kit for treating a pulmonary bulla. The kit may be for treating a pulmonary bulla in a subject. Instructions for administering solution self-assembling peptide to a target area of a subject pulmonary bulla may also be provided in the kit. The self-assembling peptide may comprise between about 7 amino acids and about 32 amino acids in an effective amount to form a hydrogel barrier to allow treatment of the pulmonary bulla. In some embodiments, the self-assembling peptide may comprise, consist of, or consist essentially between about 12 and about 16 amino acids. The self-assembling peptide may comprise, consist essentially of, or consist of $(RADA)_4$ (SEQ ID NO: 1), $(IEIK)_3I$ (SEQ ID NO: 2), $(KLDL)_3$ (SEQ ID NO: 3). The concentrations of the self-assembling peptide in solution may be any of the concentrations disclosed herein.

The instructions for administering the solution may comprise methods for administering the peptide, peptide solution, or hydrogel provided herein, for example, by a route of administration described herein, at a dose, volume or concentration, or administration schedule. The peptide may be amphiphilic and at least a portion of the peptide may alternate between a hydrophobic amino acid and a hydrophilic amino acid.

The kit may provide the self-assembling peptide as one of a solution comprising a self-assembling peptide and a powder to be prepared as a solution comprising a self-assembling peptide. Instructions for preparing a solution comprising a self-assembling peptide having an effective concentration to form a hydrogel barrier under physiological conditions to allow treatment of the pulmonary bulla may also be provided.

The kit may also comprise informational material. The informational material may be descriptive, instructional, marketing or other material that relates to the methods described herein. In one embodiment, the informational material may include information about production of the peptide, peptide solution, or hydrogel disclosed herein, physical properties of the peptide, composition, peptide solution or hydrogel, concentration, volume, size, dimensions, date of expiration, and batch or production site.

The kit may also optionally include a device or materials to allow for administration of the peptide or peptide solution to the desired area. For example, a syringe, pipette, catheter, or other needle-based device may be included in the kit. Additionally, or alternatively, the kit may include a guidewire, endoscope, or other accompanying equipment to provide selective administration of the peptide solution to the target area.

The kit may comprise in addition to or in the alternative, other components or ingredients, such as components that may aid in positioning of the peptide solution, hydrogel or scaffold. Instructions may be provided in the kit to combine a sufficient quantity or volume of the peptide solution with a sucrose solution, that may or may not be provided with the kit. Instructions may be provided for diluting the peptide solution to administer an effective concentration of the solution to the target area. The instruction may describe diluting the peptide solution with a diluent or solvent. The diluent or solvent may be water. Instructions may further be provided for determining at least one of the effective concentration of the solution and the effective amount of the solution to the target area. This may be based on various parameters discussed herein, and may include the diameter of the lesion or site of a pulmonary bulla or wound at the target area.

Other components or ingredients may be included in the kit, in the same or different compositions or containers than the peptide, peptide solutions, or hydrogel. The one or more components that may include components that may provide for enhanced effectiveness of the self-assembling peptide or may provide another action, treatment, therapy, or otherwise interact with one or more components of the subject. For example, additional peptides comprising one or more biologically or physiologically active sequences or motifs may be included as one of the components along with the self-assembling peptide. Other components may include biologically active compounds such as a drug or other treatment that may provide some benefit to the subject. For example, a cancer treating drug or anticancer drug may be administered with the self-assembling peptide, or may be administered separately. The peptide, peptide solution, or hydrogel may comprise small molecular drugs to treat the subject or to prevent hemolysis, inflammation, and infection, as disclosed herein. A sugar solution such as a sucrose solution may be provided with the kit. The sucrose solution may be a 20% sucrose solution.

Other components which are disclosed herein throughout this disclosure may also be included in the kit. For example, the kit may further comprise salt solutions separate, or in combination with the self-assembling peptide. The kit may further comprise, for example, a sugar or sugar solution, for example, sucrose, that is provided separately from the self-assembling peptide or together with the self-assembling peptide. Instructions may be provided for combining a salt solution and one of the solution comprising the self-assembling peptide, or the peptide powder. The kit may further comprise an isotonic solution or contrast agent to be added to the self-assembling peptide solution or powder, or as part of the self-assembling peptide solution.

In some embodiments, a component of the kit is stored in a sealed vial, for example, with a rubber or silicone closure (for example, a polybutadiene or polyisoprene closure). In some embodiments, a component of the kit is stored under inert conditions (for example, under nitrogen or another inert gas such as argon). In some embodiments, a component of the kit is stored under anhydrous conditions (for example, with a desiccant). In some embodiments, a component of the kit is stored in a light blocking container such as an amber vial.

As part of the kit or separate from a kit, syringes or pipettes may be pre-filled with a peptide, peptide solution, or hydrogel as disclosed herein. Methods to instruct a user to supply a self-assembling peptide solution to a syringe or pipette, with or without the use of other devices, and administering it to the target area through the syringe or pipette, with or without the use of other devices, is provided. Other devices may include, for example, a catheter with or without a guidewire.

The self-assembling peptide of the kit may be any peptide provided in this disclosure, and any components described in this disclosure, for example, various salts, pH adjusters, buffers, alkali buffers may be provided in the kit, with the self-assembling peptide in the kit, or separately from the self-assembling peptide in the kit.

In embodiments, compositions comprising a self-assembling peptide comprising between about 7 amino acids and 32 amino acids in an effective amount and in an effective concentration is provided for use in forming a hydrogel bather under physiological conditions to treat a pulmonary bulla. The hydrogel bather of the composition may provide a burst pressure tolerance of at least 35 $H_2O$. The self-assembling peptide of the composition may be selected from the group consisting of $(RADA)_4$ (SEQ ID NO: 1), $(IEIK)_3I$ (SEQ ID NO: 2), and $(KLDL)_3$ (SEQ ID NO: 3). The concentration effective to allow treatment of the pulmonary bulla comprises a self-assembling peptide concentration in a range of about 0.1 weight per volume (w/v) percent to about 3 w/v percent. The composition may be substantially free of cells. The composition may be substantially free of drugs. The composition may further comprise any one or more of the components disclosed herein. For example, the composition may comprise any one or more of the cations, anions, salts, buffers, contrast agents, isotonic solutions, pH adjusters, and sugars disclosed herein, and at the various concentration disclosed herein. The compositions may have properties such as mechanical strength, pH, gelation kinetics, and ionic strength as disclosed herein. The compositions may be used in the treatment of pulmonary bulla, and may be treatments for a subject, such as a mammal or human.

Method of facilitating treatment of a pulmonary bulla in a subject may also be provided. The methods may comprise providing a solution comprising a self-assembling peptide comprising between about 7 amino acids to about 32 amino acids in an effective amount and in an effective concentration to form a hydrogel bather under physiological conditions to allow treatment of the pulmonary bulla; and providing instructions for administering the solution to a target area of the pulmonary system through introduction of the solution through a delivery device positioned in the pulmonary bulla.

The methods may further comprising providing instructions to visualize a region comprising at least a portion of the pulmonary bulla, as disclosed herein. Instructions may also be provided to visualize the region comprising at least a portion of the pulmonary bulla, wherein the instructions comprise at least one of identifying the target area of the pulmonary system; introducing the delivery device; positioning an end of the delivery device in the target area; administering the solution; removing the delivery device from the pulmonary bulla; and monitoring the pulmonary bulla after removing the delivery device. Instructions may be provided to visualize the region in a time period of about 1 minute to about 5 minutes subsequent the step of administering the solution. The method may further comprise providing instructions to prepare at least one of the effective amount and the effective concentration based in part on a dimension of the target area of the pulmonary bulla, as discussed in the disclosure.

The self-assembling peptide is selected from the group consisting of $(RADA)_4$ (SEQ ID NO: 1), $(IEIK)_3I$ (SEQ ID NO: 2), and $(KLDL)_3$ (SEQ ID NO: 3). The method may further comprise providing instructions to monitor the area surrounding the target area. The method may further comprise providing the solution and instructions for use after a surgical procedure. The method comprising providing a solution comprising a self-assembling peptide may comprise providing instructions for preparing a peptide solution, as disclosed herein, having an effective concentration to form a hydrogel barrier under physiological conditions to allow prevention of the pulmonary bulla.

EXAMPLES

Example 1: Impact of pH Level on Rheological Properties of Peptide Hydrogels

The effects of Dulbecco's modified Eagle's medium (DMEM) (pH 7.4) on the rheological properties of IEIK13, KLD12, and PuraMatrix® were evaluated on a rheometer (AR500, TA Instruments) with 40 mm plates. DMEM is generally a cell culture medium that contains 6.4 g/L of NaCl, 3.4 g/L $NaHCO_3$ (sodium bicarbonate), minor amounts of other salts, various amino acids, and 4.5 g/L of glucose. The pH level of DMEM is generally 7.2±0.2 and the osmolality is 335±30 mOsm/Kg $H_2O$; both measurements are close to human physiological fluids such as blood.

Peptide solutions (1%) were kept at 4° C. for at least 48 hours before testing. To perform the experiment, 1 mL of peptide solution was gently pipetted and placed on the plate of the rheometer. 2 mL of DMEM solution was gently added around the peptide solution. The peptide solution was treated with DMEM for two minutes, then the media was removed, and the plates were placed at a measuring geometry gap at around 450 μm. Measurements were performed at 37° C. after 2 min of relaxation time. Frequency tests were performed from 1 rad/s to 100 rad/s at 1 Pa of oscillation stress.

Figure 1B:
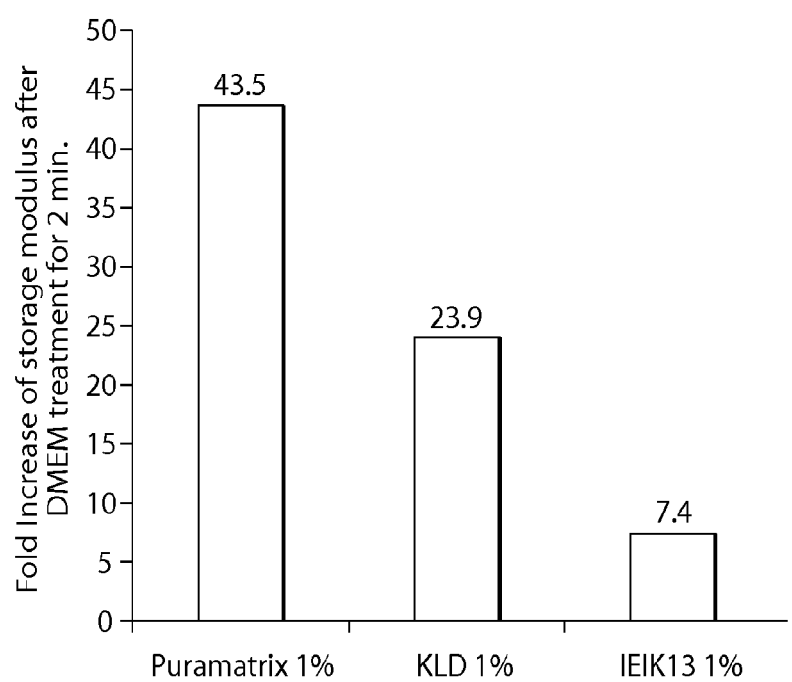

The rheological properties of the peptides (1%) were compared before and after DMEM treatment for 2 minutes, as shown in FIG. 1A. The fold increase of storage moduli after DMEM treatment for 2 minutes is shown in FIG. 1B. Each of the peptides showed large increases of storage moduli after DMEM treatment. The fold difference between storage moduli after DMEM treatment between PuraMatrix®, KLD12, and IEIK13 was relatively slight compared to that before DMEM treatment. Similarly, stiffer peptide solutions (i.e. IEIK13) showed lower-fold increase of storage modulus than weaker peptide solutions (i.e. PuraMatrix®) after DMEM treatment. This observation suggests that a critical intermolecular interaction arises after DMEM treatment, which determines the final stiffness after DMEM treatment.

Example 2: Optimization of pH Level of Peptide Solutions

To adjust the pH level of the peptide solutions by way of example, 0.1 N NaOH was added to 2 mL of 2.5% peptide solutions and their pH and appearance were measured. Results are shown in Table 1. Notably, a pH increase up to approximately 3.5 or less did not change the clear color of PuraMatrix®, IEIK13, and KLD12 solutions, while their apparent stiffness increased.

TABLE 1

Appearance of peptide solutions at various pH levels

| Peptides | 0.1N NaOH added in 2.5% solution (μL/mL) | Conc. (%) | Peptide solution pH | Appearance |
| --- | --- | --- | --- | --- |
| PuraMatrix ® | 0 | 2.5 | 2.2 | Clear, thick gel |
| | 50 | 2.38 | 2.3 | Clear, thick gel |
| | 100 | 2.27 | 2.4 | Clear, thick gel |
| | 150 | 2.17 | 2.7 | Clear, thick, stiffer gel |
| | 200 | 2.08 | 2.9 | Clear, thick, stiffer gel |
| | 250 | 2.0 | 3.2 | Clear, thick, stiffer gel |
| | 275 | 1.96 | 3.4 | Clear, thick, stiffer gel |
| | 300 | 1.92 | 3.6 | Slightly cloudy, brittle gel |
| | 350 | 1.85 | 4.5 | Cloudy, phase-separated |
| | | | 7.0 | Cloudy, phase-separated |
| IEIK13 | 0 | 2.5 | 1.8 | Clear, thick gel |
| | 50 | 2.38 | 2.1 | Clear, thick gel |
| | 100 | 2.27 | 2.2 | Clear, thick gel |
| | 150 | 2.17 | 2.7 | Clear, thick gel, stiffer gel |
| | 200 | 2.08 | 3.0 | Clear, thick gel, stiffer gel |
| | 250 | 2.0 | 3.3 | Clear, thick gel, stiffer gel |
| | 275 | 1.96 | 3.7 | Clear, thick, stiffer gel |
| | 300 | 1.92 | 4.0 | Slightly cloudy, brittle gel |
| | 350 | 1.85 | 4.5 | Cloudy, brittle gel |
| | 400 | 1.79 | 5.4 | Cloudy, phase-separated |
| | | | 7.0 | Cloudy, phase-separated |
| KLD12 | 0 | 2.5 | 2.1 | Clear, thick gel |
| | 50 | 2.38 | 2.4 | Clear, thick gel |
| | 100 | 2.27 | 2.6 | Clear, thick gel |
| | 150 | 2.17 | 2.9 | Clear, thick and stiffer gel |
| | 200 | 2.08 | 3.3 | Clear, thick and stiffer gel |
| | 225 | 2.04 | 3.6 | Clear, thick and stiffer gel |
| | 250 | 2.0 | 4.0 | Slightly cloudy, brittle gel |
| | 300 | 1.92 | 4.7 | Cloudy, brittle gel |
| | 350 | 1.85 | 5.2 | Cloudy, phase-separated |
| | | | 7.0 | Cloudy, phase-separated |

Example 3: Rheological Properties of pH Adjusted Peptide Solutions

Figure 2:
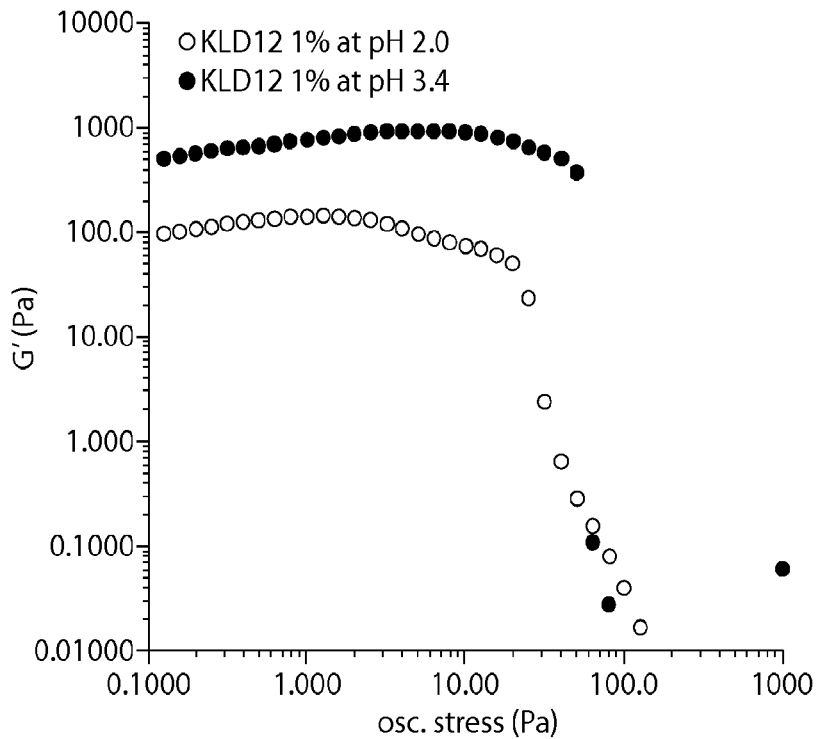
FIGS. 2-4 present data discussed in Example 3.
Figure 3:
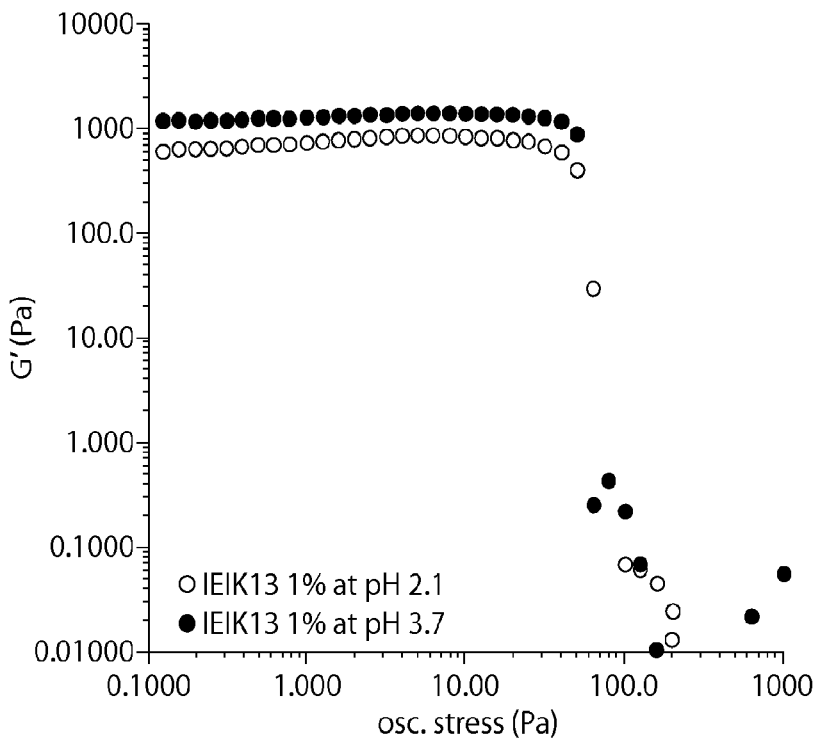
Figure 4:
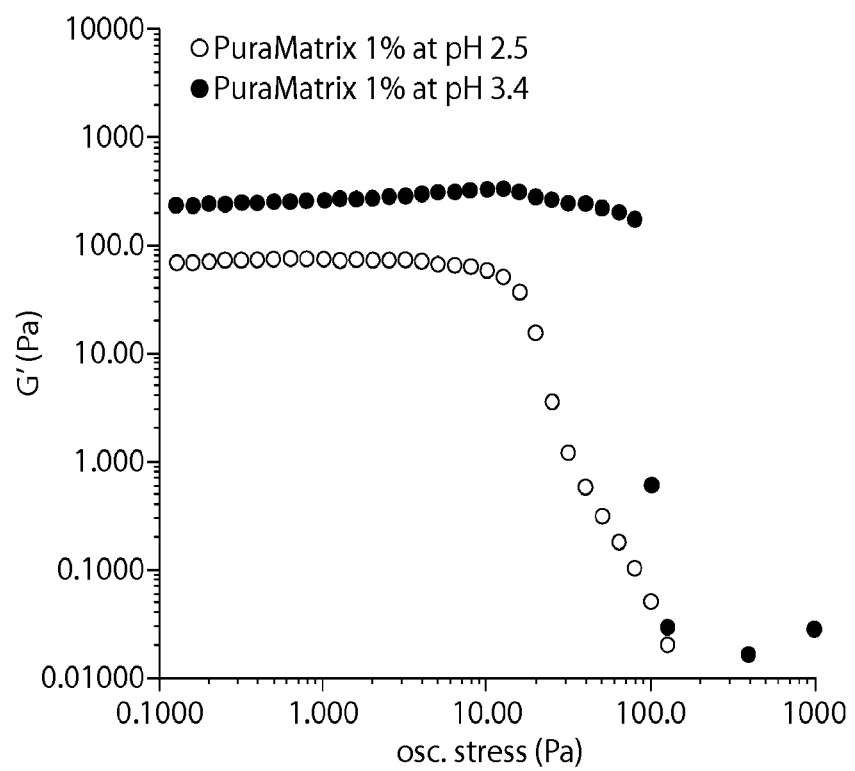
Figure 5A:
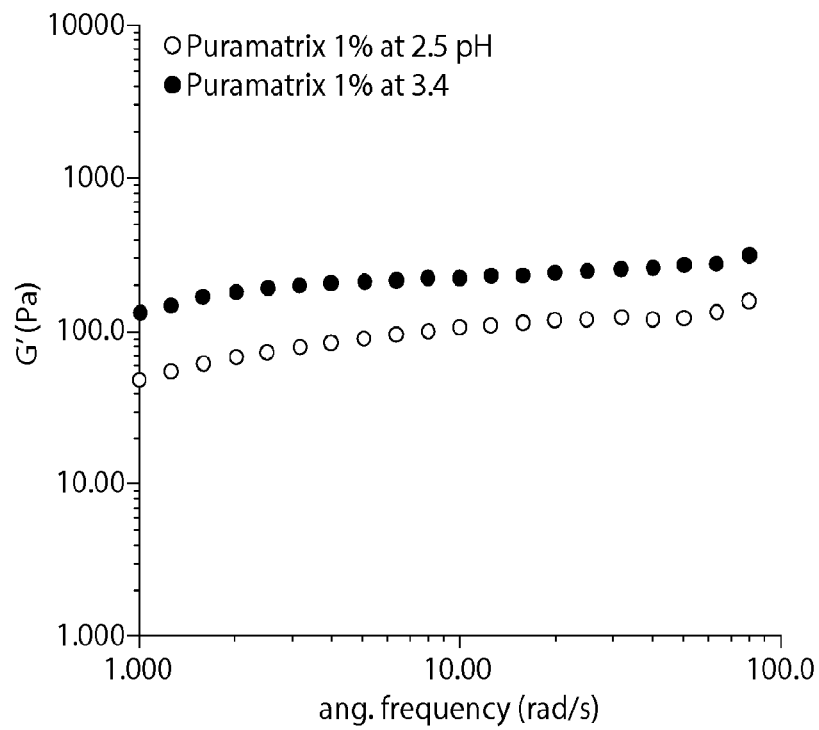
FIGS. 5A-5B present data discussed in Example 3.
Figure 5B:
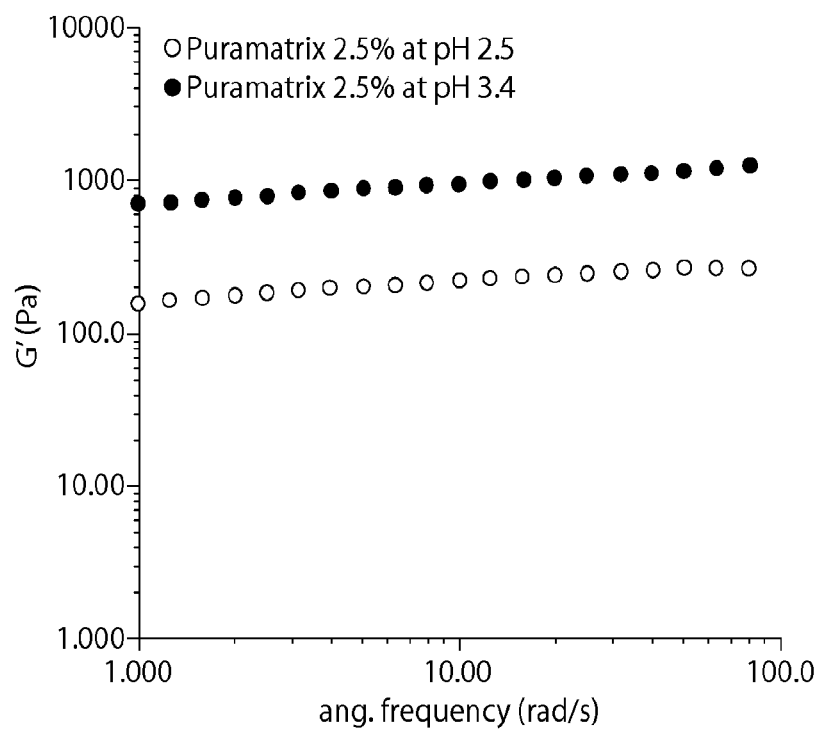

Based on the visual observation of the effect of pH level on the properties of the peptide solutions, the effect on the rheological properties of the peptide solutions after adjusting their pH level to 3.4 (PuraMatrix® and KLD12) or 3.7 (IEIK13) was evaluated. If the pH levels of peptide solutions are higher than 3.5 (PuraMatrix® and KLD12) or 3.7 (IEIK13), the peptide solution began phase separation becoming cloudy. The rheological properties of PuraMatrix®, KLD12 and IEIK13 solutions were higher at pH 3.4. The results are shown in FIG. 2 for KLD12 1%, FIG. 3 for IEIK13 1%, and FIGS. 4-5 for PuraMatrix® 1% and 2.5%, respectively. Stress sweep tests were performed at 10 rad/s. Frequency sweep tests were performed at 1 Pa.

Example 4: Further Rheological Properties of pH Adjusted Peptide Solutions

Figure 6A:
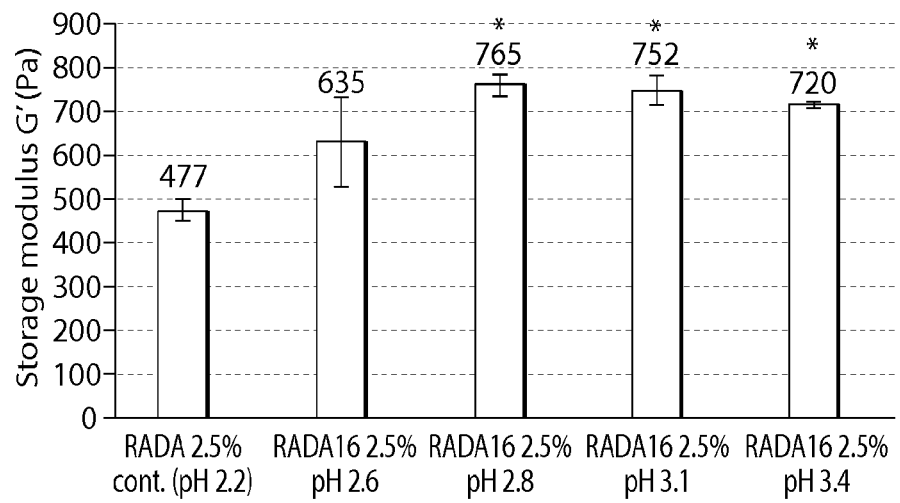
FIGS. 6A-6B present data discussed in Example 4.
Figure 6B:
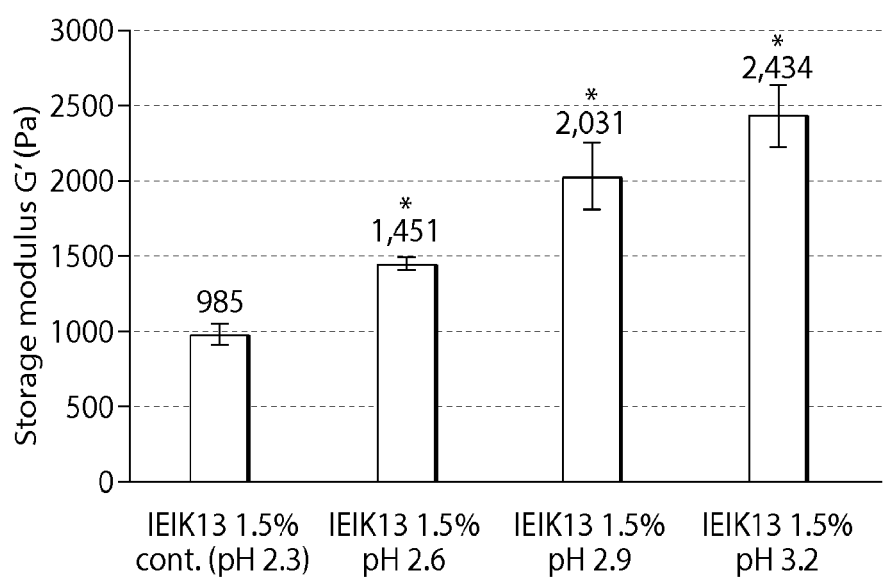

Based on the results of the effect on the rheological properties of the peptide solutions after adjusting their pH level to 3.4 (PuraMatrix® and KLD12) or 3.7 (IEIK13), the effect on the rheological properties of the peptide solutions at various pH levels was evaluated. The rheological property of PuraMatrix® and IEIK13 solutions increases with pH adjustment up to 3.4. The rheological properties of peptides were evaluated at various concentrations using a rheometer (DHR-1, TA Instruments) with 20 mm plates. The results are shown in FIG. 6A for PuraMatrix® 2.5% solution and FIG. 6B for IEIK13 1.5% solution, respectively. Frequency sweep tests were performed from 1 rad/sec to 10 rad/sec at 1 Pa and the storage modulus at 1 rad/sec was selected for data.

Figure 7A:
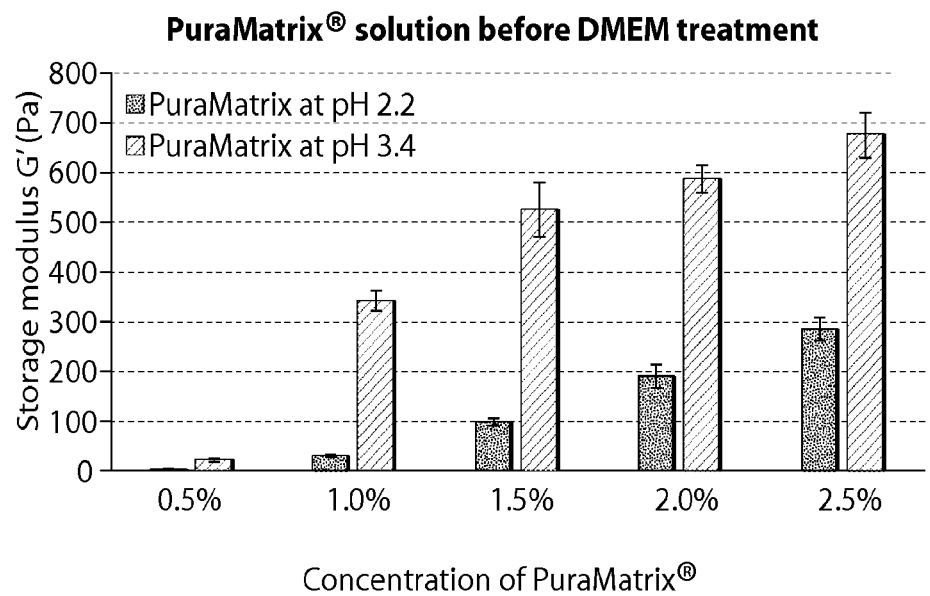
FIGS. 7A-7B present data discussed in Example 5.
Figure 7B:
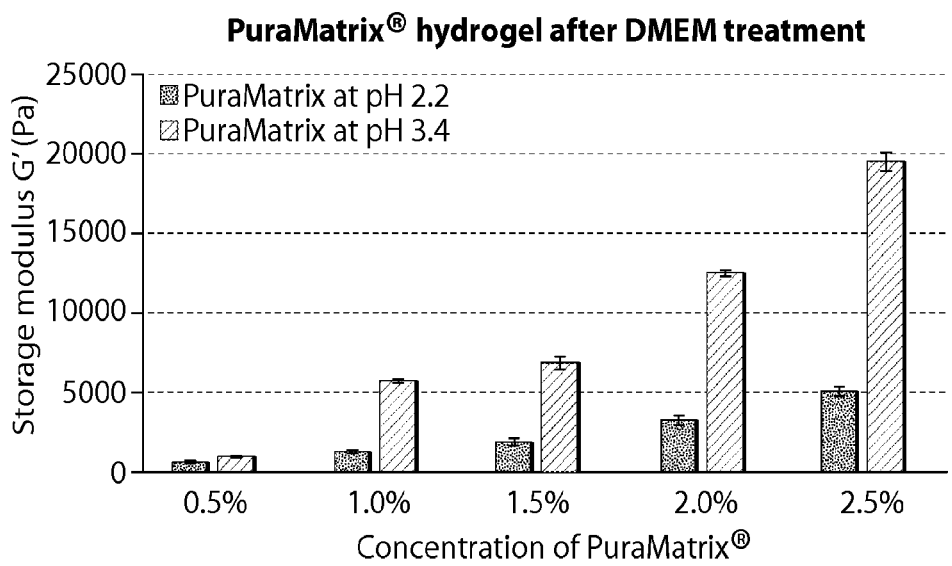
Figure 8A:
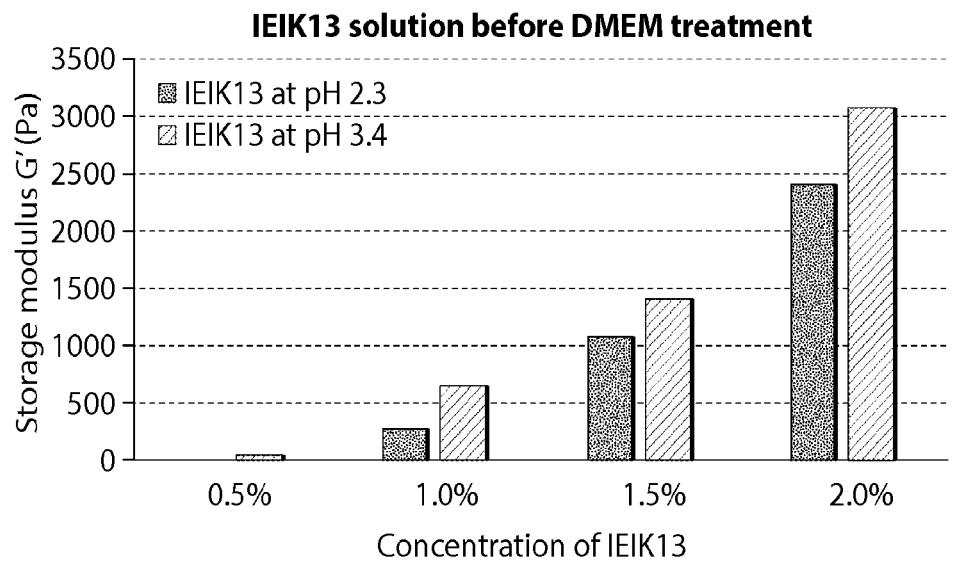
FIGS. 8A-8B present data discussed in Example 5.
Figure 8B:
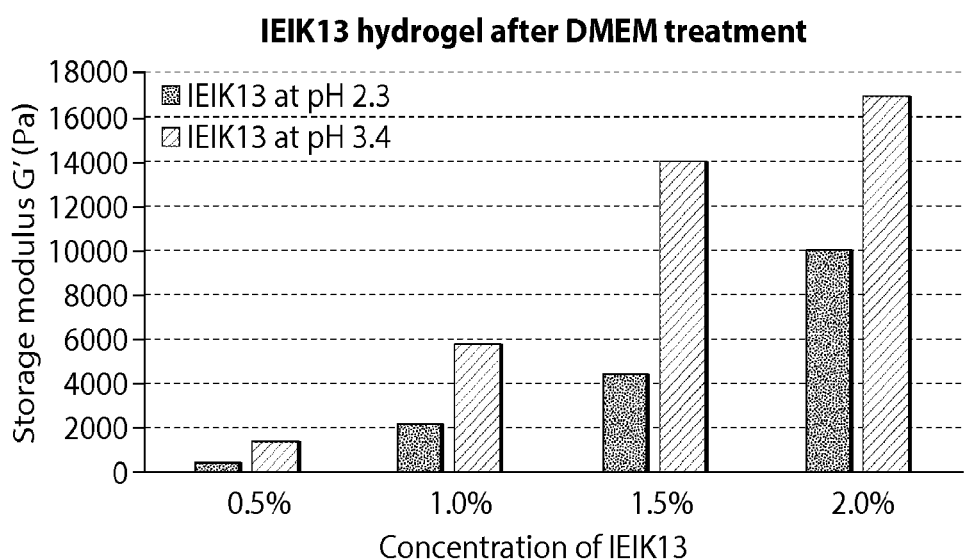

Example 5: Effect of pH Level on Rheological Properties of Peptide Hydrogels at Various Concentrations Before/after DMEM Treatment Based on the results of the effect on the rheological properties of the peptide solutions after adjusting their pH level, the effect on the rheological properties of the peptide hydrogels at various pH after DMEM treatment was evaluated and compared to the effect on the rheological properties of the peptide solutions at various pH before DMEM treatment. The rheological property of PuraMatrix® and IEIK13 hydrogels after DMEM treatment increases with pH adjustment up to 3.4. The results are shown in FIGS. 7A-7B for PuraMatrix® and FIGS. 8A-8B for IEIK (SEQ ID NO: 5), respectively. Frequency sweep tests were performed from 1 rad/sec to 10 rad/sec at 1 Pa and the storage modulus at 1 rad/sec was selected for data.

Example 6: Effect on Gelation Kinetics of pH Adjusted Peptide Hydrogels

The effect of pH level on the properties of gelation kinetics was evaluated to identify optimized pH levels for the peptides as described herein. Fast gelation kinetics of PuraMatrix® and other peptides within body fluid may generally improve its function and response time for various clinical applications. The pH level may impart response time to begin gelation when treated with simulated body fluid including but not limited to DMEM. PuraMatrix® without pH adjustment (pH 2.2) did not show a storage modulus increase for the initial 13 seconds, while PuraMatrix® with pH adjustment showed immediate storage modulus increase due to fast gelation. A fast response time of PuraMatrix® and other peptides within body fluid may generally improve its function and response time for various clinical applications.

Figure 9A:
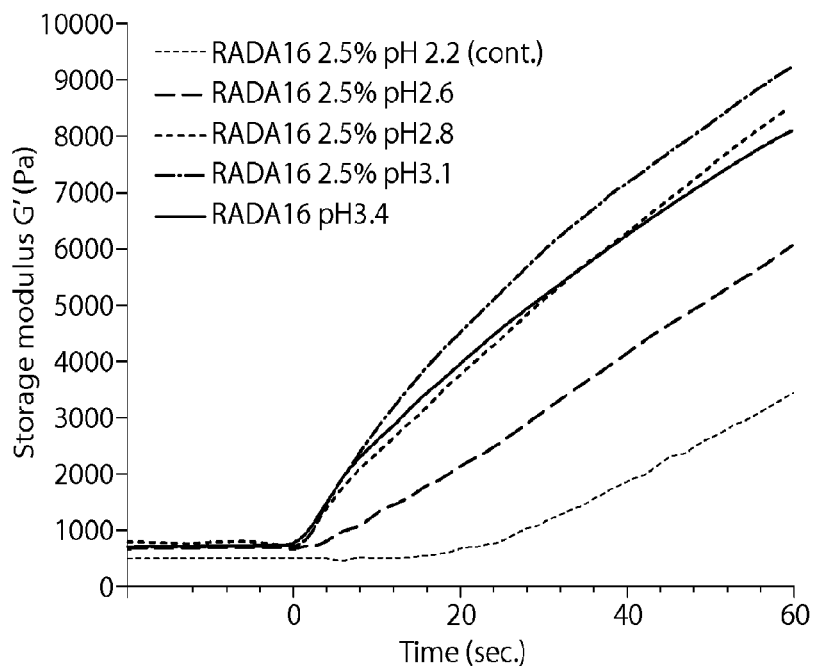
FIGS. 9A-9B present data discussed in Example 6.

Time sweep tests were performed at 1 rad/sec and at 1 Pa with 20 mm plates and 500 μm gap distance. During time sweep test of PuraMatrix® 2.5% solution, DMEM was added into the chamber surrounding the measuring plates to soak PuraMatrix® solution at 0 time point. The results are shown in FIG. 9A for PuraMatrix® 2.5% solution.

IEIK (SEQ ID NO: 5) without pH adjustment showed an immediate storage modulus increase, while PuraMatrix® without pH adjustment (pH 2.2) did not show a storage modulus increase for the initial 13 seconds. IEIK13 with pH adjustment also showed an immediate storage modulus increase due to fast gelation. A fast response time of IEIK13 within body fluid may generally improve its function and response time for various clinical applications.

Figure 9B:
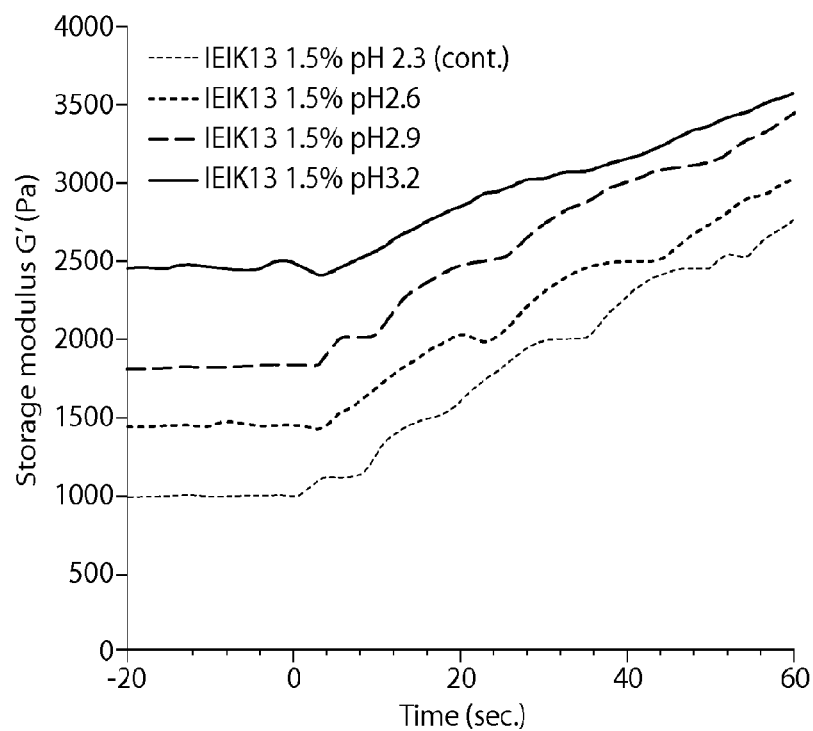

Time sweep tests were performed at 1 rad/sec and at 1 Pa with 20 mm plates and 500 µm gap distance. During time sweep test of IEIK13 1.5% solution, DMEM was added into the chamber surrounding the measuring plates to soak IEIK13 1.5% solution at 0 time point and continuously data was recorded. The results are shown in FIG. 9B for IEIK13 1.5% solution.

Example 7: Effect of Salt Ionic Strength Level on Peptide Solutions and Hydrogels The effect of salt ionic strength level on the properties of peptide solutions was evaluated to identify optimized salt ionic strength levels for the peptides as described herein. Increasing the salt ionic strength level of PuraMatrix® and other peptides may generally improve its function and mechanical strength for various clinical applications. To adjust the salt ionic strength of the peptide solutions by way of example, various salt buffer solutions including NaCl, KCl, $MgCl_2$, $CaCl_2$ and DPBS (10×) were added to 2 mL of 1.5% peptide solutions.

Results are shown for PuraMatrix® in Table 2a. Notably, a salt ionic strength increase up to approximately 0.85~1.15 M (depending on different salts) did not noticeably change the clear color of PuraMatrix® solutions, while their apparent stiffness increased. Results are shown for KLD12 in Table 2b. Notably, a salt ionic strength increase up to approximately 0.25~0.35 M (depending on different salts) did not noticeably change the clear color of KLD12 solutions, while their apparent stiffness increased. Results are shown for IEIK13 in Table 2c. Notably, a salt ionic strength increase up to approximately 0.025~0.035 M (depending on different salts) did not change the clear color of IEIK13 solutions, while their apparent stiffness increased.

TABLE 2a

Appearance of PuraMatrix® solution with various salts at room temperature

| Salt solution | Volume of salt solution added in 1.5% PuraMatrix® solution (µL/mL) | Conc. of PuraMatrix® (%) | Conc. of salt (M) | Ionic Strength (M) | Appearance |
|---|---|---|---|---|---|
| NaCl | 0 | 1.5 | 0 | 0 | Clear, thick gel |
| (3M-as a | 52.6 | 1.43 | 0.15 | 0.15 | Clear, thick, stiffer gel |
| stock | 111.1 | 1.35 | 0.3 | 0.3 | Clear, thick, stiffer gel |
| solution) | 176.5 | 1.27 | 0.45 | 0.45 | Clear, thick, stiffer gel |
|  | 250 | 1.2 | 0.6 | 0.6 | Clear, thick, stiffer gel |
|  | 333.3 | 1.13 | 0.75 | 0.75 | Clear, thick, stiffer gel |
|  | 363.6 | 1.10 | 0.8 | 0.8 | Clear, thick, stiffer gel |
|  | 395.3 | 1.08 | 0.85 | 0.85 | Clear, thick, stiffer gel |
|  | 428.6 | 1.05 | 0.9 | 0.9 | Slightly cloudy, brittle gel |
|  | 463.4 | 1.03 | 0.95 | 0.95 | Cloudy, phase-separated |
|  | 500 | 1.0 | 1.0 | 1.0 | Cloudy, phase-separated |
| KCl | 0 | 1.5 | 0 | 0 | Clear, thick gel |
| (3M-as a | 52.6 | 1.43 | 0.15 | 0.15 | Clear, thick, stiffer gel |
| stock | 111.1 | 1.35 | 0.3 | 0.3 | Clear, thick, stiffer gel |
| solution) | 176.5 | 1.27 | 0.45 | 0.45 | Clear, thick, stiffer gel |
|  | 250 | 1.2 | 0.6 | 0.6 | Clear, thick, stiffer gel |
|  | 333.3 | 1.13 | 0.75 | 0.75 | Clear, thick, stiffer gel |
|  | 428.6 | 1.05 | 0.9 | 0.9 | Clear, thick, stiffer gel |
|  | 463.4 | 1.03 | 0.95 | 0.95 | Clear, thick, stiffer gel |
|  | 500 | 1.0 | 1.0 | 1.0 | Clear, thick, stiffer gel |
|  | 538.5 | 0.98 | 1.05 | 1.05 | Slightly cloudy, thick, stiffer gel |
|  | 578.9 | 0.95 | 1.1 | 1.1 | Slightly cloudy, brittle gel |
|  | 621.6 | 0.93 | 1.15 | 1.15 | Cloudy, phase-separated |
| $MgCl_2$ | 0 | 1.5 | 0 | 0 | Clear, thick gel |
| (3M-as a | 16.9 | 1.48 | 0.05 | 0.15 | Clear, thick, stiffer gel |
| stock | 34.5 | 1.45 | 0.1 | 0.3 | Clear, thick, stiffer gel |
| solution) | 52.6 | 1.43 | 0.15 | 0.45 | Clear, thick, stiffer gel |
|  | 71.4 | 1.4 | 0.2 | 0.6 | Clear, thick, stiffer gel |
|  | 90.9 | 1.38 | 0.25 | 0.75 | Clear, thick, stiffer gel |
|  | 111.1 | 1.35 | 0.3 | 0.9 | Clear, thick, stiffer gel |
|  | 132.1 | 1.32 | 0.35 | 1.05 | Clear, thick, stiffer gel |
|  | 146.5 | 1.31 | 0.383 | 1.15 | Clear, thick, stiffer gel |
|  | 153.8 | 1.3 | 0.4 | 1.2 | Slightly cloudy, thick, stiffer gel |
|  | 161.3 | 1.29 | 0.417 | 1.25 | Slightly cloudy, brittle gel |
|  | 168.8 | 1.28 | 0.433 | 1.3 | Cloudy, phase-separated |
| $CaCl_2$ | 0 | 1.5 | 0 | 0 | Clear, thick gel |
| (3M-as a | 16.9 | 1.48 | 0.05 | 0.15 | Clear, thick, stiffer gel |
| stock | 34.5 | 1.45 | 0.1 | 0.3 | Clear, thick, stiffer gel |
| solution) | 52.6 | 1.43 | 0.15 | 0.45 | Clear, thick, stiffer gel |
|  | 71.4 | 1.4 | 0.2 | 0.6 | Clear, thick, stiffer gel |
|  | 90.9 | 1.38 | 0.25 | 0.75 | Clear, thick, stiffer gel |
|  | 111.1 | 1.35 | 0.3 | 0.9 | Clear, thick, stiffer gel |
|  | 132.1 | 1.32 | 0.35 | 1.05 | Clear, thick, stiffer gel |
|  | 146.5 | 1.31 | 0.383 | 1.15 | Clear, thick, stiffer gel |
|  | 153.8 | 1.3 | 0.4 | 1.2 | Slightly cloudy, thick, stiffer gel |
|  | 161.3 | 1.29 | 0.417 | 1.25 | Slightly cloudy, brittle gel |
|  | 168.8 | 1.28 | 0.433 | 1.3 | Cloudy, phase-separated |

TABLE 2a-continued

Appearance of PuraMatrix ® solution with various salts at room temperature

| Salt solution | Volume of salt solution added in 1.5% PuraMatrix ® solution (μL/mL) | Conc. of PuraMatrix ® (%) | Conc. of salt (M) | Ionic Strength (M) | Appearance |
| --- | --- | --- | --- | --- | --- |
| DPBS | 0 | 1.5 | 0 | 0 | Clear, thick gel |
| (pH 3.2) | 111.1 | 1.35 | 0.15 | 0.15 | Clear, thick, stiffer gel |
| (10X - | 250 | 1.2 | 0.3 | 0.3 | Clear, thick, stiffer gel |
| 1.5M-as | 428.6 | 1.05 | 0.45 | 0.45 | Clear, thick, stiffer gel |
| a stock | 666.7 | 0.9 | 0.6 | 0.6 | Clear, thick, stiffer gel |
| solution) | 1000 | 0.75 | 0.75 | 0.75 | Clear, thick, stiffer gel |
| | 1500 | 0.6 | 0.9 | 0.9 | Clear, thick, stiffer gel |
| | 1725 | 0.55 | 0.95 | 0.95 | Slightly cloudy, brittle gel |
| | 2000 | 0.5 | 1.0 | 1.0 | Cloudy, phase-separated |

TABLE 2b

Appearance of KLD12 solution with various salts at room temperature

| Salt solution | Volume of salt solution added in 1.5% KLD12 solution (μL/mL) | Conc. of PuraMatrix ® (%) | Conc. of salt (M) | Ionic Strength (M) | Appearance |
| --- | --- | --- | --- | --- | --- |
| NaCl | 0 | 1.5 | 0 | 0 | Clear, thick gel |
| (3M-as a | 16.9 | 1.48 | 0.05 | 0.5 | Clear, thick, stiffer gel |
| stock | 34.5 | 1.45 | 0.1 | 0.1 | Clear, thick, stiffer gel |
| solution) | 52.6 | 1.43 | 0.15 | 0.15 | Clear, thick, stiffer gel |
| | 71.4 | 1.4 | 0.2 | 0.2 | Clear, thick, stiffer gel |
| | 90.9 | 1.38 | 0.25 | 0.25 | Clear, thick, stiffer gel |
| | 111.1 | 1.35 | 0.3 | 0.3 | Slightly cloudy, thick, stiffer gel |
| | 132.1 | 1.32 | 0.35 | 0.35 | Slightly cloudy, brittle gel |
| | 153.8 | 1.3 | 0.4 | 0.4 | Cloudy, phase-separated |
| KCl | 0 | 1.5 | 0 | 0 | Clear, thick gel |
| (3M-as a | 16.9 | 1.48 | 0.05 | 0.5 | Clear, thick, stiffer gel |
| stock | 34.5 | 1.45 | 0.1 | 0.1 | Clear, thick, stiffer gel |
| solution) | 52.6 | 1.43 | 0.15 | 0.15 | Clear, thick, stiffer gel |
| | 71.4 | 1.4 | 0.2 | 0.2 | Clear, thick, stiffer gel |
| | 90.9 | 1.38 | 0.25 | 0.25 | Clear, thick, stiffer gel |
| | 111.1 | 1.35 | 0.3 | 0.3 | Slightly cloudy, thick, stiffer gel |
| | 132.1 | 1.32 | 0.35 | 0.35 | Slightly cloudy, brittle gel |
| | 153.8 | 1.3 | 0.4 | 0.4 | Cloudy, phase-separated |
| $MgCl_2$ | 0 | 1.5 | 0 | 0 | Clear, thick gel |
| (3M-as a | 16.9 | 1.48 | 0.05 | 0.15 | Clear, thick, stiffer gel |
| stock | 22.7 | 1.47 | 0.067 | 0.2 | Clear, thick, stiffer gel |
| solution) | 28.6 | 1.46 | 0.083 | 0.25 | Clear, thick, stiffer gel |
| | 34.5 | 1.45 | 0.1 | 0.3 | Clear, thick, stiffer gel |
| | 40.2 | 1.44 | 0.117 | 0.35 | Clear, thick, stiffer gel |
| | 46.5 | 1.43 | 0.133 | 0.4 | Slightly cloudy, thick, stiffer gel |
| | 52.6 | 1.43 | 0.15 | 0.45 | Slightly cloudy, brittle gel |
| | 58.8 | 1.42 | 0.167 | 0.5 | Cloudy, phase-separated |
| $CaCl_2$ | 0 | 1.5 | 0 | 0 | Clear, thick gel |
| (3M-as a | 16.9 | 1.48 | 0.05 | 0.15 | Clear, thick, stiffer gel |
| stock | 22.7 | 1.47 | 0.067 | 0.2 | Clear, thick, stiffer gel |
| solution) | 28.6 | 1.46 | 0.083 | 0.25 | Clear, thick, stiffer gel |
| | 34.5 | 1.45 | 0.1 | 0.3 | Clear, thick, stiffer gel |
| | 40.2 | 1.44 | 0.117 | 0.35 | Clear, thick, stiffer gel |
| | 46.5 | 1.43 | 0.133 | 0.4 | Slightly cloudy, thick, stiffer gel |
| | 52.6 | 1.43 | 0.15 | 0.45 | Slightly cloudy, brittle gel |
| | 58.8 | 1.42 | 0.167 | 0.5 | Cloudy, phase-separated |

TABLE 2c

Appearance of IEIK13 solution with various salts at room temperature

| Salt solution | Volume of salt solution added in 1.5% IEIK13 solution (μL/mL) | Conc. of PuraMatrix ® (%) | Conc. of salt (M) | Ionic Strength (M) | Appearance |
| --- | --- | --- | --- | --- | --- |
| NaCl | 0 | 1.5 | 0 | 0 | Clear, thick gel |
| (0.2M-as | 25.6 | 1.46 | 0.005 | 0.005 | Clear, thick, stiffer gel |
| a stock | 52.6 | 1.43 | 0.01 | 0.01 | Clear, thick, stiffer gel |
| solution) | 81.1 | 1.39 | 0.015 | 0.015 | Clear, thick, stiffer gel |

TABLE 2c-continued

Appearance of IEIK13 solution with various salts at room temperature

| Salt solution | Volume of salt solution added in 1.5% IEIK13 solution (μL/mL) | Conc. of PuraMatrix® (%) | Conc. of salt (M) | Ionic Strength (M) | Appearance |
|---|---|---|---|---|---|
| | 111.1 | 1.35 | 0.02 | 0.02 | Clear, thick, stiffer gel |
| | 142.9 | 1.31 | 0.025 | 0.025 | Clear, thick, stiffer gel |
| | 176.5 | 1.27 | 0.03 | 0.03 | Slightly cloudy, thick, stiffer gel |
| | 212.1 | 1.24 | 0.035 | 0.035 | Slightly cloudy, brittle gel |
| | 250 | 1.2 | 0.04 | 0.04 | Cloudy, phase-separated |
| KCl (0.2M-as a stock solution) | 0 | 1.5 | 0 | 0 | Clear, thick gel |
| | 25.6 | 1.46 | 0.005 | 0.005 | Clear, thick, stiffer gel |
| | 52.6 | 1.43 | 0.01 | 0.01 | Clear, thick, stiffer gel |
| | 81.1 | 1.39 | 0.015 | 0.015 | Clear, thick, stiffer gel |
| | 111.1 | 1.35 | 0.02 | 0.02 | Clear, thick, stiffer gel |
| | 142.9 | 1.31 | 0.025 | 0.025 | Clear, thick, stiffer gel |
| | 176.5 | 1.27 | 0.03 | 0.03 | Clear, thick, stiffer gel |
| | 212.1 | 1.24 | 0.035 | 0.035 | Slightly cloudy, brittle gel |
| | 250 | 1.2 | 0.04 | 0.04 | Slightly cloudy, brittle |
| | 290.3 | 1.16 | 0.045 | 0.045 | Cloudy, phase-separated |
| $MgCl_2$ (0.2M-as a stock solution) | 0 | 1.5 | 0 | 0 | Clear, thick gel |
| | 25.6 | 1.46 | 0.005 | 0.015 | Clear, thick, stiffer gel |
| | 34.5 | 1.45 | 0.0067 | 0.02 | Clear, thick, stiffer gel |
| | 43.5 | 1.44 | 0.0083 | 0.025 | Clear, thick, stiffer gel |
| | 52.6 | 1.43 | 0.01 | 0.03 | Clear, thick, stiffer gel |
| | 61.9 | 1.41 | 0.0117 | 0.035 | Clear, thick, stiffer gel |
| | 71.4 | 1.40 | 0.0133 | 0.04 | Slightly cloudy, thick, stiffer gel |
| | 81.1 | 1.39 | 0.015 | 0.045 | Slightly cloudy, stiffer gel |
| | 91.1 | 1.37 | 0.0167 | 0.05 | Slightly cloudy, brittle gel |
| | 100.9 | 1.36 | 0.0183 | 0.055 | Cloudy, phase-separated |
| $CaCl_2$ (0.2M-as a stock solution) | 0 | 1.5 | 0 | 0 | Clear, thick gel |
| | 25.6 | 1.46 | 0.005 | 0.015 | Clear, thick, stiffer gel |
| | 34.5 | 1.45 | 0.0067 | 0.02 | Clear, thick, stiffer gel |
| | 43.5 | 1.44 | 0.0083 | 0.025 | Clear, thick, stiffer gel |
| | 52.6 | 1.43 | 0.01 | 0.03 | Clear, thick, stiffer gel |
| | 61.9 | 1.41 | 0.0117 | 0.035 | Clear, thick, stiffer gel |
| | 71.4 | 1.40 | 0.0133 | 0.04 | Slightly cloudy, thick, stiffer gel |
| | 81.1 | 1.39 | 0.015 | 0.045 | Slightly cloudy, thick, stiffer gel |
| | 91.1 | 1.37 | 0.0167 | 0.05 | Slightly cloudy, brittle gel |
| | 100.9 | 1.36 | 0.0183 | 0.055 | Cloudy, phase-separated |

The results from Tables 1a-1c show that the critical salt ionic strengths at which three peptides become cloudy is shown as follows: PuraMatrix® (0.9~1.2 M)>KLD13 (0.3~0.4 M)>IEIK13 (0.03~0.04 M).

Figure 10:
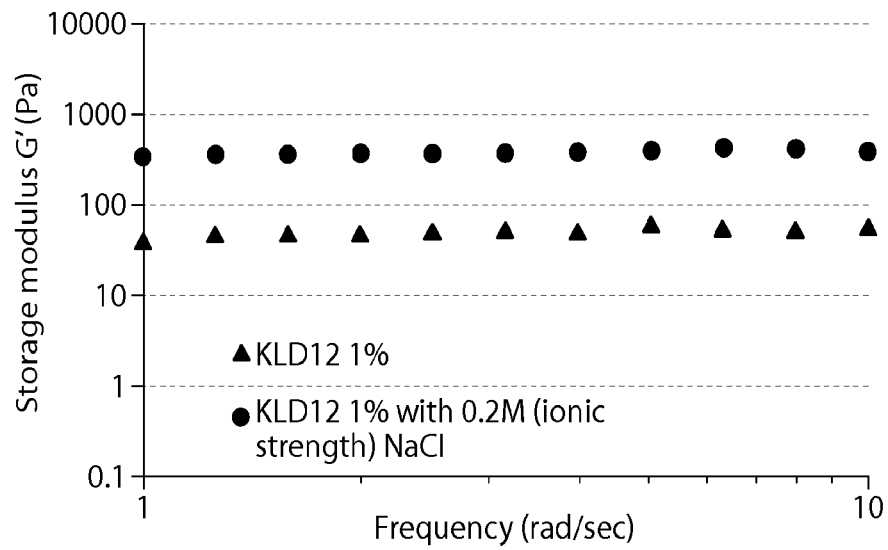
FIGS. 10-12 present data discussed in Example 8.
Figure 11:
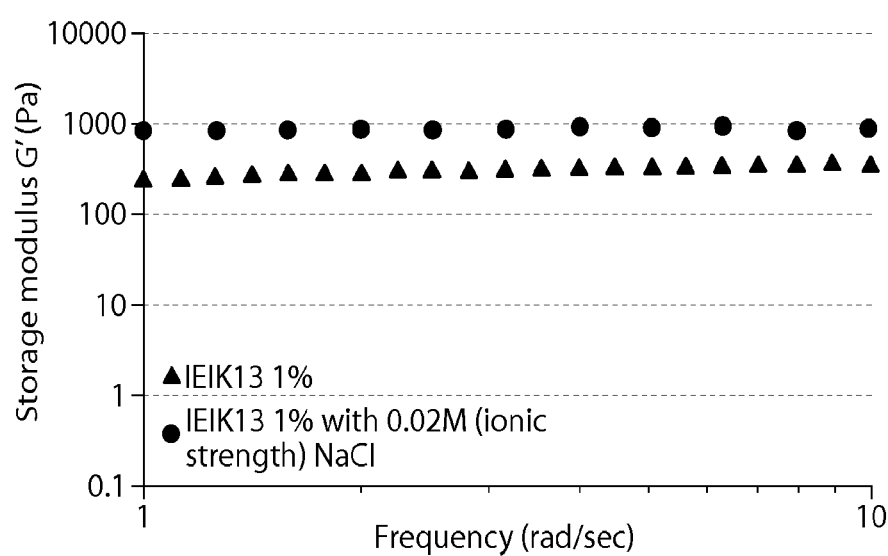
Figure 12:
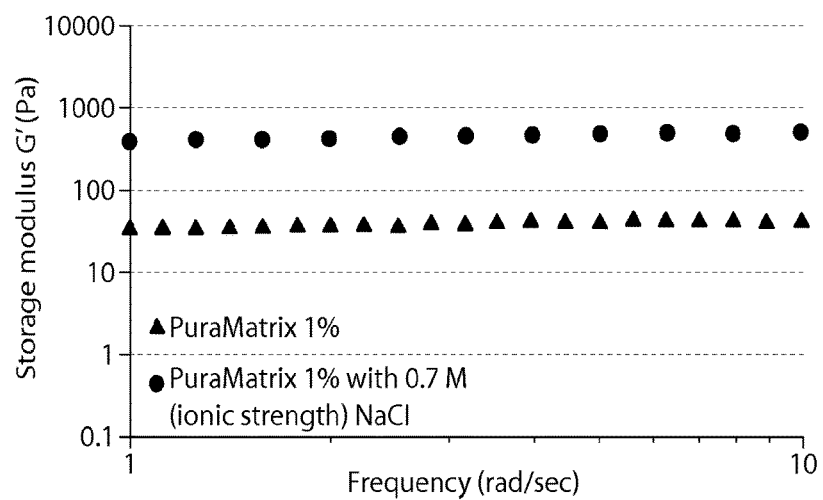

Example 8: Effect of Salt Ionic Strength Level on Rheological Properties of Peptide Solutions Based on the visual observation of the effect of salt ionic strength on the properties of the peptide solutions, the effect on the rheological properties of the peptide solutions after adjusting their ionic strength level with NaCl to 0.7 M (PuraMatrix®), 0.2 M (KLD12) or 0.02 M (IEIK13), which is closely below the critical ionic strength at which each peptide becomes cloudy, was evaluated. If the ionic strength levels with NaCl of peptide solutions are higher than 0.9 M (PuraMatrix®), 0.3 M (KLD12) or 0.03 M (IEIK13), the peptide solution begin phase separation becoming cloudy and weak. The rheological property of PuraMatrix®, KLD12 and IEIK13 solutions was higher after adjusting their ionic strength level with NaCl to 0.7 M (PuraMatrix®), 0.2 M (KLD12) or 0.02 M (IEIK13), The results are shown in FIG. 10 for KLD12 1%, FIG. 11 for IEIK13 1%, and FIG. 12 for PuraMatrix® 1%, respectively. Frequency sweep tests were performed from 1 rad/s to 10 rad/s at 1 Pa.

Figure 13:
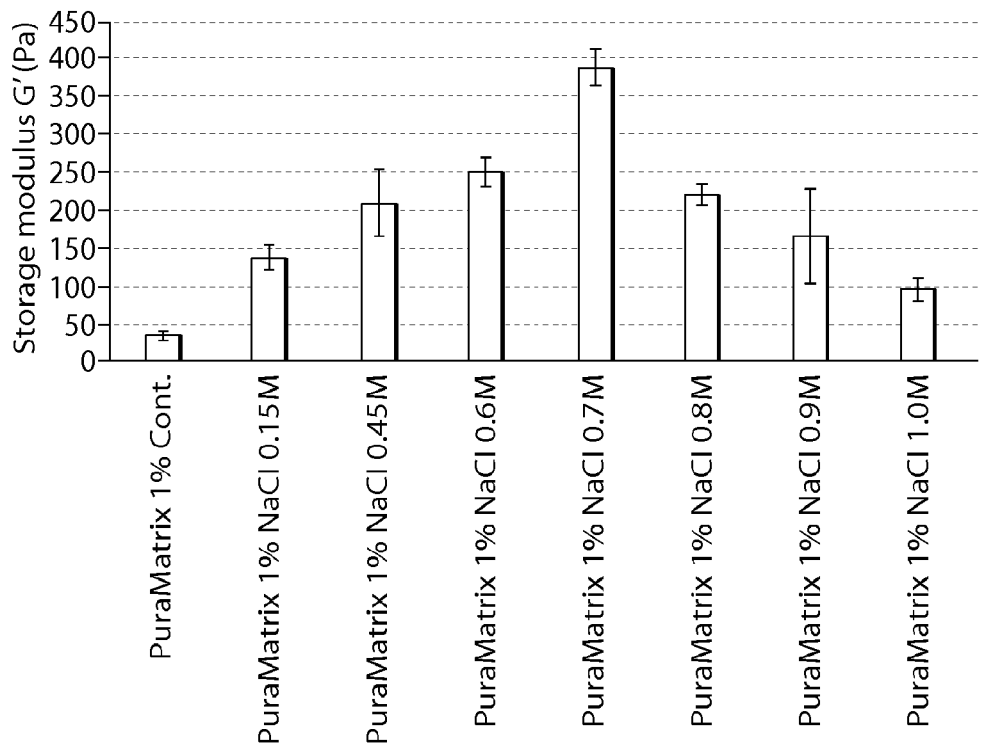
FIGS. 13-14 present data discussed in Example 9.
Figure 14:
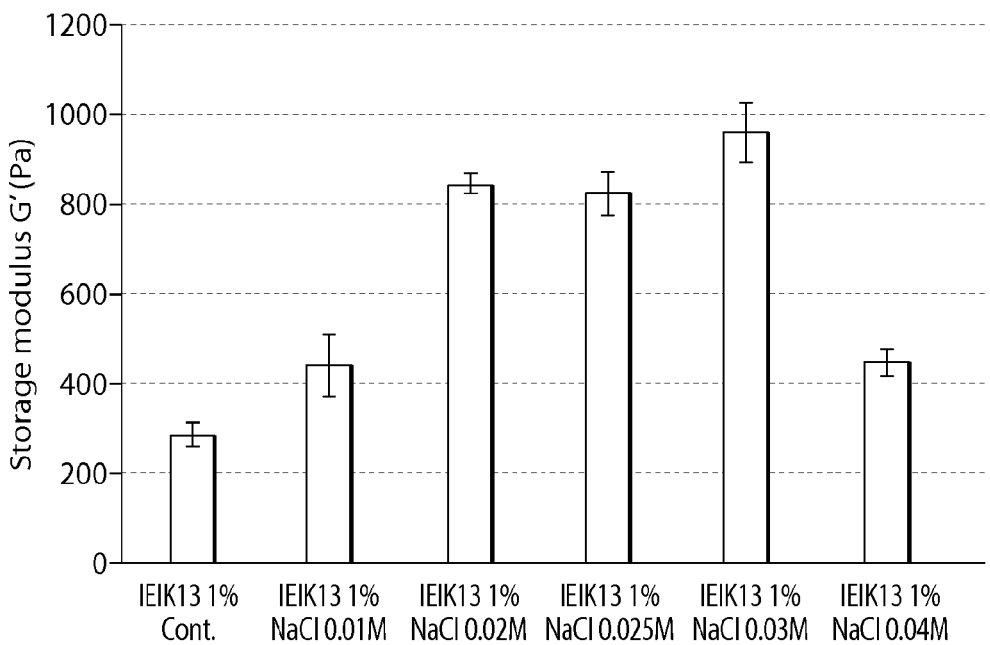

Example 9: Further Effect of Salt Ionic Strength Level on Rheological Properties of Peptide Solutions Based on the results of the effect on the rheological properties of the peptide solutions after adjusting their ionic strength level with NaCl to 0.7 M (PuraMatrix®), 0.2 M (KLD12) or 0.02 M (IEIK13), the effect on the rheological properties of the peptide solution at various salt ionic strengths was evaluated. The rheological property of PuraMatrix® 1% solutions increases with ionic strength adjustment up to 0.7 M, while decreases above 0.7 M. The rheological property of IEIK13 1% solutions increases with ionic strength adjustment up to 0.03 M, while decreases above 0.03 M. These results match well with visual inspection of the peptide solutions at various salt ionic strengths. The results are shown in FIG. 13 for PuraMatrix® 1% solution and in FIG. 14 for IEIK13 1% solution. Frequency sweep tests were performed from 1 rad/sec to 10 rad/sec at 1 Pa and the storage modulus at 1 rad/sec was selected for data.

Figure 15:
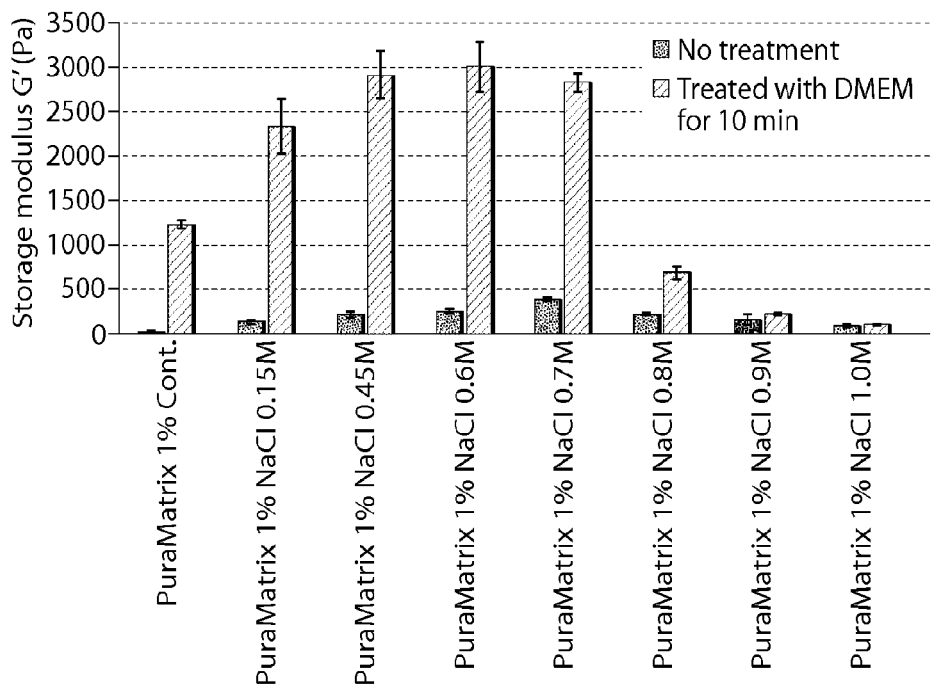
FIGS. 15-16 present data discussed in Example 10.
Figure 16:
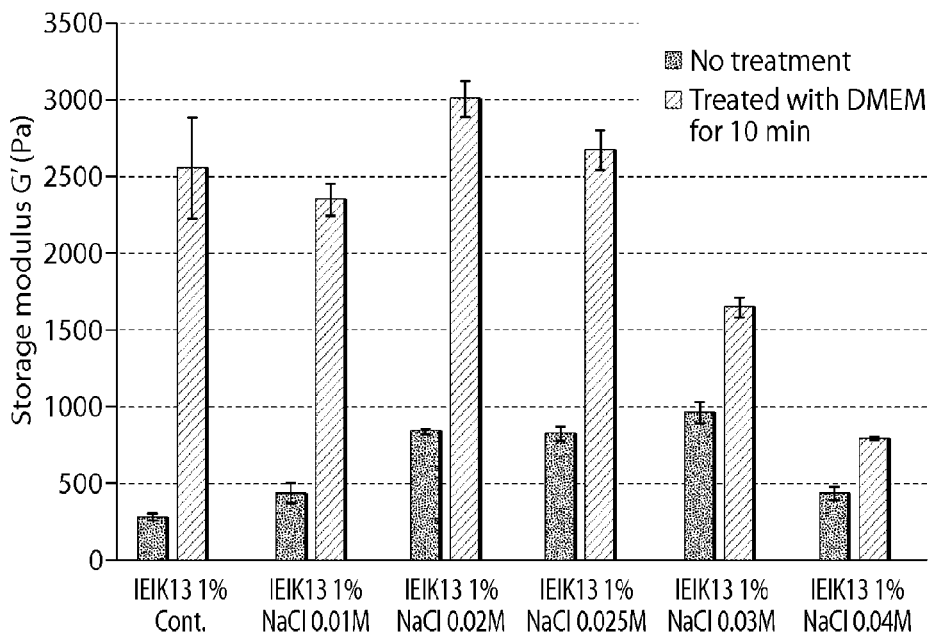

Example 10: Effect on Rheological Properties of Peptide Solutions after DMEM Treatment Based on the results of the effect on the rheological properties of the peptide solutions after adjusting their ionic strength levels, the effect on the rheological properties of the peptide hydrogels after DMEM treatment for 10 min was evaluated. The rheological property of PuraMatrix® hydrogels after DMEM treatment increased with ionic strength adjustment up to 0.7 M, while decreases above 0.7 M. The rheological property of IEIK13 hydrogels after DMEM treatment did not significantly change with ionic strength adjustment up to 0.025 M, while decreases above 0.03 M. Above 0.9 M of NaCl ionic strength at which PuraMatrix® solution becomes cloudy, the rheological properties of PuraMatrix® did not change with DMEM treatment, demonstrating there is no gelation. The results are shown in FIG. 15 for PuraMatrix® 1% hydrogels and in FIG. 16 for IEIK13 1% hydrogels, both after DMEM treatment for 10 min. Frequency sweep tests were performed from 1 rad/sec to 10 rad/sec at 1 Pa and the storage modulus at 1 rad/sec was selected for data.

Example 11: Effect of Various Salts

Figure 17:
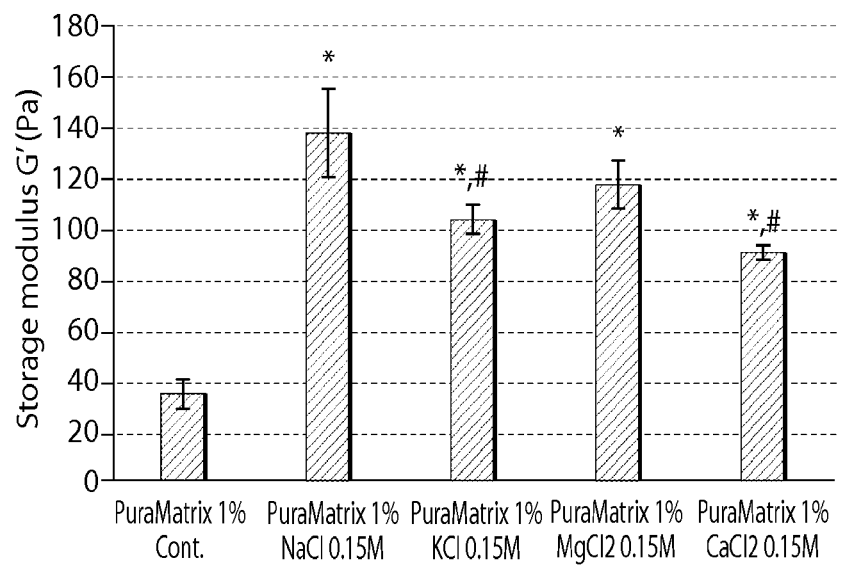
FIGS. 17-18 present data discussed in Example 11.

Based on the results of the effect on the rheological properties of the peptide solutions and hydrogels after adjusting their ionic strength levels with NaCl, the effect of various salts (KCl, $MgCl_2$, and $CaCl_2$) was also evaluated. The rheological property of PuraMatrix® solutions increases with ionic strength adjustment at 0.15 M of all the salts. Increases of the rheological property of PuraMatrix® solutions with various salts were not predominantly different. However, increases of the rheological property of PuraMatrix® solutions may vary depending on the salting out constant, K of each salt. Constant K is a constant in Cohen's equation: log S=B−KI, where S is solubility, B is idealized solubility, K is salting out constant, and I is ionic strength. With a higher value of constant K and ionic strength of salts, solubility of the peptide may decrease resulting in strong peptide self-assembly with increased hydrophobic effect and higher rheological properties of the peptide solution. The constant K of NaCl may be higher than the other salts. Thus, the rheological property of PuraMatrix® solutions with NaCl was slightly higher than those with KCl and $CaCl_2$. The rheological property of PuraMatrix® hydrogels after DMEM treatment for 10 min were also evaluated with ionic strength adjustment with various salts and the results were comparable to increases of the rheological property of PuraMatrix® solutions with various salts ((NaCl, KCL, $MgCl_2$, and $CaCl_2$) at 0.15 M ionic strength). The results are shown in FIG. 17 for PuraMatrix® 1% solution before DMEM treatment, and in FIG. 18 for PuraMatrix® 1% hydrogels after DMEM treatment for 10 min. Frequency sweep tests were performed from 1 rad/sec to 10 rad/sec at 1 Pa and the storage modulus at 1 rad/sec was selected for data. * denotes that data is significantly higher than PuraMatrix® control data (P<0.05). # denotes that data is significantly lower than PuraMatrix® 1% NaCL 0.15M (ionic strength) data (P<0.05).

Example 12: Effect of Various Salts on Gelation Kinetics

Figure 19:
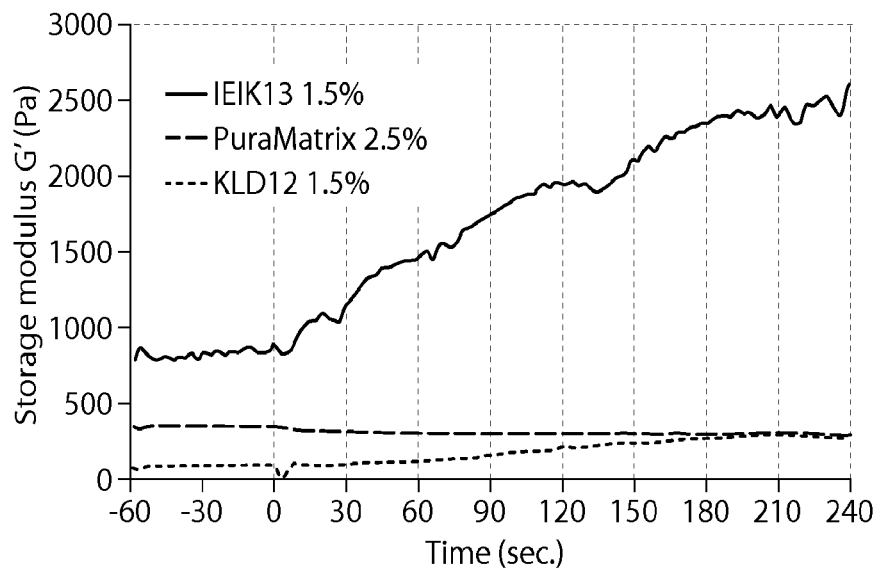
FIG. 19 presents data discussed in Example 12.

The effect of salt ionic strength level surrounding peptide solution on the properties of peptide solutions was evaluated to identify the possibility of peptide gelation when the peptide solution is placed into the environment where salt ionic strength level is high. For example, the hydrogels may be placed in the isotonic body fluid, which is comparable to saline buffer (0.15 M of NaCl). As demonstrated before, self-assembly peptides including but not limited to PuraMatrix®, KLD12 and IEIK13 form hydrogels when they are treated at neutral pH. Without pH effect, the effect of saline treatment on gelation of peptide solutions were evaluated. When peptide solutions were treated with saline buffer, their pH did not change. After saline buffer treatment, only IEIK13 showed fast gelation, while PuraMatrix® and KLD13 showed no or negligible gelation. This is because IEIK13 is much more sensitive to salt ionic strength levels. Fast gelation of IEIK13 at the salt ionic strength level similar to body fluid isotonic salt level may generally improve its function and gelation speed for various clinical applications. The results are shown in FIG. 19 for IEIK13, KLD12 and PuraMatrix® solutions. Time sweep tests were performed at 1 rad/sec and at 1 Pa with 20 mm plates and 500 μm gap distance. During time sweep test of IEIK13 1.5%, KLD12 1.5%, and PuraMatrix® 2.5% solution, DMEM was added into the chamber surrounding the measuring plates to soak PuraMatrix® solution at 0 time point.

Figure 20:
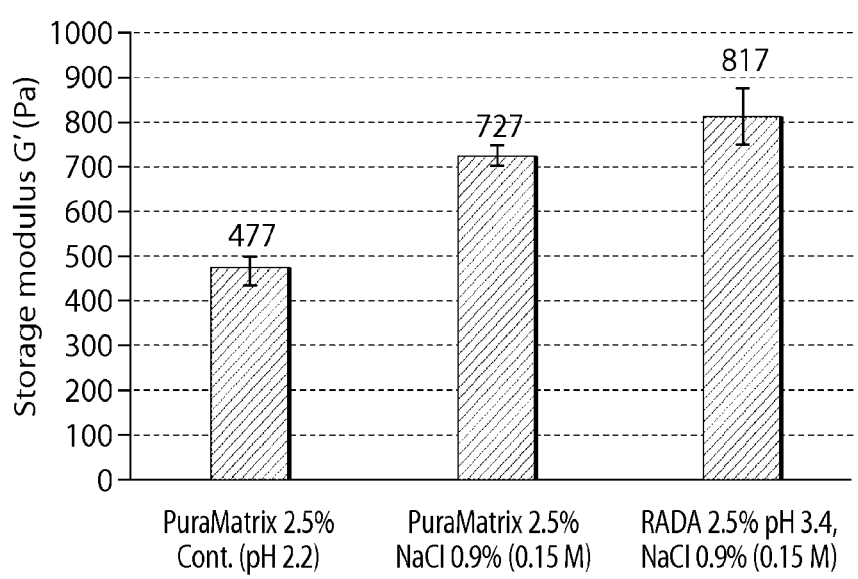
FIG. 20 presents data discussed in Example 13.

Example 13: Effect of Salt Ionic Strength and pH Adjustment on Rheological Properties In accordance with one or more embodiments, IEIK13, KLD12, and PuraMatrix® may be dissolved both in salt buffer such as NaCl and at an elevated pH level adjusted with alkali salt buffer such as NaOH to keep their salt ionic strength under their critical salt points as well as their pH level to about 2.5~4.0, so that they may have stiffer properties. With respect to PuraMatrix®, KLD13 and IEIK13, the peptide solutions are still clear with 0.9% NaCl (ionic strength: 0.15 M) at pH 3.4 adjusted with NaOH. The rheological property of PuraMatrix® with 0.9% NaCl (ionic strength: 0.15 M) at pH 3.4 was stiffer than those of PuraMatrix control and PuraMatrix with only NaCl 0.9%. The effect of salt ionic strength and pH adjustment on the rheological properties of PuraMatrix® 2.5% solution are shown in FIG. 20. Frequency sweep tests were performed from 1 rad/sec to 10 rad/sec at 1 Pa and the storage modulus at 1 rad/sec was selected for data.

Example 14: Influence of Cations

Figure 18:
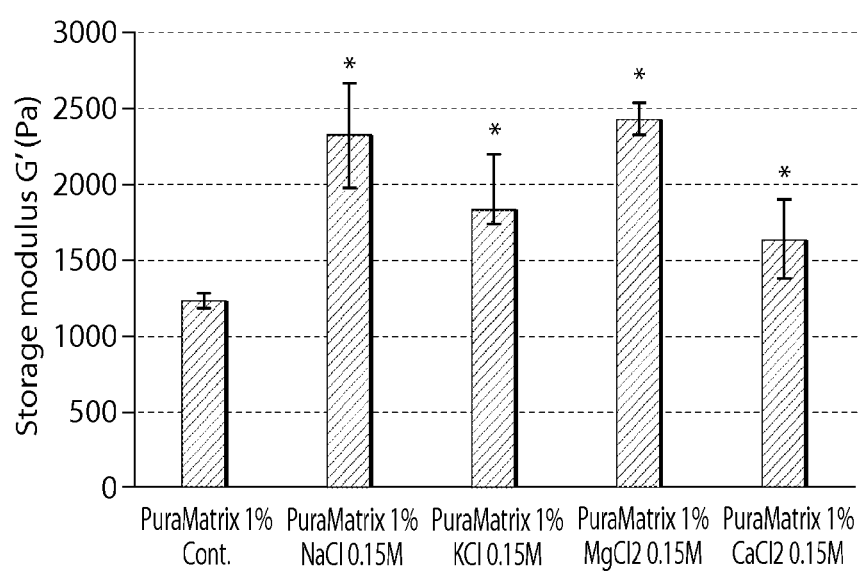
Figure 21:
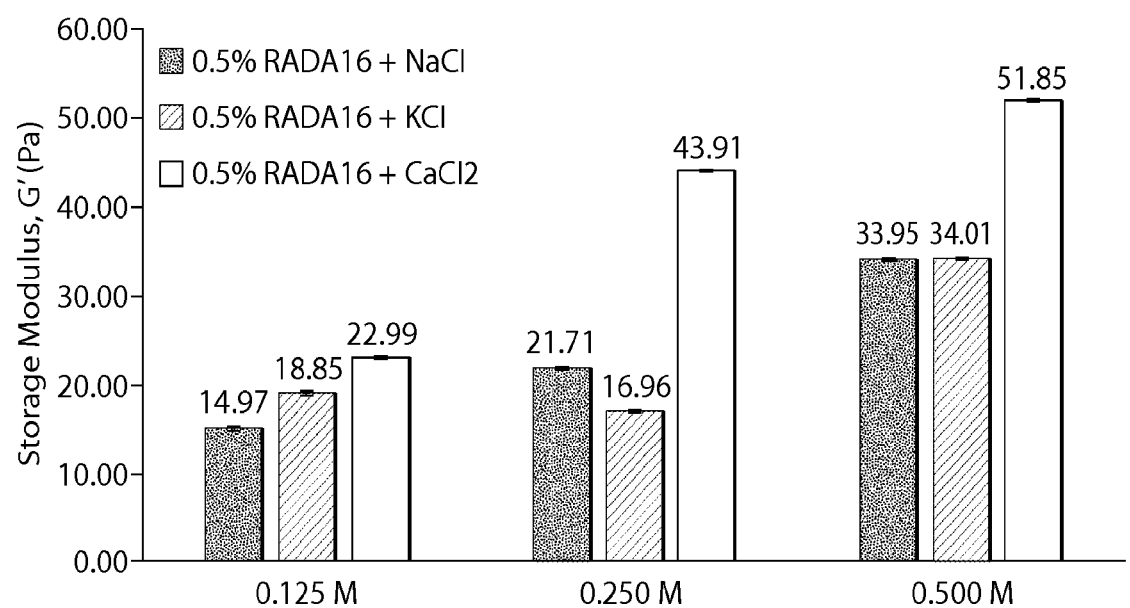
FIG. 21 presents data discussed in Example 14.

In a rheological comparison of 2.5% RADA16 and 2.5% RADA16+NaCl, KCl, and CaCl2, solutions of 0.5% RADA16 mixed with 0.005, 0.05, 0.125, 0.25, 0.5, and 1 M NaCl, KCl, and CaCl2 were prepared. The anion, chloride (Cl−), was kept the same to observe the effect of the cations, sodium (Na+), potassium (K+), and calcium (Ca2+). FIG. 21 provides a basic understanding of how varying the cations of a salt solution effects the viscoelastic properties and the stiffness of self-assembling peptides. Ca provided the best enhancement of stiffness compared to either Na or K at the same molar concentrations. This should be because Ca has four times higher ionic strength than Na and K at the same molar concentrations. Therefore, influence of salts on the peptide solution is more related to their ionic strength rather than their molar concentration, as shown in FIGS. 17-18 and Table 2a-c. In some embodiments, there is a correlation between the properties of the peptide solutions with salts based on the concentration of the salts.

Example 15: Mechanical Strength

Figure 22:
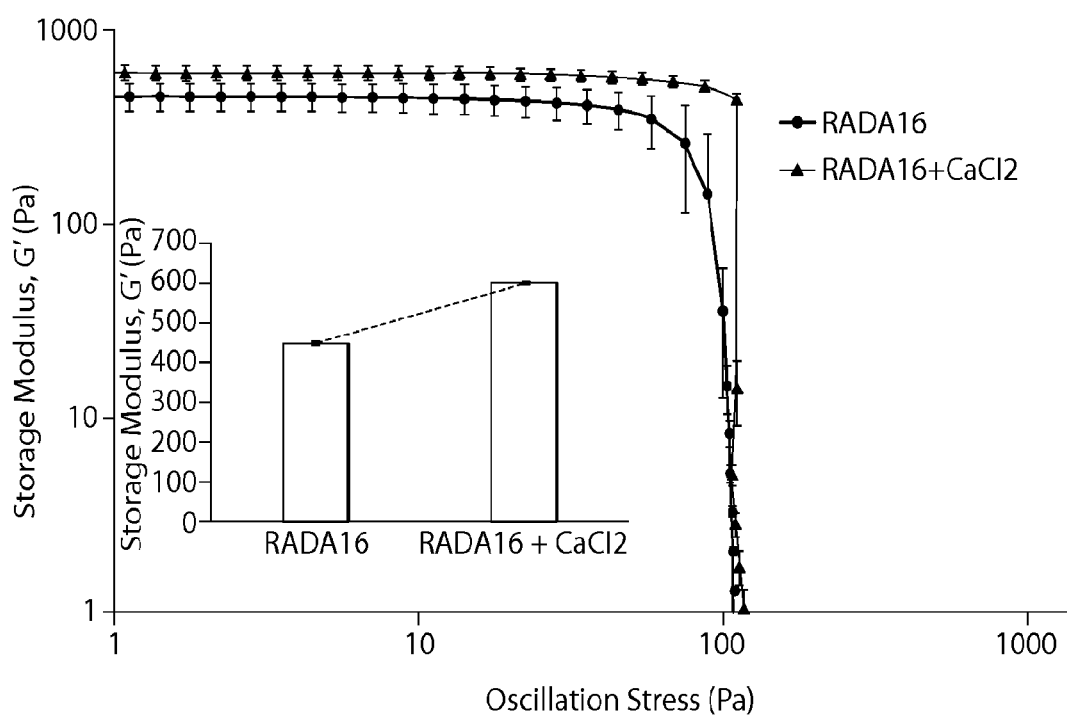
FIG. 22 presents data discussed in Example 15.

Rheological measurements of stiffness of 2.5% RADA16 and 2.5% RADA16+0.25 M CaCl2 was evaluated. FIG. 22 compares the stiffness of a high concentrated solution of RADA16 with another high concentrated solution of RADA16 with an addition of 0.125 M CaCl2 and provides a basic understanding of the viscoelastic properties of the peptide and peptide mixture. There was a noticeable increase in stiffness between the two solutions when a cation solution was added. Ca was shown to provide mechanical enhancement of RADA16 even at high concentrations using the optimal concentration range.

Example 16: Reversibility

Figure 23A:
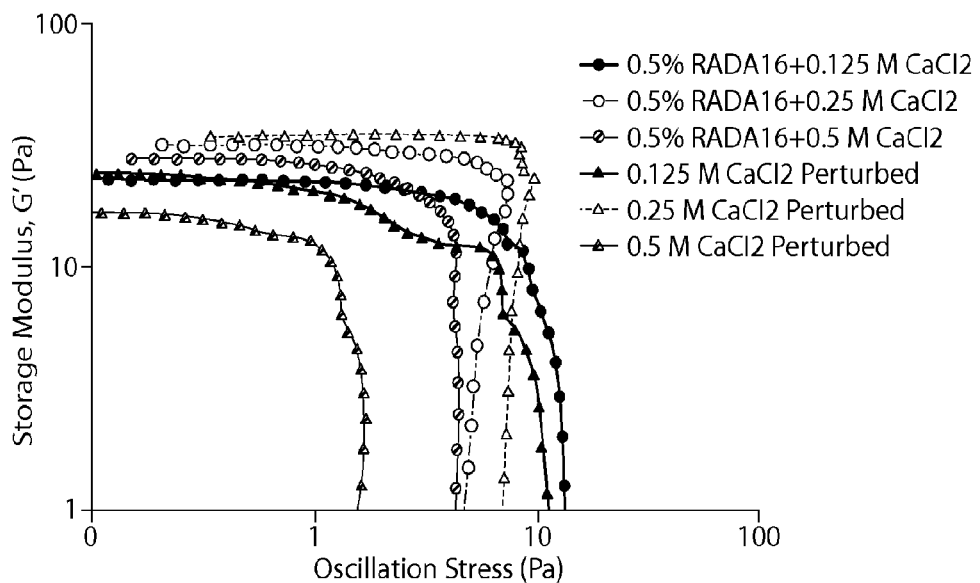
FIGS. 23A-23B present data discussed in Example 16.
Figure 23B:
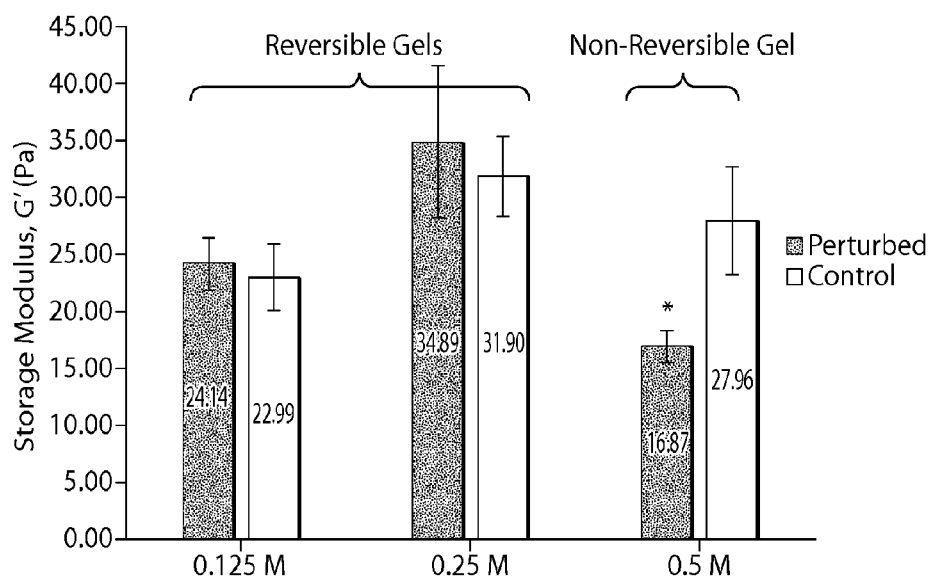

Rheological measurements of reversibility of 0.5% RADA16 solution with +0.125, 0.25, and 0.5 M CaCl2 were evaluated. Solutions of 0.5% RADA16 mixed with 0.125, 0.25, and 0.5 M CaCl2 were prepared. The structure of the self-assembled peptide solution were disrupted thoroughly by application of mechanical stress through vortexing and sonication. The mixtures were placed at room temperature for 48 hours to allow self-assembly to take place. FIGS. 23A-23B provide the basic viscoelastic properties of the peptide mixtures and show that reversibility of the peptide solution with salts can be controlled and maintained even after perturbation of the structure, specifically noted by the significant difference between the 2.5% RADA16+0.5 M CaCl2 control and perturbed samples. The mixtures within the optimal salt concentration range remained reversible. The * denotes the control sample and the perturbed sample, which follows, as being significantly different. FIG. 23a presents raw rheological data of the peptide solution with salts and the perturbed peptide solution while FIG. 23b provides a comparison of stiffness of the control peptide solution and the perturbed peptide solution.

Example 17: Gelation Kinetics

Rheological measurements of gelation kinetics of 0.5% RADA16+NaCl, KCl, and CaCl2 were evaluated. A solution of 0.5% RADA16 was prepared and gelation kinetics were observed by treatment with several cations (e.g. Na, Cl, K) and anions (e.g. Cl, CO4, PO4, SO4). It was determined how long it will take for the peptide mixtures to gel and how to control that gelation time by varying the cation/anion type and concentration. Chlorine showed the quickest gelation and sulfate showed the slowest gelation. In vivo and in vitro qualitative experiments and the resulting observations were supportive of these conclusions.

Example 18: Varying Cations

A peptide hydrogel mixed with a cation/anion solution which affected mechanical properties and another with a very low concentration of a contrast agent which did not affect the mechanical properties were both designed. The two gels were: (1) a combination of the self-assembling peptide with a well-known cation/anion solution, Ringer's Solution (pH 5.3), used in the medical field and (2) a combination of the self-assembling peptide with a well-known contrast agent, indigo carmine, which is a dye solution containing sulfate (anion) and sodium (cation) ions. Indigo carmine contains indigoindisulfonate sodium ($C_{16}H_8N_2Na_2O_8S_2$), water, and sodium citrate ($C_6H_8O_7$) for pH adjustment. Using indigo carmine powder, a 1% solution was prepared for use in experimentation. This corresponds to 10 mg/1 ml of water. The concentration of indigo carmine solution used in experimentation was 0.00585% in water.

Indigo carmine powder was used to prepare a 1% solution in deionized (DI) water. Using IEIK13 powder, a 2 percent solution was prepared using DI water. The amount of IEIK was weighed out and the appropriate amount of DI water was added gently down the side of the container. Mixing was accomplished by vortexing for about 30 seconds, and then sonicating for 30 seconds. The solution was then centrifuged for about 10 to about 15 minutes at 3000 ppm. The solution may undergo further vortexing and centrifuging until the solution is clear and without bubbles.

To obtain a final concentration of 0.00585% indigo carmine, the necessary amount of 1% IC is added to the appropriate amount of DI water to dilute 2% IEIK to 1.5% IEIK. The solution is then vortexted for about 30 seconds and centrifuged for about 10 to about 15 minutes at 3000 rpm. The solution may undergo further vortexing and centrifuging until the solution is clear and without bubbles.

The solution was allowed to sit overnight at room temperature prior to use. The cap may be left off of the container during preparation to allow more efficient removal of bubbles.

Figure 24A:
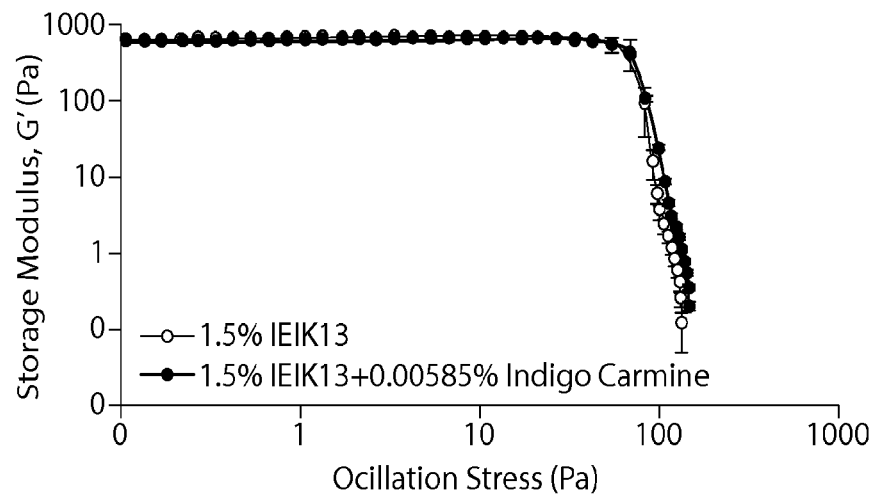
FIGS. 24A-24C present data discussed in Example 18.
Figure 24B:
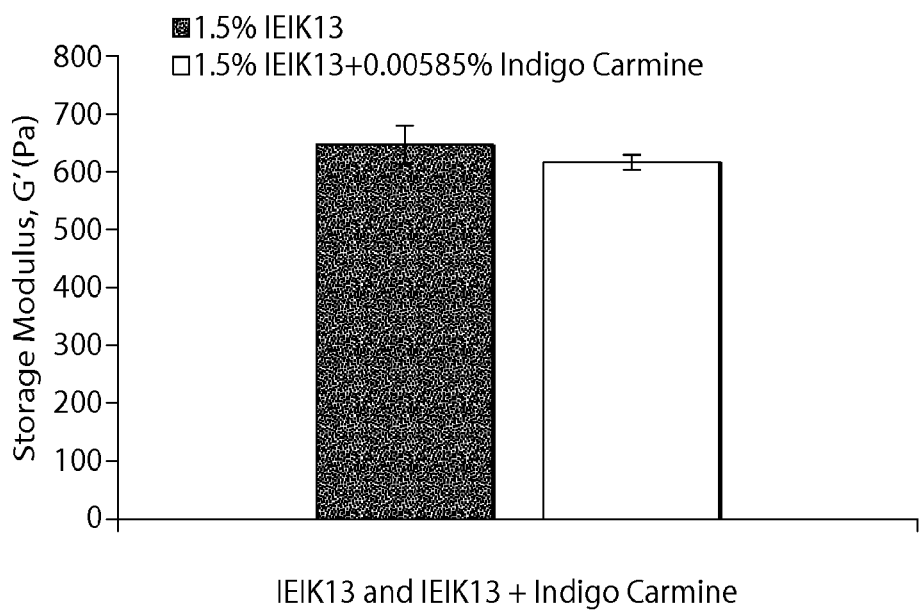
Figure 24C:
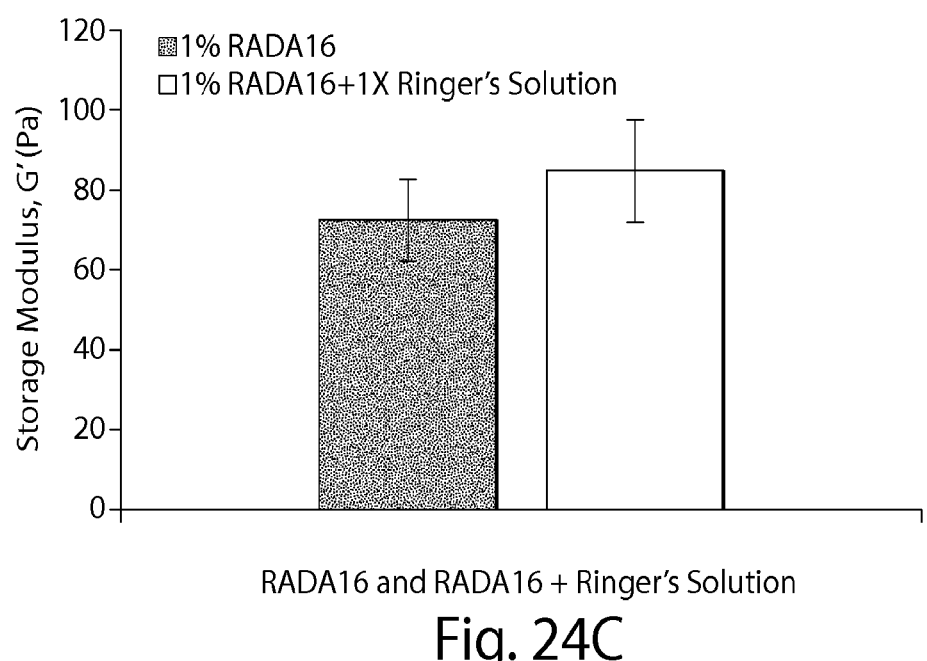

The rheological comparisons of these mixtures and the visualization of the gels can be observed in FIG. 24a-24c. A stiffer gel with faster gelation kinetics that maintains reversibility was obtained. Another that maintains stiffness, reversibility, and gelation kinetics, but allows for the dying of tissues for histology was also obtained. The concentration of the contrast agent or cation/anion mixture and peptide hydrogel that were mixed were based on an understanding of using cations and anions as described herein. The data relating to these tailored peptide hydrogels of RADA16+ Ringer's Solution and IEIK13+Indigo Carmine show that these controlled self-assembling hydrogels can be tailored to fit the needs for an isotonic injectable gel and a non-mechanically enhanced gel for visualization. FIG. 24A presents raw rheological data of IEIK (SEQ ID NO: 5) and IEIK (SEQ ID NO: 5) mixed with Indigo Carmine FIG. 24B shows a comparison of stiffness of IEIK (SEQ ID NO: 5) and IEIK (SEQ ID NO: 5) mixed with Indigo Carmine. FIG. 24C presents a comparison of stiffness of RADA16 and RADA16 mixed with Ringer's Solution.

Example 19: Pulmonary Bullae Treatment

Injectable, self-assembling peptide hydrogel systems were demonstrated to act as an air sealant for pulmonary bullae. A burst pressure (i.e. the pressure at which air breaches the surface of the sealant) of 35 cm $H_2O$ or more was achieved. In contrast to conventional methods for addressing pulmonary bullae which focus on removal, the treatment protocol used herein did not involve resection and/or stapling. The bulla treated were primarily in the range of about 0.2 mL to about 1 mL in volume. Self-assembling peptide solutions were applied until the bulla was filled completely to attempt to provide no air leakage.

Materials and Methods
Experimental Setup

Swine lungs were obtained from freshly euthanized pigs. An endotracheal tube was inserted through the trachea and primary bronchus into the lung of interest. Pressure was supplied to the lungs with the use of a manual endotracheal intubation pump. The trachea was tied off to prevent air leakage around the tube. The other primary bronchus of the other lung was clamped to direct all airflow to the lung of interest. A manometer was used to measure the pressure of air directed into the lungs to induce expansion.

Preparation of Self-Assembling Peptide Hydrogels

The self-assembling peptide hydrogels were comprised of Ac-RADARADARADARADA-NH$_2$ (SEQ ID NO: 1) (i.e. RADA16) and Ac-IEIKIEIKIEIKI-NH$_2$ (SEQ ID NO: 2) (i.e. IEIK13) with RADA16 used alone or mixed with calcium chloride. If alone, the peptides were reconstituted in deionized water. If, however the peptides were reconstituted with a salt solution, the peptides were reconstituted first in deionized water, and subsequently, a 2× solution of calcium chloride at a previously decided concentration which was mixed in at a 1:1 ratio.

Application of Self-Assembling Peptide Hydrogels

Figure 25:
FIG. 25 present materials discussed in Example 19.
Figure 26:
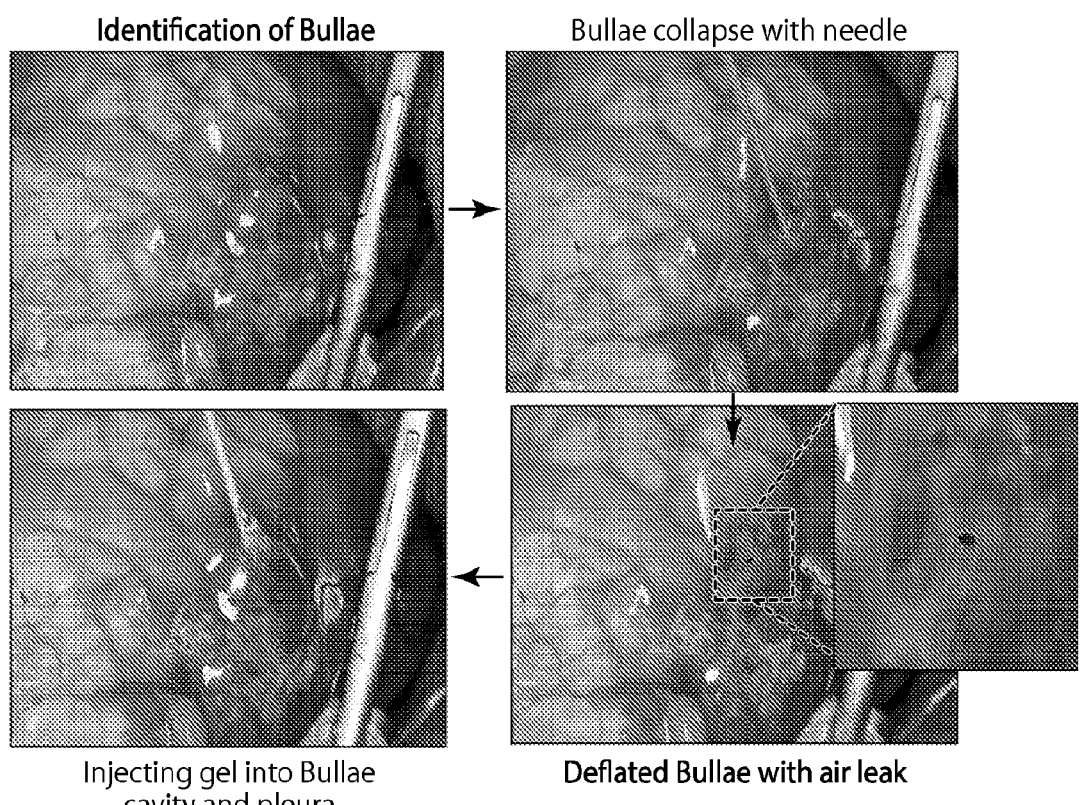
FIG. 26 presents materials discussed in Example 19.

Pulmonary bullae, as depicted in FIG. 25, are naturally occurring weak areas of the pleura. Prior to application of the hydrogels, the bullae were identified and collapsed using a 16 G needle. Once a defect was identified, the hydrogels were applied to the defect area via two different methods: (1) the hydrogel was applied topically by injecting through a syringe onto the defect area, and (2) the hydrogel was injected into the defect through an 18 gauge needle with overflow to cover the defect area topically. After a relaxation period of 2 minutes, pressure was applied through the endotracheal intubation pump until a burst pressure was identified. Method 1 of hydrogel application to a pulmonary bullae is depicted in FIG. 26 which shows the flow of the experimental procedure in identifying and testing a pulmonary bullae with self-assembling peptide hydrogels. For any additional tests, airflow to the previously tested defect was cut off using a surgical clamp.

Results

Figure 27:
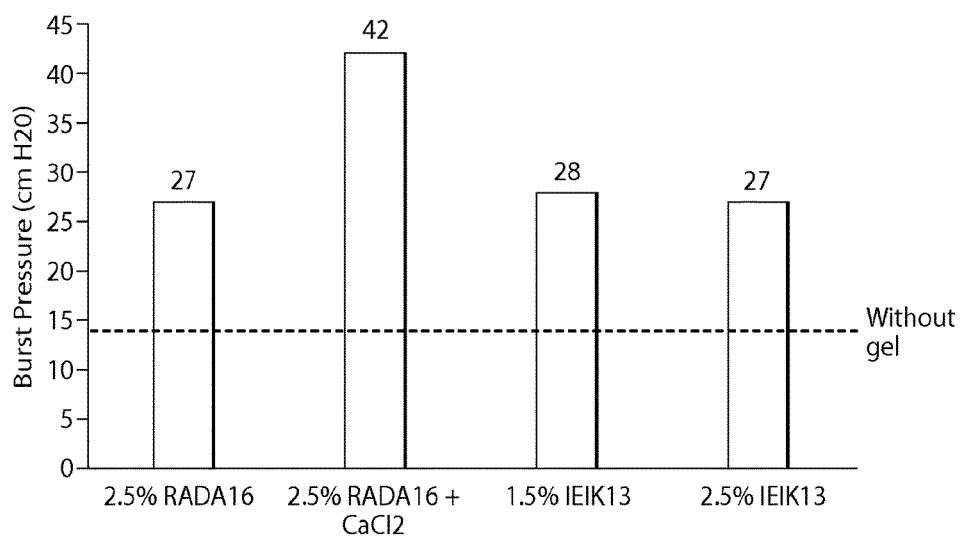
FIG. 27 presents materials discussed in Example 19.

The injection method showed superior results in comparison to the purely topical approach. FIG. 27 shows several formulations used to determine the efficacy of these hydrogels in preventing air leakage. The graph presents the resulting burst pressures of varying hydrogel concentrations and combinations with $CaCl_2$ acting as air sealants for pulmonary bullae. The line indicates the burst pressure without an applied sealant. 2.5% RADA16 with 0.25 M $CaCl_2$, 2.5% IEIK13, and 1.5% IEIK13 all surpassed burst pressures of 35 cm $H_2O$ using the injection method of sealing a pulmonary bullae. 2.5% RADA16 mixed with 0.250 M $CaCl_2$ exhibited the best burst pressure for pulmonary bullae defects.

Figure 28:
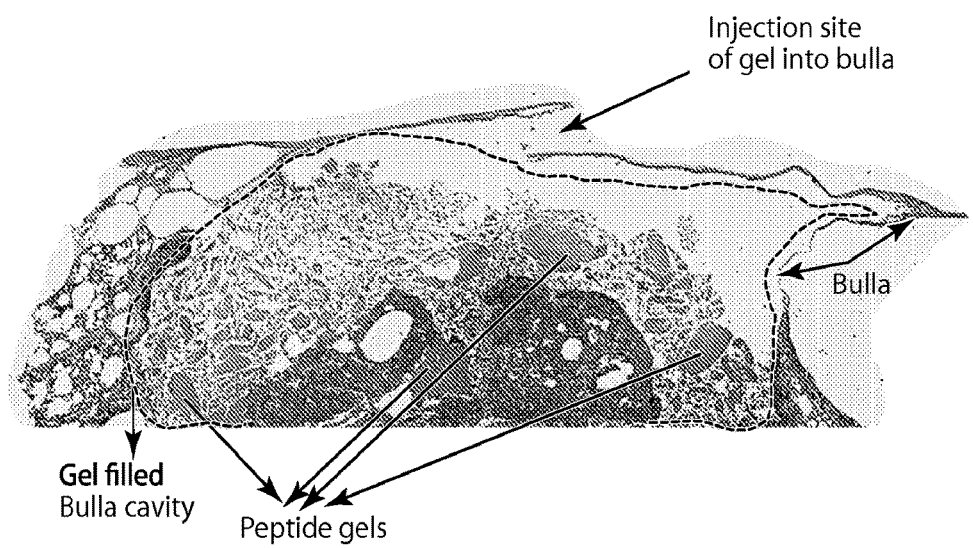
FIG. 28 presents materials discussed in Example 19.

FIG. 28 provides a histology representation of a collapsed bullae sealed and filled with the peptide hydrogel 2.5% RADA16 with 0.25 M $CaCl_2$ and illustrates that the hydrogels successfully filled the collapsed bullae to act as a sealant. After application of 2.5% RADA16 with $CaCl_2$ into a bullae cavity, the tissue was segmented, fixed, and underwent histological analysis to determine how well the hydrogel spreads into the bullae cavity. 2.5% RADA16 with $CaCl_2$ entirely filled the pulmonary bullae cavity.

Conclusion

The use of injectable, self-assembling peptide hydrogel systems, specifically 2.5% RADA16 with 0.250 M $CaCl_2$, 2.5% IEIK13, and 1.5% IEIK13, as air sealants is viable for pulmonary bullae.

Example 20: Alternative Pulmonary Bullae Treatment

A method for pulmonary bullae treatment using peptide hydrogel systems distinct from the method discussed in Example 19 was tested. Here, the pulmonary bullae are generally filled prior to collapse.

Figure 29:
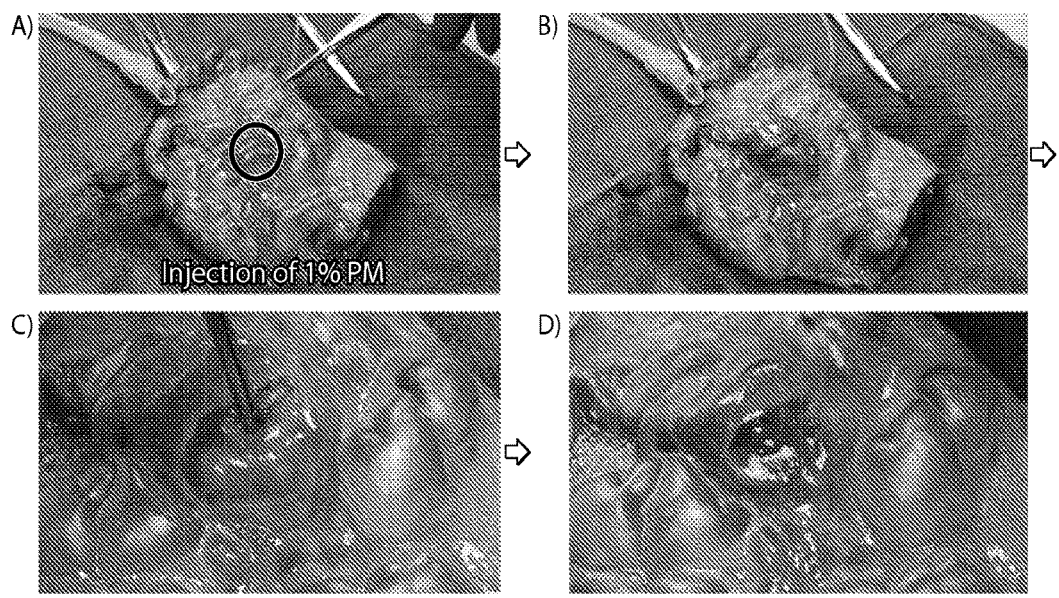
FIG. 29 presents material discussed in Example 20.

The pulmonary bulla cavity was filled with 1.0% RADA16 through the connecting bronchioles using an endotracheal tube inserted through the primary bronchus and into the lung. The bulla was then collapsed to remove the pocket of trapped air. 1.0% RADA16 mixed with 0.00585% indigo carmine was used here for visualization of the hydrogel spreading into the bullae cavity. FIG. 29 shows the procedural flow and that the hydrogel was able to be injected into and completely fill the bullae cavity through the connecting bronchioles: A) Identification of bulla of interest, B) Injection of 1.0% RADA16 with 0.00585% indigo carmine into bulla cavity, C) Collapsing of the bulla to release the trapped air, D) Procedural completion showing a bulla filled with the peptide hydrogel.

CONCLUSION

Injection of a hydrogel into the bullae via the bronchioles may prove to be a feasible alternative method of treating pulmonary bullae.

The invention claimed is:

1. A method of treating a pulmonary bulla in a subject, comprising:

introducing a delivery device to a target area of the pulmonary bulla of the subject;

positioning an end of the delivery device in the target area in which a treatment of the pulmonary bulla is desired;

administering, through the delivery device, a solution comprising an amphiphilic self-assembling peptide comprising between about 7 amino acids and 32 amino acids in an effective amount and in an effective concentration to the target area to form a hydrogel barrier under physiological conditions of the target area to treat the pulmonary bulla;

removing the delivery device from the target area; and collapsing the pulmonary bulla prior or subsequent to administering the solution.

2. The method of claim 1, wherein a cavity of the pulmonary bulla is filled with the solution through connecting bronchioles.

3. The method of claim 2, further comprising inserting an endotracheal tube through a primary bronchus of a lung of the subject.

4. A method of treating a pulmonary bulla in a subject, comprising:
   introducing a delivery device to a target area of the pulmonary bulla of the subject;
   positioning an end of the delivery device in the target area in which a treatment of the pulmonary bulla is desired;
   administering, through the delivery device, a solution comprising an amphiphilic self-assembling peptide comprising between about 7 amino acids and 32 amino acids in an effective amount and in an effective concentration to the target area to form a hydrogel barrier under physiological conditions of the target area to treat the pulmonary bulla, wherein the administering the solution comprises administering the solution in a single dose;
   administering the solution until a volume of the target area is filled; and
   removing the delivery device from the target area.

5. A method of treating a pulmonary bulla in a subject, comprising:
   introducing a delivery device to a target area of the pulmonary bulla of the subject;
   positioning an end of the delivery device in the target area in which a treatment of the pulmonary bulla is desired;
   administering, through the delivery device, a solution comprising an amphiphilic self-assembling peptide comprising between about 7 amino acids and 32 amino acids in an effective amount and in an effective concentration to the target area to form a hydrogel barrier under physiological conditions of the target area to treat the pulmonary bulla; and
   removing the delivery device from the target area,
   wherein the subject has been diagnosed with at least one of emphysema and chronic obstructive pulmonary disease (COPD) prior to administering the solution comprising the amphiphilic self-assembling peptide.

6. A method of treating a pulmonary bulla in a subject, comprising:
   introducing a delivery device to a target area of the pulmonary bulla of the subject;
   positioning an end of the delivery device in the target area in which a treatment of the pulmonary bulla is desired;
   administering, through the delivery device, a solution comprising an amphiphilic self-assembling peptide comprising between about 7 amino acids and 32 amino acids in an effective amount and in an effective concentration to the target area to form a hydrogel barrier under physiological conditions of the target area to treat the pulmonary bulla; and
   removing the delivery device from the target area,
   wherein the solution comprising the amphiphilic self-assembling peptide comprises $(RADA)_4$ (SEQ ID NO: 1) at a concentration of about 0.5 weight per volume (w/v) percent.

7. The method of claim 6, wherein the solution comprising the amphiphilic self-assembling peptide comprises a concentration of calcium chloride of about 0.125 M.

8. A method of treating a pulmonary bulla in a subject, comprising:
   introducing a delivery device to a target area of the pulmonary bulla of the subject;
   positioning an end of the delivery device in the target area in which a treatment of the pulmonary bulla is desired;
   administering, through the delivery device, a solution comprising an amphiphilic self-assembling peptide comprising between about 7 amino acids and 32 amino acids in an effective amount and in an effective concentration to the target area to form a hydrogel barrier under physiological conditions of the target area to treat the pulmonary bulla;
   removing the delivery device from the target area; and
   preparing the solution comprising the amphiphilic self-assembling peptide by adding the amphiphilic self-assembling peptide to a buffer comprising at least two salts and adding the buffer to the solution,
   wherein the amphiphilic self-assembling peptide is selected from the group consisting of $(RADA)_4$ (SEQ ID NO: 1), $(IEIK)_3I$ (SEQ ID NO: 2), and $(KLDL)_3$ (SEQ ID NO: 3).

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 2

Ile Glu Ile Lys Ile Glu Ile Lys Ile Glu Ile Lys Ile
1               5                   10

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Lys Leu Asp Leu Lys Leu Asp Leu Lys Leu Asp Leu
1               5                   10

<210> SEQ ID NO 4
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Ala Asp Ala
1

<210> SEQ ID NO 5
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ile Glu Ile Lys
1

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Lys Leu Asp Leu
1
```